US007465549B2

(12) United States Patent
Lynch et al.

(10) Patent No.: US 7,465,549 B2
(45) Date of Patent: *Dec. 16, 2008

(54) METHODS FOR IDENTIFYING AGENTS THAT BIND A LEVETIRACETAM BINDING SITE (LBS) OR COMPETE WITH LEV BINDING TO A LBS OF A SYNAPTIC VESICLE PROTEIN 2 (SV2)

(75) Inventors: Berkley Lynch, Cambridge, MA (US); Karl Nocka, Cambridge, MA (US); Bruno Fuks, Brussels (BE)

(73) Assignee: UCB, S.A., Brussels (BE)

( * ) Notice: Subject to any disclaimer, the term of this patent is extended or adjusted under 35 U.S.C. 154(b) by 182 days.

This patent is subject to a terminal disclaimer.

(21) Appl. No.: 10/725,189

(22) Filed: Dec. 2, 2003

(65) Prior Publication Data

US 2004/0204388 A1    Oct. 14, 2004

Related U.S. Application Data

(60) Provisional application No. 60/506,764, filed on Sep. 30, 2003, provisional application No. 60/430,372, filed on Dec. 3, 2002.

(51) Int. Cl.
*G01N 33/53* (2006.01)
*G01N 33/567* (2006.01)
*G01N 33/00* (2006.01)
*C12P 21/06* (2006.01)

(52) U.S. Cl. .................. 435/7.1; 435/7.21; 435/7.72; 435/7.93; 435/69.1

(58) Field of Classification Search ............... None
See application file for complete search history.

(56) References Cited

U.S. PATENT DOCUMENTS

2002/0082252 A1   6/2002  Hochman .............. 514/214
2002/0142383 A1  10/2002  Merkulov et al.
2003/0009024 A1   1/2003  Curtis
2004/0106147 A1*  6/2004  Lynch et al. ............ 435/7.1

FOREIGN PATENT DOCUMENTS

WO    WO 01/39779       11/2000
WO    WO03016475 A2  *  2/2003

OTHER PUBLICATIONS

Berkower I. Curr. Opi. Biotech. 1996.7:622-628.*
Shorvon et al. J. Neurol. Neurosur. Psych.2002. 72: 426-429.*
Mahrhold et al. FEBS Lett. 2006. 580: 2011-4.*
Bajjalieh SM, et al. SV2, a brain synaptic vesicle protein homologous to bacterial transporters. Science 1992; 257(5074):1271-1273.
Bajjalieh SM, et al. Brain contains two forms of synaptic vesicle protein 2. Proc Natl Acad Sci (USA). 1993; 90(6):2150-2154.
Bajjalieh SM, et al. Differential expression of synaptic vesicle protein 2 (SV2) isoforms. J Neurosci. 1994 ; 14(9):5223-5235.

Buckley, K et al. Identification of a transmembrane glycoprotein specific for secretory vesicles of neural and endocrine cells. J Cell Biol. 1985; 100(4):1284-1294.
Crowder, KM et al. Abnormal neurotransmission in mice lacking synaptic vesicle protein 2A (SV2A). Proc Natl Acad Sci (USA). 1999; 96(26):15268-15273.
Feany, MB et al. The synaptic vesicle protein SV2 is a novel type of transmembrane transporter. Cell. 1992; 70(5):861-867.
Fuks, B, et al. Localization and photoaffinity labelling of the levetiracetam binding site in rat brain and certain cell lines. European Journal of Pharmacology 478 (2003) pp. 11-19.
Hayashi, M et al. Synaptic vesicle protein SV2B, but not SV2A, is predominantly expressed and associated with microvesicles in rat pinealocytes. Adv Exp Med Biol. 1999; 460:91-93.
Janz, R et al. SVOP, an evolutionarily conserved synaptic vesicle protein, suggests novel transport functions of synaptic vesicles. J Neurosci. 1998; 18(22):9269-9281.
Janz, R et al. SV2A and SV2B function as redundant Ca2+ regulators in neurotransmitter release. Neuron. 1999; 24(4):1003-1016.
Janz, R. Knockout mice and SV2 synaptic-vesicle proteins. University of Texas Health Science Center at Houston Neuroscience Research Center Newsletter, 2001; 7(3):1,4-5.
Lynch B, et al. The synaptic vesicle protein SV2A is the binding site for the antiepileptic drug levetiracetam. PNAS, Jun. 29, 2004, vol. 101, No. 26, pp. 9861-9866.
Margineanu, DG et al. Levetiracetam: Mehanisms of action. In: Antiepileptic Drugs, 5ht Editiion. Levy,RH et al. eds. 2002; Lippincott Williams & Wilkins, Philadelphia, PA. pp. 419-427.
Noyer, M et al. The novel antiepileptic drug levetiracetam (ucb L059) appears to act via a specific binding site in CNS membranes. Eur J Pharmacol. 1995; 286(2):137-146.
Pyle, RA et al. Phosphorylation of synaptic vesicle protein 2 modulates binding to synaptotagmin. J Biol Chem. 2000; 275(22):17195-17200.
Schivell, AE et al. Isoform-specific, calcium-regulated interaction of the synaptic vesicle proteins SV2 and synaptotagmin. J Biol Chem. 1996; 271(44):27770-27775.

(Continued)

*Primary Examiner*—Christine Saoud
*Assistant Examiner*—Chang-Yu Wang
(74) *Attorney, Agent, or Firm*—Morgan, Lewis & Bockius LLP

(57) ABSTRACT

The present invention is drawn to methods of characterization of the properties and functions of SV2 proteins. The invention further includes methods of identifying compounds or agents which modulate the activity of SV2 proteins. Included in these methods is the identification of compounds or agents which modulate the binding of levetiracetam to SV2 proteins, including SV2A. Additionally, the present invention provides biotinylated ligands as a tool to screen chemical libraries and characterize the SV2 proteins. Further, the present invention provides a method of solubilizing and purifying functionally active membrane associated proteins, such as SV2.

38 Claims, 23 Drawing Sheets

OTHER PUBLICATIONS

Son, Y-J et al. The synaptic vesicle protein SV2 is complexed with an alpha5-containing laminin on the nerve terminal surface. J Biol Chem. 2000; 275(1):451-460.

Xu, T et al. SV2 modulates the size of the readily releasable pool of secretory vesicles. Nat Cell Biol. 2001; 3(8):691-698.

Nagase et al., Prediction of the Coding Sequences of Unidentified Human Genes. XI. The Complete Sequences of 100 New cDNA Clones from Brain Which Code for Large Proteins in vitro. DNA Research 5, 1998, 277-286.

Genbank Accession 094841, May 1, 1999, KIAA0736 Human SV2.

* cited by examiner

Control + Levetiracetam 1 μM
 
+ Levetiracetam 10 μM + Levetiracetam 100 μM
FIG. 6

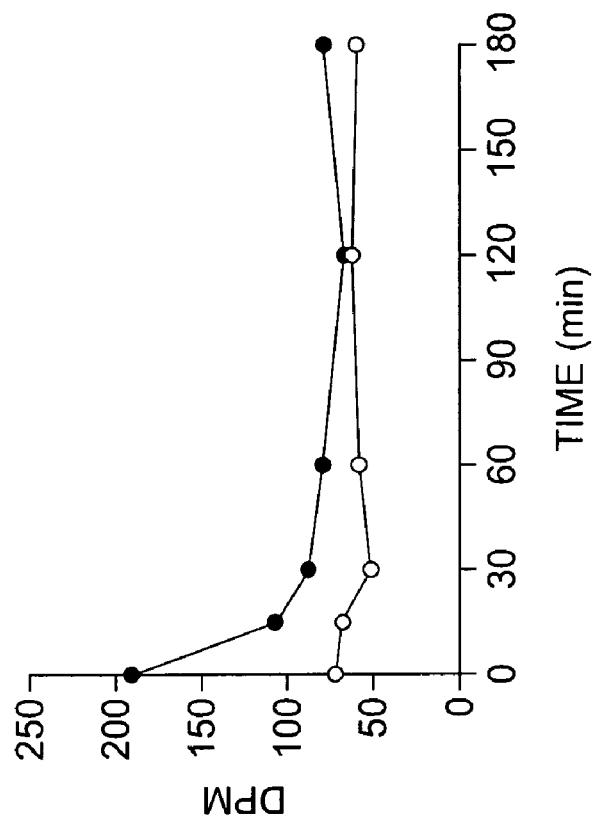
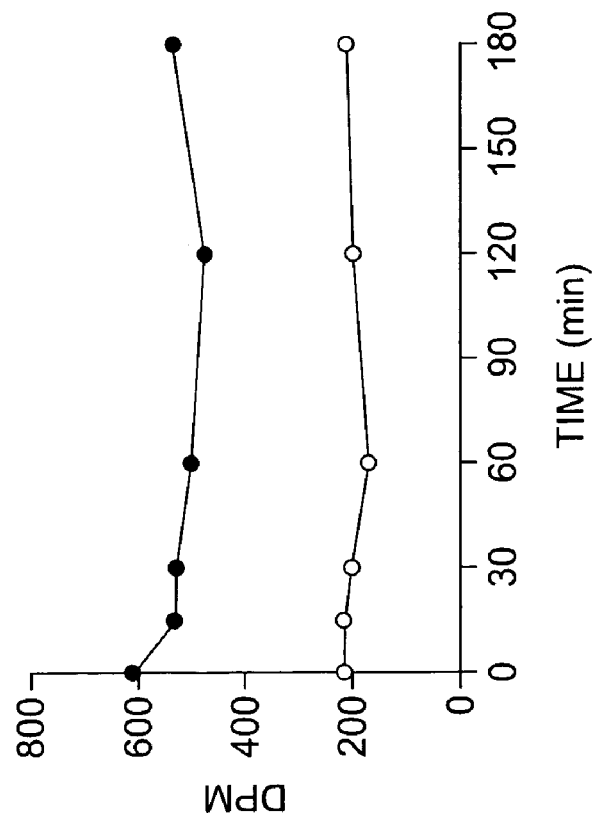
FIG. 10b
FIG. 10a

[3H]ucb 30889

[3H]LEVETIRACETAM

| | ucb-101282-1 | L059 |
|---|---|---|
| BOTTOM | 458.4 | 661.8 |
| TOP | 3923 | 3836 |
| LOGEC50 | -6.392 | -6.129 |
| HILLSLOPE | -0.7946 | -1.237 |
| EC50 | 4.0510e-007 | 7.4320e-007 |

PELLET    SUPERNATANT    BRAIN

|  | MEMBRANES | SOLUBLE EXTRACTS |
|---|---|---|
| BOTTOM | 94.97 | 97.71 |
| TOP | 12.30 | 21.03 |
| LEGEC50 | -6.104 | -5.692 |
| EC50 | 7.8770e-007 | 2.0340e-006 |

|  | MEMBRANES | SOLUBLE EXTRACTS |
|---|---|---|
| BOTTOM | 100.7 | 90.62 |
| TOP | 10.63 | 19.87 |
| LEGEC50 | -7.235 | -6.922 |
| EC50 | 5.8200e-008 | 1.1970e-007 |

METHODS FOR IDENTIFYING AGENTS THAT BIND A LEVETIRACETAM BINDING SITE (LBS) OR COMPETE WITH LEV BINDING TO A LBS OF A SYNAPTIC VESICLE PROTEIN 2 (SV2)

RELATED APPLICATIONS

This application claims the benefit of U.S. Provisional Application 60/506,764, filed Sep. 30, 2003, and U.S. Provisional Application 60/430,372, filed Dec. 3, 2002, which are herein incorporated by reference in their entirety.

FIELD OF THE INVENTION

The present invention is generally drawn to the field of drug discovery in neurological disorders, endocrinopathies and hormonal diseases.

BACKGROUND OF THE INVENTION

Neurological disorders afflict a substantial number of individuals and present an increasing economic challenge to health care systems since little is known regarding their causes, their diagnosis is often subjective, and many lack effective treatment. In general, brain activity is ultimately determined by the capacity of neurons to communicate at synapses. Specific neurotransmitter chemicals are packaged in presynaptic neurons into synaptic vesicles which fuse with the presynaptic membrane to release quanta of the neurotransmitter chemical that traverse the synaptic cleft to activate the corresponding receptor type resident in the postsynaptic membrane. Among these receptor types are the neuronal glutamate receptors (GluR's), γ-aminobutyric acid receptors (GABAR's), nicotinic acetylcholine receptors, serotonin receptors, dopamine receptors, and the like. Many neurological disorders are a result of improper conduction of electrical currents through synapses in various brain tissues. In epilepsy errant currents, hypothesized to be associated with improper function of synapses, cause various levels of seizures. Likewise, in several psychiatric diseases, movement disorders and neurodegenerative diseases the conduction currents become aberrant, disorganized or reduced, thereby causing the disease condition. Accordingly, defects in synaptic vesicle functions will have an adverse effect upon neurotransmission in general and control of neurotransmitter release in particular.

Seizures, including epileptic seizures, result from a focal or generalized disturbance of cortical function, which may be due to various cerebral or systemic disorders, including, for example, cerebral edema, cerebral hypoxia, cerebral trauma, central nervous system (CNS) infections, congenital or developmental brain defects, expanding brain lesions, hyperpyrexia, metabolic disturbances and the use of convulsive or toxic drugs. It is only when seizures recur at sporadic intervals and over the course of years (or indefinitely) that epilepsy is diagnosed.

Epilepsy is classified etiologically as symptomatic or idiopathic with seizure manifestations that fall into three general categories: 1) generalized tonic-clonic, 2) absence or petiti mal, and 3) complex partial. Symptomatic classification indicates that a probable cause exists and a specific course of therapy to eliminate that cause may be tried, whereas idiopathic indicates that no obvious cause can be found and may be linked to unexplained genetic factors. Of the seizure categories, most persons have only one type of seizure, while about 30% have two or more types.

The risk of developing epilepsy is 1% from birth to age 20 yr. and 3% at age 75 yr. Idiopathic epilepsy generally begins between ages 2 and 14. Seizures before age 2 are usually caused by developmental defects, birth injuries, or a metabolic disease. Those beginning after age 25 may be secondary to cerebral trauma, tumors, or cerebrovascular disease, but 50% are of unknown etiology.

Due to the many interrelationships that exist between the nervous and endocrine systems, defects in synaptic vesicle function can also impact on endocrinological function. For instance, at least two glands secrete their hormones only in response to appropriate neurotransmitter release—the adrenal medulla and the posterior pituitary gland. Upon secretion, hormones are transported in the blood to cause physiologic actions at distant target tissues in the body. Obviously, endocrinopathies involving either hyper- or hyposecretion of hormones have pathological consequences. Exemplary of these consequences are giantism and dwarfism, due to hyper- or hyposecretion of growth hormone, respectfully.

Levetiracetam

Levetiracetam (LEV; ucb L059; (S)-α-ethyl-oxo-pyrrolidine acetamide),the (S)-enantiomer of the ethyl analog of piracetam, was synthesized during a follow-up chemical program aimed at identifying a second-generation nootropic drug. In vivo results have demonstrated an unexpected potent ability of LEV to suppress seizures in the audiogenic-susceptible mouse, whereas piracetam was only weakly active. Although LEV is a molecule unrelated to established antiepileptic drugs (Margineanu et al., in Antiepileptic Drugs: 5th Edition. pp. 419-427. Lippincott, Philadelphia (2002)), extensive clinical trials have proven that adjunctive therapy with LEV (KEPPRA, UCB, S.A., Braine-l'Allend, Belgium) is both effective and well tolerated in controlling refractory partial seizures in adults.

Binding assays with LEV, performed on crude rat brain membranes, reveal the existence of a reversible, saturable and stereoselective specific binding site. Results obtained in rat hippocampal membranes suggest that LEV labels a single class of binding sites with modest affinity and with a high binding capacity. This binding site is identified as the Levetiracetam Binding Site (LBS). Similar results have been obtained in other brain regions (cortex, cerebellum and striatum). Ucb L060, the (R)-enantiomer of levetiracetam, displays about 1000 times less affinity for these sites. The binding of LEV appears to be confined to membranes in the central nervous system since radiolabel studies could detect no specific binding in a range of peripheral tissues including heart, kidneys, spleen, pancreas, adrenals, lungs and liver. However, this could be due to a low density of LBS in these tissues compared to the central nervous system and indeed specific binding does occur in PC12 cells, a peripherally derived adrenal cell line.

The most commonly used antiepileptic drugs carbamazepine, phenytoin, valproate, felbamate, gabapentin, tiagabine, vigabatrin, zonisamide, phenobarbital and clonazepam, as well as the convulsant agent t-butylbicyclophosphorothionate (TBPS), picrotoxin and bicuculline do not displace LEV binding (Gillard et al. Eor. J. Pharmacol. 478:1-9. (2003))). However, ethosuximide, pentobarbital, pentylenetetrazole and bemegride competed with LEV with pKi values comparable to active drug concentrations observed in vivo. Structurally related compounds, including piracetam and aniracetam, also displaced LEV binding. The levetiracetam analogues were also tested for their anticonvulsant activity in the audiogenic mouse model of epilepsy. A very good correlation ($r^2$=0.84) was observed between the affinity and the anticonvulsant activity (Noyer et al., Euro. J. Pharmacol.

286:137-146. (1995)). This high degree of correlation is strong support for a causative relationship between LBS binding and anticonvulsant activity of this class of compounds. Accordingly, binding of levetiracetam analogues to LBS is expected to result in modification of the function of the protein component(s) of the LBS in brain, leading to the desired therapeutic outcome of anticonvulsant activity.

The Synaptic Vesicle Protein 2 Family

The Synaptic Vesicle Protein 2 (SV2) family of synaptic vesicle proteins was first identified with a monoclonal antibody prepared against cholinergic vesicles from the electric organ of the marine ray *D. ommata* (Buckley et al., J. Cell Biol. 100: 1284-1294. (1985)). Cloning of the individual family members labeled by the antibody resulted in the identification of three different isoforms, SV2A (Bajjalieh et al., Science. 257:1271-1273. (1992)), SV2B (Feany et al., Cell. 70(5):861-867. 1992) and SV2C (Janz and Sudhof, Neuroscience 94(4): 1279-1290. (1999)), all of which react with the original antibody. The overall homology between the three rat isoforms is approximately 60%, with SV2A and SV2C being more similar to each other than SV2B (Janz and Sudhof, Neuroscience 94(4): 1279-1290. (1999)).

The SV2 proteins are integral membrane proteins and have significant but low-level homology (20-30%) to the twelve transmembrane family of bacterial and fungal transporter proteins that transport sugar, citrate, and xenobiotics (Bajjalieh et al., Science. 257:1271-1273. (1992)). As putative members of the 12 TM superfamily, SV2 proteins display several unique features. They have relatively short free N- and C-termini and short loops connecting the Tm segments. Two notable exceptions, however, are the long cytoplasmic loop between transmembrane regions 6 and 7 and the intravesicular loop between transmembrane regions 7 and 8 (which contains 3 N-glycosylation sites). No close homologs of the SV2 proteins have yet been discovered in yeast or invertebrates, although a distantly related synaptic vesicle protein known as SVOP does have homologs in *Drosophila* and *C. elegans* (Janz et al., J. Neurosci. 18(22):9269-9281. (1998)).

As a family, SV2 proteins are widely distributed in the brain and in endocrine cells. The three isoforms overlap significantly in their distribution, and can be found co-expressed in the same neuron, and even on the same synaptic vesicle. One isoform or another of the SV2 proteins seems to be present on all synaptic vesicles, and they are probably not limited to neurons that contain any specific neurotransmitters, although one study reports that cholinergic vesicles may not contain SV2 (Blumberg et al., J. Neurochem. 58(3):801-810 (1992)). SV2 proteins are therefore one of the most common proteins of synaptic vesicles, and have been implicated in the control of calcium-mediated exocytosis of synaptic vesicles. SV2 proteins have also been shown to be expressed in endocrine cells and, along with the additional synaptic vesicle membrane integral proteins p38 and p65, has been demonstrated to be present in endocrine dense core granule membranes (Lowe et al., J. Cell. Biol. 106(1):51-59 (1988). SV2A, the most common SV2 isoform, is expressed ubiquitously throughout the brain, and is present as well in secretory granules of endocrine cells. SV2B, while broadly distributed in the brain, is undetected in several brain structures, including the dentate gyrus of the hippocampus, the globus pallidus, reticular nuclei of the thalamus, and the reticular part of the substantia nigra (Bajjalieh et al., 1994). By contrast, SV2C has quite a limited distribution and is found primarily in phylogenetically old regions such as the pallidum, the substantia nigra, the midbrain, the brainstem and the olfactory bulb. It is undetectable in the cerebral cortex and the hippocampus, and found at low levels in the cerebellar cortex (Janz and Sudhof, Neuroscience 94(4): 1279-1290. (1999)).

In addition to the SV2 protein, the synapse contains other unique regulatory proteins such as synapsin, synaptotagmin and CAPS, which may mediate vesicle fusion or budding. SV2A may be a $Ca^{2+}$ regulatory protein essential for the formation of pre-fusion complexes called SNARE complexes (Xu et al. Cell 99(7):713-722 (1999)), which include the synaptic vesicle-associated VAMP/synaptobrevin and the plasma membrane proteins syntaxin and SNAP-25. Upon $Ca^{2+}$ accumulation in the synapse the binding of synaptotagmin to SV2A is inhibited and the dimerization of two synaptotagmin $Ca^{2+}$ binding domains is stimulated (Bajjalieh, Curr. Opin. Neurobiol. 9(3):321-328. (1999)). This dimerization may play a role in organizing the SNARE complex and promoting vesicle fusion, as at low $Ca^{2+}$ concentrations, SV2A remains bound to synaptotagmin and fusion will not occur.

The affinity of SV2A for synaptotagmin is regulated by the phosphorylation of the amino terminus of SV2 (Pyle et al., J. Biol. Chem. 275(22):17195-17200. (2000)). The possibility that SV2 proteins play a role in either $Ca^{2+}$ transport, or regulation in the synaptic vesicle has been supported by studies of SV2A and SV2B knockout animals (Janz et al., Neuron 24:1003-1016. (1999)). An alternative hypothesis is that the SV2 proteins, while derived from transport proteins, now serve a different function in the vesicle, whether a structural role or a role in regulation of vesicle fusion or recycling and the exocytotic release of their contents (Janz and Sudhof, Neuroscience 94(4): 1279-1290. (1999)).

There have been two reports of SV2 protein knockout mice: one that examines only SV2A knockouts (Crowder et al., Proc. Nat. Acad. Sci. USA 96(26):15268-15273. (1999)) and the other which looks at both SV2A and SV2B knockout animals, as well as the SV2A/SV2B double knockout (Janz et al., Neuron 24:1003-1016. (1999)).

Animals homozygous for SV2A gene disruption appear normal at birth, but fail to grow, experience severe seizures, and die within the first few weeks postnatal. SV2A homozygous knockout mice experience seizures that are longer lasting, stronger, and more debilitating than any other mouse strain (Janz et al., Neuron 24:1003-1016. (1999)). Despite the appearance of postnatal seizures, all SV2A knockout animals have completely normal gross brain morphology, including normal levels of the tested synaptic proteins. Furthermore, the hippocampal neuronal cultures from both SV2A and SV2A/SV2B double knockout mice formed synapses that were ultrastructurally normal, and had unchanged size, number and location of synaptic vesicles (Janz et al., Neuron 24:1003-1016. (1999); Crowder et al., Proc. Nat. Acad. Sci. USA 96(26):15268-15273. (1999)). Unlike the frequently observed seizures caused by structural and developmental abnormalities easily detected in many other type of knockouts, the SV2A knockout mice show a strong seizure phenotype with no associated macro or micro scale abnormalities of the brain or synapse. As another marker of brain function, studies of synaptic transmission in primary neuronal cultures from SV2A, SV2B, and SV2A/SV2B knockout mice indicate that the sizes and frequencies of sIPSCs and of spontaneous excitatory postsynaptic currents (sEPSCs), are normal. Electrical stimulation induced robust EPSCs and IPSCs in the cultured neurons from all genotypes.

In contrast to SV2A, SV2B knockout mice reveal no overt pathology (Janz et al., 1999). It is suggested that one possible reason for this lack of consequence of loss of SV2B is that can be functionally replaced by SV2A, which appears to be co-expressed everywhere SV2B is normally expressed.

While the function of SV2A and other family members still remains unknown, one hypothesis is that this transporter homologue is a functional transporter for some common synaptic vesicle molecule. More specifically, there is evidence linking SV2A to the regulation of calcium-mediated vesicle exocytosis, and as a result, it is thought that it may be a $Ca^{2+}$ transporter. SV2A and other family members may also have roles in the function of synaptic vesicles. Such roles may include modulating aspects of their formation, loading with neurotransmitter, fusion with the plasma membrane, re-cycling, and interactions with other proteins and cellular compartments and organelles. For instance it has been shown that SV2 proteins can interact with the synaptic vesicle protein synaptotagmin and the extracellular matrix protein laminin-1 (Carlson, Perspect. Dev. Neurobiol. 3(4):373-386 (1996)). The SV2 proteins may play important roles in regulating cytoplasmic or organellar calcium levels at the presynaptic terminal, and may also interact with N-type calcium channels on the plasma membrane, either directly or indirectly.

SUMMARY OF THE INVENTION

The present inventors have discovered that SV2A is the binding site for the anti-seizure drug LEV and its analogs. The high degree of correlation between relative binding affinities of a series of levetiracetam analogues and their anti-convulsant potencies in certain animal models of epilepsy provides strong evidence that binding of these analogues to SV2 proteins modifies their function to provide anticonvulsant effects.

In a preferred embodiment, the invention includes a method of treating a neurological disorder associated with synaptic vesicle function, endocrinopathy or hormonal diseases, comprising administering a compound or agent that modulates a function or activity of an SV2 protein.

In another preferred embodiment, the invention includes a method of discovering or modeling an interaction between an SV2 protein and a compound or agent selected from the group consisting of: levetiracetam, an analog or derivative of levetiracetam, or a compound or agent which competes with levetiracetam or an analog or derivative thereof for binding to the levetiracetam binding site. The method comprises contacting the SV2 protein with the compound or agent measuring and analyzing the interaction of the SV2 protein with the compound or agent.

In another preferred embodiment, the invention includes a method of identifying a levetiracetam binding site within an SV2 protein. The method comprises contacting a SV2 protein or fragment thereof with a compound or agent selected from the group consisting of levetiracetam, an analog or derivative of levetiracetam, or a compound or agent which competes with levetiracetam or an analog or derivative thereof for binding to the levetiracetam binding site and determining the binding of the compound or agent with the SV2 protein or fragment thereof.

In another preferred embodiment, the invention includes a method of assaying the interaction between SV2 protein and a second protein. The method comprises expressing SV2 protein and the protein of interest in a cell. The method further comprises exposing the cell to a compound or agent which binds to the levetiracetam binding site and determining the interaction between the SV2 protein and the protein of interest.

In another preferred embodiment, the invention includes a method of identifying a compound or agent that modulates a neurological disorder associated with synaptic function, endocrinopathy or hormonal disease. The method comprises exposing a SV2 protein to the compound or agent and determining whether the compound or agent modulates an activity of the SV2 protein.

In another preferred embodiment, the invention includes a method of identifying a cellular response to a compound or agent selected from the group consisting of levetiracetam, an analog or derivative of levetiracetam, or a compound or agent which competes with levetiracetam or an analog or derivative thereof for binding to the levetiracetam binding site. The method comprises exposing cells expressing an SV2 protein to the compound or agent and analyzing a change in the expression of a nucleic acid or protein in the exposed cell. The nucleic acid could be RNA, and the expression of the RNA may be analyzed by hybridization, such as hybridization on a microarray.

In another preferred embodiment, the invention includes an isolated nucleic acid molecule comprising the nucleic acid sequence of SEQ ID NO: 5 or the complement thereof.

In another preferred embodiment, the invention includes a method of identifying a binding partner for a SV2 protein. The method comprises exposing a SV2 protein or fragment to a potential binding partner and incubating the protein or fragment and potential binding partner with (2S)-2-[4-(3-azidophenyl)-2-oxopyrrolidin-1-yl]butanamide. The method further comprises determining if the binding of (2S)-2-[4-(3-azidophenyl)-2-oxopyrrolidin-1-yl]butanamide to the protein is inhibited by the potential binding partner, thereby identifying binding partner for the protein.

In still another preferred embodiment, the invention includes a method of identifying an agent useful for the treatment of a neurological or endocrinological disorder. The method comprises exposing a SV2 protein or fragment to the agent and levetiracetam or an analog or derivative thereof. The method further comprises determining if the binding of levetiracetam or an analog or derivative thereof to the protein is modulated by the agent, thereby identifying an agent useful for the treatment of a neurological or endocrinological disorder.

In yet another preferred embodiment, the invention includes a method of identifying an agent useful for the treatment of a neurological or endocrinological disorder. The method comprises exposing a SV2 protein or fragment to the agent and incubating the protein or fragment and agent with (2S)-2-[4-(3-azidophenyl)-2-oxopyrrolidin-1-yl]butanamide. The method further comprises determining if the binding of (2S)-2-[4-(3-azidophenyl)-2-oxopyrrolidin-1-yl]butanamide to the protein is inhibited by the agent, thereby identifying binding partners for the protein.

In another preferred embodiment, the invention includes a method of discovering or modeling an interaction between an SV2 protein, or fragment or derivative thereof, and a compound or agent selected from the group consisting of: levetiracetam, an analog or derivative of levetiracetam, or a compound or agent which competes with levetiracetam or an analog or derivative thereof for binding to the levetiracetam binding site. The method comprises creating a 3-dimensional model of the SV2 protein, or fragments thereof, via either biochemical, biophysical, purely computational techniques, or some combination of these and creating 3-dimensional model of one or a collection of potential ligands that might potentially bind the SV2 protein.

In another preferred embodiment, the invention includes a method of discovering or modeling an interaction between an SV2 protein and a compound or agent selected from the group consisting of: levetiracetam, an analog or derivative of levetiracetam, or a compound or agent which competes with levetiracetam or an analog or derivative thereof for binding to the levetiracetam binding site. The method comprises determining a biochemical, pharmacological, organismal, cellular or molecular effect of a potential CNS active molecule in a genetically wild-type animal or in molecules, cells or tissues derived from such animals and comparing the measured effect of that compound in an equivalent study in a system with an SV2 protein knocked out or knocked down.

The present invention also provides biotinylated ligands as tools to screen chemical libraries, localize SV2 proteins in tissues, and characterize purified SV2 proteins. SV2 proteins of the present invention includes SV2A, SV2B, and SV2C. Ligands of SV2/LBS, specifically SV2A/LBS, and their derivatives may be biotinylated for screening naturally occurring brain membranes, such as animal, mammalian, or human brain membranes, or for screening cell lines expressing SV2 proteins. The present invention also provides photoactivable biotinylated ligands of SV2/LBS. These screening assays enable the identification of new drugs or compounds that interact with SV2.

Further, the present invention provides a method of purifying a membrane associated protein comprising solubilizing the protein from a tissue to form a solubilized complex and isolating the solubilized complex in a functional form. The solubilized protein or complex may be affinity purified using antibodies that bind to the protein. Examples of membrane associated proteins that may be purified by this method include the family of SV2 proteins such as SV2A, SV2B, and SV2C. The detergents that may be used in the present method includes n-dodecyl-β-maltoside and its analogs or derivatives such as n-octyl, n-nonyl, n-decyl, n-undecyl-β-D-maltoside.

The biotinylated ligands also can be used as tools to assess the conformation state of SV2 proteins after solubilization, immunoaffinity purification, and chromatography.

In one embodiment, the SV2 protein may be a fusion protein comprising at least one SV2 protein or fragment thereof and fusion partner. The fusion partner may be a fusion tag, such as a poly-histidine tag or a glutathione-S-transferase tag. The fusion partner may be attached to the N-terminus or the C-terminus of the SV2 protein.

In another embodiment, the protein, such as the SV2 protein, may lack at least one glycosylation site. In some instances, site-directed mutagenesis may be performed to remove one or more glycosylation site in the SV2 protein.

The SV2 protein or fragment may be purified from natural sources such as mammalian membranes, for example, rat brain membrane. Alternatively, the SV2 protein or fragment is expressed on a transformed host cell. Additionally, the SV2 protein or fragment is immobilized.

In one aspect, the ligand could be directly or indirectly labeled. The label could be a radiolabel, such as $^3$H, a fluorescent label, or an enzyme.

BRIEF DESCRIPTION OF THE DRAWINGS

FIG. 6 depicts the concentration dependent inhibition of [$^3$H]ucb 30889 binding by unlabeled levetiracetam in autoradiography of rat brain.

FIG. 10(a and b) depicts the photolabelling of the LBS by [$^3$H]ucb 30889 and irreversibility of the complex. Crude synaptosomes (●, closed symbols) were preincubated with [$^3$H] ucb 30889 then irradiated with UV light and washed. Non-specific binding (○, open symbol) was determined using levetiracetam.

DETAILED DESCRIPTION

Figure 1:
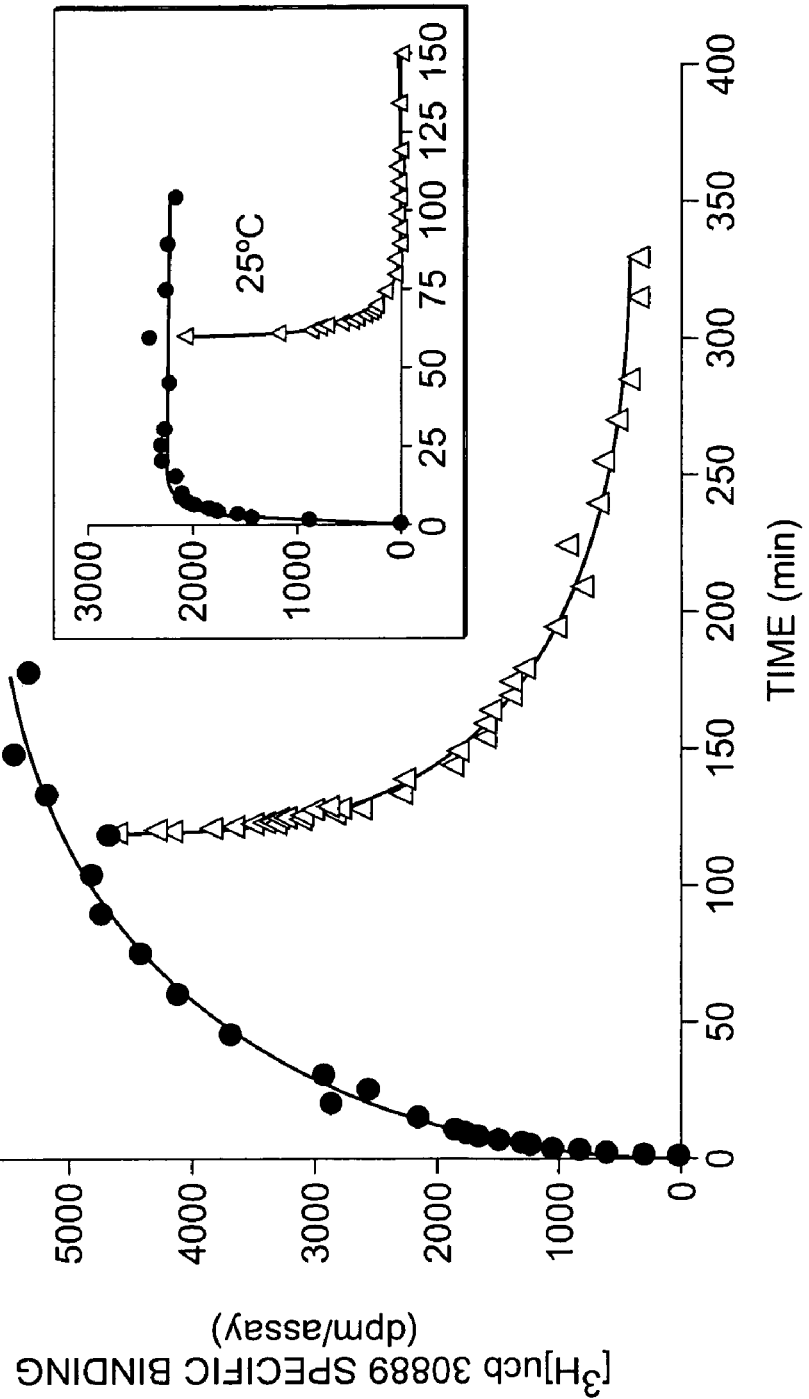
FIG. 1 depicts the reversible binding of the LEV analog ucb 30889 to LBS in rat brain cortex.

I. Synaptic Vesicle Protein 2 (SV2) Family of Proteins

Any SV2 protein that binds LEV or a derivative or analog thereof may be used in the assays herein described.

As used herein, SV2 proteins include isolated proteins, allelic variants of the proteins, and conservative amino acid substitutions of the proteins. As used herein, the "protein" or "polypeptide" refers, in part, to SV2A, a protein encoded by the nucleic acid sequence of SEQ ID NO: 1 or that has the human amino acid sequence depicted in SEQ ID NO: 2 or fragments thereof; to SV2B, which includes the human protein encoded by the nucleic acid sequence of SEQ ID NO: 3 or the amino acid sequence depicted in SEQ ID NO: 4 or fragments thereof; to SV2C, which includes the human protein encoded by the nucleic acid sequence of SEQ ID NO: 5 or the amino acid sequence depicted in SEQ ID NO: 6 or fragments thereof; and to SVOP, which includes the human protein encoded by the nucleic acid sequence of SEQ ID NO: 7 or the amino acid sequence depicted in SEQ ID NO: 8 or fragments thereof. The terms also refer to naturally occurring allelic variants and proteins that have a slightly different amino acid sequence than that specifically recited above. Allelic variants, though possessing a slightly different amino acid sequence than those recited above, will still have the same or similar biological functions associated with these proteins.

As used herein, the family of SV2 proteins related to the human amino acid sequence of SEQ ID NO: 2, 4, 6 or 8 refers in part, to proteins that have been isolated from organisms in addition to humans. For example, rat homologues of SV2A nucleic acid (SEQ ID NO: 9) and protein (SEQ ID NO: 10), SV2B nucleic acid (SEQ ID NO: 11) and protein (SEQ ID NO: 12), SV2C nucleic acid (SEQ ID NO: 13) and protein (SEQ ID NO: 14) and SVOP nucleic acid (SEQ ID NO: 15) and protein (SEQ ID NO: 16) have been identified and are included herein. The methods used to identify and isolate other members of the family of proteins related to these proteins are described below.

The SV2 proteins used in the present invention are preferably in isolated form in part of a cellular or vesicle membrane fragment, expressed in a transformed host cell, or naturally expressed in a given cell or tissue type. As used herein, a protein is said to be isolated when physical, mechanical or chemical methods are employed to remove the protein from cellular constituents that are normally associated with the protein. A skilled artisan can readily employ standard purification methods to obtain an isolated protein.

The SV2 proteins that may be used in the methods of the invention further include insertion, deletion, conservative amino acid substitution or splice variants of SEQ ID NO: 2, 4, 6, 8, 10, 12, 14 or 16. As used herein, a "conservative" variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein. As used herein, a "deletion" is defined as a change in either nucleotide or amino acid sequence in which one or more nucleotides or amino acid residues, respectively, are absent; an "insertion" or "addition" is that change in a nucleotide or amino acid sequence which has resulted in the addition of one or more nucleotides or amino acid residues, respectively, as compared to the naturally occurring SV2 and a "substitution" results from the replacement of one or more nucleotides or amino acids by different nucleotides or amino acids, respectively.

SV2 proteins of the present invention further include fusion proteins, wherein a SV2 protein, or fragment thereof, is N- or C-terminally fused to another SV2 protein or fragment thereof, which may be the same as or different from the first SV2 protein or fragment thereof, and/or to a heterologous peptide fusion partner. The heterologous peptide may be a polypeptide sequence useful for the expression, purification, solubility, identification, antigenicity, or extension of the stability of the SV2 protein or fragment thereof. Heterologous fusion partners useful in the present invention include, but are not limited to, glutathione-S-transferase (GST), poly-histidine tags, green fluorescent protein (GFP), albumin, and ovalbumin or fragments thereof.

Ordinarily, the allelic variants, the conservative substitution variants, and the members of the SV2 protein family, will have an amino acid sequence having at least about 35%, 40%, 50%, 60%, 65%, 70% or 75% amino acid sequence identity with the full length sequence set forth in SEQ ID NO: 2, 4, 6, 8, 10, 12, 14 or 16 more preferably at least about 80%, even more preferably at least about 90%, and most preferably at least about 95%, 97% or 99% sequence identity. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

Fragments of the SV2 proteins may also be used in the methods of the invention. In particular, fragments comprising the LEV binding site may be used. Such fragments may have at least about 6 or 10, 15 or 20, or 25 or 30 amino acid residues, about 35 or 40 amino acid residues, about 45 or 50 amino acid residues, about 55 or 60, about 65 or 70 amino acid residues or at least about 75 or more amino acid residues The methods of the present invention may also utilize nucleic acid molecules that encode members of the SV2 protein family, including, but not limited to, both the rat and human proteins known as SV2A, SV2B, SV2C and the related synaptic vesicle protein SVOP, such as those consisting of or comprising SEQ ID NO: 2, 4, 6, 8, 10, 12, 14 or 16 and the related proteins herein described, preferably in isolated form. Vectors, plasmids and transformed host cells may also be used to produce an SV2 protein. As used herein, "nucleic acid" is defined as RNA or DNA or related molecules that encodes a protein or peptide as defined above, is complementary to a nucleic acid sequence encoding such peptides, hybridizes to such a nucleic acid and remains stably bound to it under appropriate stringency conditions, or encodes a polypeptide sharing at least about 35%, 40%, 50%, 60%, 65%, 70% or 75% sequence identity, preferably at least about 80%, more preferably at least about 85%, and even more preferably at least about 90%, 95%, 97% or 99% or more identity with the full-length peptide sequence of SEQ ID NO: 2, 4, 6, 8, or 10. The "nucleic acid molecules" useful in the invention further include nucleic acid molecules that share at least about 70% or 75% sequence identity, preferably at least about 80%, more preferably at least about 85%, and even more preferably at least about 90% and most preferably 95%, 97%, 99% or more identity with the nucleotide sequence of SEQ ID NO: 1, 3, 5, 7, or 9. Nucleic acids of the present invention also include those which encode fusion proteins comprising a SV2 protein either N- or C-terminally fused to a heterologous protein sequence or to another SV2 protein sequence.

Homology or identity at the nucleotide or amino acid sequence level is determined by BLAST (Basic Local Alignment Search Tool) analysis using the algorithm employed by the programs blastp, blastn, blastx, tblastn and tblastx (Altschul, et al., Nucleic Acids Res. 25: 3389-3402 (1997); Karlin et al., Proc. Natl. Acad. Sci. USA 87:2264-2268 (1990)) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (Nature Genetics 6, 119-129 (1994)). The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al., Proc. Natl. Acad. Sci. USA 89:10915-10919 (1992)), recommended for query sequences over 85 in length (nucleotide bases or amino acids).

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Gap comparison between sequences, available in the Accelrys' Wisconsin Package version 10.2, uses DNA parameters GAP=50 (gap creation penalty) and LEN=3 (gap extension penalty) and the equivalent settings in protein comparisons are GAP=8 and LEN=2.

"Stringent conditions" include those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1, 3, 5, 7, 9, 11, 13 or 15 and which encode a functional protein. Even more preferred hybridizing molecules are those that hybridize under the above conditions to the complement strand of the open reading frame of SEQ ID NO: 1, 3, 5, 7, 9, 11, 13 or 15.

As used herein, a nucleic acid molecule is said to be "isolated" when the nucleic acid molecule is substantially separated from contaminant nucleic acid molecules encoding other polypeptides.

A. SV2A and the Levetiracetam Binding Site (LBS)

The invention includes the characterization and use of the LBS located on the SV2A protein.

As described above, "SV2A" includes the human protein as described in SEQ ID NO: 2, the human protein encoded by SEQ ID NO: 1, species homologues of human SV2A, variants of SEQ ID NO: 2 as herein described, and fragments of SV2A comprising the LBS.

II. Levetiracetam and Analogs

The methods of the invention include the use of LEV and LEV analogs or derivatives thereof in assays to identify new pharmacological agents. In a preferred embodiment, the methods of the present invention identify compounds or agents that compete with LEV and LEV analogs or derivatives thereof for binding to the LBS of SV2. As used herein, the terms "compete" and "competitive binding" refer to agents or compounds which occupy the same binding site on the LBS as LEV or analogs or derivatives thereof; displace, or are displaced by, LEV or analogs or derivatives thereof in binding to the LBS; or inhibit, or are inhibited by, LEV or analogs or derivatives thereof in binding to the LBS. In another preferred embodiment, the invention includes the identification of compounds or agents that modulate the activity of SV2A. In another preferred embodiment the methods of the present invention identify compounds or agents which have less, about the same, or greater affinity for the LBS than LEV. In yet another preferred embodiment the methods of the present invention identify compounds or agents which have less, about the same, or greater affinity for the LBS than ucb 30889. In still another preferred embodiment the methods of the present invention identify compounds or agents which in an effective amount modulate the activity of SV2A for a longer period of time than an effective amount of LEV. In even another preferred embodiment the methods of the present invention identify compounds or agents which in an effective amount modulate the activity of SV2A for a shorter period of time than an effective amount of LEV.

Figure 15B:
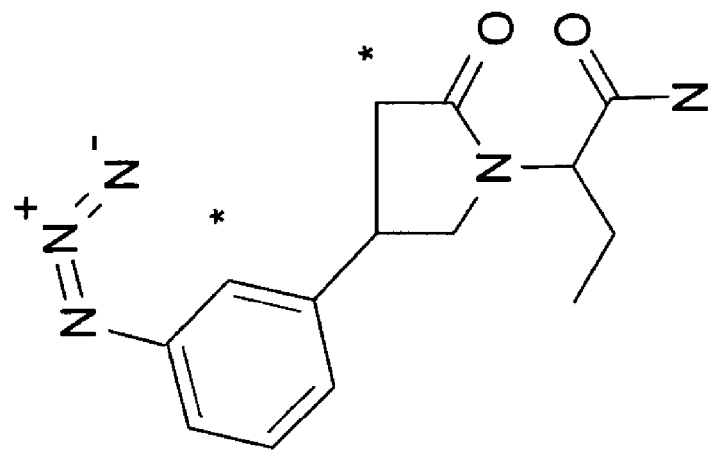
FIG. 15(a and b) depicts the structure of (A) levetiracetam and (B) ucb 30889.
Figure 15A:
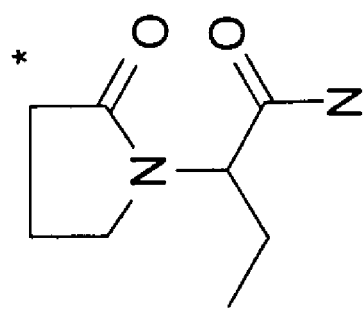
Figure 16B:
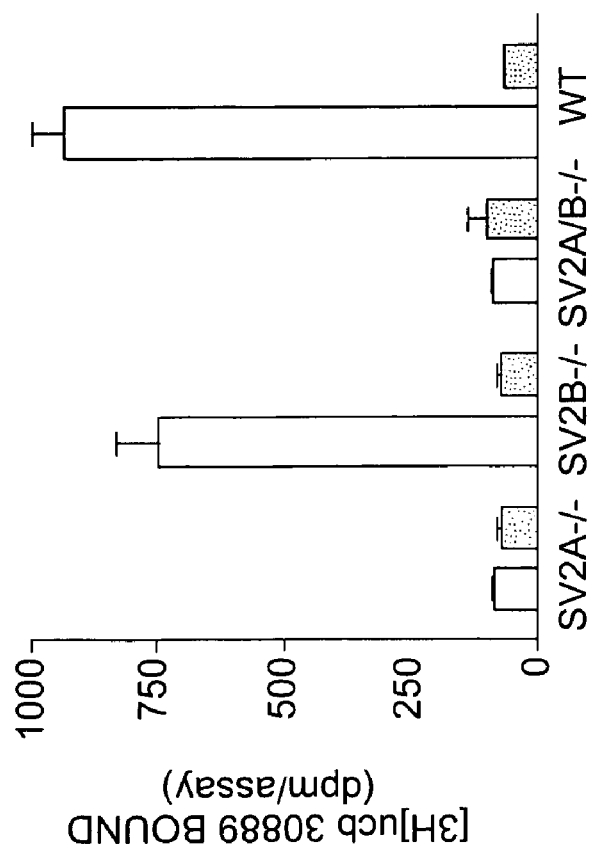
FIGS. 16(a and b) depicts binding of [$^3$H]ucb 30889 to brain membranes. A. Binding of [$^3$H]ucb 30889 to brain membranes from SV2A, SV2B, and SV2A/SV2B knockout mice. [$^3$H]ucb 30889 alone (□) [$^3$H]ucb 30889 plus 1 mM LEV (■). Error bars are the SD of experiments performed with 5 wildtype brains and 4 KO brains. Each experiment was performed in triplicate. B. Western blot of brain membranes from wild type and homozygous knockout mice probed with an anti-SV2 monoclonal antibody (cross-reactive to all isoforms, SV2A, SV2B and SV2C). LANES 1: wt; 2: SV2A ko; 3 SV2B ko; 4: SV2A/B double ko.
Figure 16A:
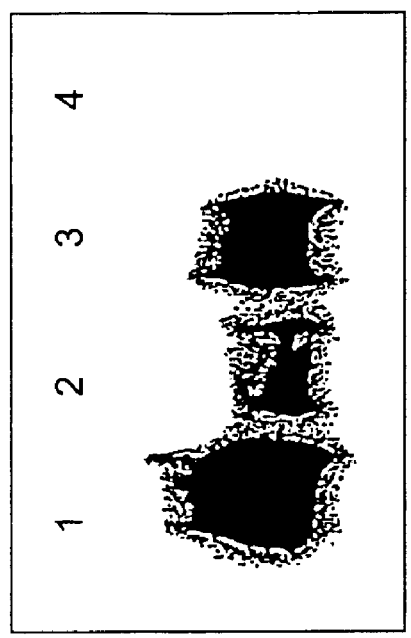

As used herein, "levetiracetam" (FIG. 15A; LEV), refers to the International Non-proprietary name of the compound (S)-α-ethyl-2-oxo-1-pyrrolidine acetamide as disclosed in European Patent No. 0 162 036 B1, herein incorporated by reference in its entirety. LEV is a levorotary compound which is a protective agent for the treatment and prevention of hypoxic and ischemic type aggressions of the central nervous system. This compound is also effective in the treatment of epilepsy. Racemic α-ethyl-2-oxo-1-pyrrolidine acetamide and analogs thereof are known from British Patent No. 1 309 692. U.S. Pat. No. 3,459,738 discloses derivatives of 2-oxo-1-pyrrolidine acetamide.

As used herein, the term "LEV analogs or derivatives thereof" includes optionally substituted N-alkylated 2-oxopyrrolidine derivatives. Preferably, those compounds are alkyl amides derivatives substituted on the positions 4 and/or 5 of the pyrrolidone ring. Examples of optionally substituted N-alkylated 2-oxo-pyrrolidine derivatives include, but are not limited to, compounds such as those disclosed in international patent application PCT/EP01/01992 such as (2S)-2-[(4S)-4-(2,2-difluorovinyl)-2-oxopyrrolidinyl]butanamide, (2S)-2-[(4R)-2-oxo-4-propylpyrrolidinyl]butanamide, (2S)-2-[(4S)-2-oxo-4-propylpyrrolidinyl]butanamide, and (2S)-2-[4-(3-azidophenyl)-2-oxopyrrolidin-1-yl]butanamide.

As used herein, the term "LEV analogs or derivatives thereof" further include optionally substituted N-alkylated 2-oxo-piperidinyl derivatives. Preferably, those compounds are alkyl amides derivatives substituted on the position 4 and/or 5 and/or 6 of the 2-oxo-piperidinyl ring. Examples of optionally substituted N-alkylated 2-oxo-pyrrolidine derivatives include, but are not limited to, compounds such as those disclosed in international patent application PCT/EP02/05503 such as (2S)-2-[5-(iodomethyl)-2-oxo-1-piperidinyl]butanamide, (2S)-2-[5-(azidomethyl)-2-oxo-1-piperidinyl]butanamide, 2-(2-oxo-5-phenyl-1-piperidinyl]butanamide, (2S)-2-[4-(iodomethyl)-2-oxo-1-piperidinyl]butanamide, and (2S)-2-[4-(2-fluoro-2-methylpropyl)-2-oxo-1-pyrrolidinyl]butanamide.

As used herein, the term "LEV analogs or derivatives thereof" includes any acetam compound of formula I, in racemic or isomeric form, or a pharmaceutically acceptable salts thereof,

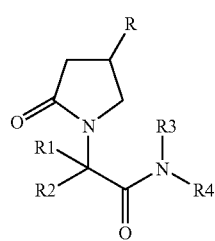 (I)

wherein
R represents hydrogen or hydroxy;
$R^1$ and $R^2$ represent independently hydrogen or an alkyl group of 1-4 carbon atoms; and
$R^3$ and $R^4$ represent independently hydrogen, an alkyl group of 1-4 carbon atoms or —$(CH_2)_n$—$NR^5R^6$ wherein n is 1, 2 or 3 and $R^5$ and $R^6$ represent independently hydrogen or an alkyl group of 1-4 carbon atoms.

An example of such an acetam compound includes, but is not limited to, a compound of formula I wherein R, $R^1$, $R^2$, $R^3$ and $R^4$ are hydrogen, 2-oxo-pyrrolidineacetamide, known by the generic name piracetam as described in UK Patents Nos. 1,039,113 and 1,309,692.

As used herein, the term "LEV analogs or derivatives thereof" also include optionally substituted N-alkylated 2-oxo-azepanyl derivatives. Preferably, those compounds are alkyl amides derivatives substituted on the positions 4 and/or 5 and/or 6 and/or 7 of the 2-oxo-azepanyl ring. Examples of optionally substituted N-alkylated 2-oxo-azepanyl derivatives include, but are not limited to, compounds such as those disclosed in international patent application PCT/EP02/05503 such as 2-[5-(iodomethyl)-2-oxo-1-azepanyl]butanamide.

In another embodiment the present invention includes compounds or agents which are derivatives or analogs of piracetam which bind to the LBS. Such compounds would also include molecules such as aniracetam and nefiracetam. In a preferred embodiment, the derivatives or analogs of piracetam are those which modulate the activity of SV2A or other SV2 family members.

III. Assay Formats

Assays of the present invention include methods of identifying agents or compounds which are useful for the treatment of neurological disorders, such as seizures, epilepsy, Parkinson's disease, Parkinson's dyskinesias, migraine, Alzheimer's disease, neuropathic pain, essential tremor, cognitive disorders, movement disorders, endocrinopathy and adrenal-medulla-related disease, such as hypoglycemia and circulation shock. Assays of the present invention also include methods of identifying agents or compounds which have cognitive enhancing effects, such as for example might be measured in animal models of cognition. In particular, the assays of the present invention include methods of identifying agents or compounds that compete with LEV or analogs or derivatives thereof for binding to the LBS of SV2A, displace, or are displaced by, LEV or analogs or derivatives thereof in binding to the LBS; or inhibit, or are inhibited by, LEV or analogs or derivatives thereof in binding to the LBS.

LEV, ucb 30889 (FIG. 15B) and other derivatives or analogs of LEV as described above are useful in the methods of the invention as binders in assays to screen for new compounds or agents that bind to the LBS of SV2A. In such assay embodiments, LEV, ucb 30889 and derivatives or analogs can be used without modification or can be modified in a variety of ways; for example, by labeling, such as covalently or non-covalently joining a moiety which directly or indirectly provides a detectable signal. In any of these assays, the materials can be labeled either directly or indirectly. Possibilities for direct labeling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. In addition, FRET techniques could be used to analyze interactions between ligands and the LBS of SV2A. Possibilities for indirect labeling include biotinylation of one constituent followed by binding to avidin coupled to one of the above label groups or the use of anti-ligand antibodies. The compounds may also include spacers or linkers in cases where the compounds are to be attached to a solid support.

To identify agents or compounds which compete or interact with LEV and ucb 30889 and derivatives for binding to the LBS of SV2A, intact cells, cellular or membrane fragments containing SV2A or the entire SV2A protein or a fragment comprising the LBS of the SV2A protein can be used. The agent or compound may be incubated with the cells, membranes, SV2 protein or fragment prior to, at the same time as, or after incubation with LEV or an analog or derivative thereof. Assays of the present invention can measure any property or function known for SV2 proteins, synaptic vesicles, neural transmission and/or endocrine cell function, as well as presynaptic accumulation of divalent cations, including $Ca^{2+}$. Examples of properties or functions of an SV2 protein which may be measured as an assay endpoint include, but are not limited to, phosphorylation state, binding of divalent cations, including $Ca^{2+}$; membrane transport; transport of divalent cations (including $Ca^{2+}$) into and/or out of synaptic vesicles; transport of neurotransmitters (including, but not limited to amines, acetylcholine, excitatory neurotransmitters, GABA, serotonin, and glycine) into and/or out of synaptic vesicles; interaction with other proteins (including, but not limited to laminins and synaptotagmin); conformational changes, as measured by sensitivity to proteolysis or other changes in biochemical or biophysical properties; divalent cation channel formation; formation or dissociation of protein complexes; synaptic vesicle function; fusion; exocytosis; and synaptic vesicle recycling.

Assays of the invention may be modified or prepared in any available format, including high-throughput assays that monitor the binding of LEV or the binding of derivatives or analogs thereof to SV2A or to the LBS of the SV2A protein. In many drug screening programs which test libraries of compounds, high throughput assays are desirable in order to maximize the number of compounds surveyed in a given period of time. Such screening assays may use intact cells, cellular or membrane fragments containing SV2A as well as cell-free or membrane-free systems, such as may be derived with purified or semi-purified proteins. The advantage of the assay with membrane fragment containing SV2A or purified SV2A proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules.

In one embodiment of a competitive screening assay, the assay can be formulated to detect the ability of a test agent or compound to inhibit binding of ucb 30889 to SV2A or a fragment of SV2A comprising the LBS or of LEV, or derivatives or analogs thereof, to SV2A or a fragment of SV2A comprising the LBS. In another embodiment of a competitive screening assay, the assay can be formulated to detect the ability of ucb 30889 or of LEV, or derivatives or analogs thereof, to inhibit binding of a test agent or compound to SV2A or a fragment of SV2A comprising the LBS. The inhibition of complex formation may be detected by a variety of techniques. For instance, modulation of the formation of complexes can be quantitated using, for example, detectably labeled ucb 30889, LEV, or derivatives or analogs of LEV. The inhibition of complex formation may be detected by using a detectably labeled version of the agent or compound being assayed for competitive binding to the LBS of SV2A. Alternatively, the binding between the SV2A protein and a ligand may be detected with no need of a labeled probe. For instance surface plasmon resonance, nuclear magnetic resonance or mass spectrometry are the instruments of choice for such binding assays. Another method is to measure changes in the sensitivity of SV2 proteins to proteases induced by binding of a ligand.

In certain instances, it will be desirable to immobilize one of the LBS (SV2A or a fragment of SV2A comprising the LBS) or the ligand (LEV, ucb 30889 or the test agent or compound) to facilitate separation of complexes from uncomplexed forms, as well as to accommodate automation of the assay. Binding of a ligand to the LBS, for instance binding of a candidate agent or compound to SV2A, in the presence and absence of LEV or ucb 30889, can be accomplished in any vessel suitable for containing the reactants. Examples include microtiter plates, test tubes, and microcentrifuge tubes. In one embodiment, a fusion protein can be provided which adds a domain that allows the LBS to be bound to a matrix. For example, glutathione-S-transferase (GST) fusion proteins can be adsorbed onto glutathione sepharose beads (Sigma Chemical, St. Louis, Mo.) or glutathione derivatized microtiter plates, which are then combined with the labeled LEV, ucb 30889, or derivatives or analogs of LEV and the unlabeled test agent or compound; or alternatively, with the unlabeled LEV, ucb 30889, or derivatives or analogs of LEV and the labeled test agent or compound. The mixture is then incubated under conditions conducive to complex formation. Following incubation, the beads are washed to remove any unbound reactants, and the matrix immobilized label determined directly, or in the supernatant after the LBS/ligand complexes are subsequently dissociated. When amenable, the complexes can be dissociated from the matrix, separated by SDS-PAGE, and the level of ligand found in the bead fraction quantitated from the gel using standard electrophoretic techniques.

Other techniques for immobilizing proteins on matrices are also available for use in the subject assay. For instance, the LBS can be immobilized utilizing conjugation of biotin and streptavidin. Biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the LBS but which do not interfere with ligand binding can be derivatized to the wells of the plate, and LBS binding trapped in the wells by antibody conjugation. As above, preparations of a ligand and a test compound are incubated in the protein-presenting wells of the plate, and the amount of protein/ligand complex trapped in the well can be quantitated. Exemplary methods for detecting such complexes, in addition to those described above, include immunodetection of complexes using antibodies reactive with the ligand, or which are reactive with the protein and compete for binding with the ligand.

In another embodiment of the invention, competitive binding assays can be carried out using cellular extracts of cells or tissues that comprise the LBS to identify SV2 binding partners. As used herein, a cellular extract refers to a preparation or fraction that is made from a lysed or disrupted cell. The preferred source of cellular extracts will be cells derived from human central nervous tissue or endocrine tissues. In particular, cellular extracts may be prepared from a particular region, including, but not limited to, the hippocampus, the cerebellum, the cerebrum, the cerebral cortex, the pituitary, the medulla, and the adrenal gland. Further, cellular extracts may be prepared from a particular primary cell isolate of central nervous system origin or the endocrine systems including, but not limited to, neurons, astrocytes, and endocrine cells of the medulla. Alternatively, cellular extracts may be prepared from available cell lines, particularly cell lines of a neurological or endocrine origin. Cell lines contemplated herein include, but are not limited to, rat PC12 pheochromocytoma cells, AtT-20, GH3 and HIT cells.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with SV2 protein or fragment and other components of the assay under conditions in which association of the protein with the binding partner can occur, followed by the addition of LEV or an analog or derivative thereof. Alternatively, the LEV or an analog or derivative thereof may be added to the cellular extract before or at even time with the test agent or compound. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to SV2A can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

As discussed above, to aid in separating associated binding partner pairs from the mixed extract, the LBS can be immobilized on a solid support. For example, the LBS can be attached to a nitrocellulose matrix or acrylic beads. Attachment of the LBS to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. (Methods Mol. Biol. 69:171-184. (1997)) or Sauder et al. (J. Gen. Virol. 77:991-996. (1996)) or identified through the use of epitope tagged proteins or poly-His fusion or GST fusion proteins.

Alternatively, mammalian cell-based protein-protein assays utilizing bioluminescence or fluorescence energy transfer (BRET and FRET, respectively) and the yeast two-hybrid system may be a tool for the identification of protein-protein interactions.

Another approach to identifying pharmacologically active compounds that act via the SV2 proteins is by analyzing the effects of such compounds on wild-type and SV2 knockout cell lines, tissues, and animals. For example, compounds of interest, which might have previously been identified by testing in genomic wild-type animal or tissue models of disease, or by screening against functional cellular assays, can be re-tested in equivalent or informative assays in cells, tissues or animals that have reduced or low levels of functional SV2 proteins, or which lack functional SV2 proteins altogether. Such knockdowns or knockouts might be obtained, for example, by using anti-sense or RNAi techniques, or by working with genomic knockout animals.

In some embodiments, compounds that inhibit N-type calcium channels in neurons of wild-type animals are identified, followed by testing the compounds under the same conditions in neurons that have their SV2 proteins knocked down using RNAi or antisense oligos targeted to the SV2 mRNA sequences, or, alternately, neurons from genomic SV2 knockout animals. The lack of an effect in the SV2 knockout neurons would be evidence that the compounds are having their effect via SV2 proteins.

In another embodiment, compounds with anticonvulsant properties are identified by testing their ability to inhibit epileptiform field potentials recorded in the CA3 area of wild-type rat hippocampal slices bathed in an epileptogenic medium containing increased potassium and lowered calcium. Compounds that exhibit anticonvulsant properties could then be tested in the same assay using SV2 knockout or knockdown hippocampal slices. If a lack of efficacy was observed in the slices without SV2 protein expression, this would strongly support an effect mediated by interactions with SV2 proteins.

In another embodiment, the effect of compounds or agents which bind to the LBS on presynaptic divalent cation storage can be studied in knockout or knockdown mice. In a particular embodiment, wild-type and SV2 knockout or knockdown mice are administered an amount of the compound or agent which binds to the LBS. Animals are sacrificed and brains are immediately removed and flash-frozen. Elemental imaging of thin freeze-dried cryosections is carried out and the elemental composition of the presynaptic nerve terminals is determined by electron probe x-ray microanalysis and elemental imaging of characteristic x-rays. An example of such a method is disclosed by Andrews et al. (Proc. Natl. Acad. Sci. USA 84(6):1713-1717 (1987)).

IV. In Vitro Characterization of SV2

The invention includes the functional characterization of the SV2 family of proteins. In one embodiment, the invention includes the cloning and expression of both the rat and human forms of the SV2 proteins SV2A, SV2B, SV2C and the related synaptic vesicle protein SVOP. In another embodiment, the invention further includes identification of the domain or domains comprising the LBS. In an additional embodiment, the invention includes discovery of possible multiple functions of the SV2 proteins, and of the effect(s) of levetiracetam and related ligands on these functions.

In an additional embodiment, the invention includes expression of the SV2 protein in a eukaryotic host cell for study of function. The protein might be expressed in it's native form, or as fusions with fluorescent or other peptidic tags, including epitope and affinity tags; mutant forms, or fragments of the protein might be expressed and studied, fusions between the protein and homologous proteins might be expressed and studied. The heterologously expressed SV2 might be studied in-situ using electrophysiology, microscopy, or other techniques; or it might be expressed and purified in functional form from the eukaryotic using electrophysiology or other techniques.

In one particular embodiment, the SV2 protein, native or modified as above, might be expressed in a eukaryotic host and purified. The protein might be purified and incorporated into artificial lipid vesicles, or artificial bilayer membranes for study. Possible transport functions of the SV2 protein might be studied by biochemical means, for instance measuring radioactively labeled substrate transport into or out of the vesicles. Another possible approach is to use electrophysiology to study such transport in purified protein incorporated into synthetic vesicles or artificial lipid membranes.

In another particular embodiment, the invention includes the expression of the SV2 protein in a prokaryotic host, such as *E. coli*, and purification. In another particular embodiment, the invention includes the recombinant expression of the SV2 protein in a eukaryotic host, including yeast (*Saccharomyces cerevisie* or *Pichia pastoris*, for example), COS-7, HEK293 and PC12a cells, and purification. In accordance with the present invention, polynucleotide sequences that encode SV2 proteins, fragments of the polypeptide, fusion proteins or functional equivalents thereof may be used to generate recombinant DNA molecules that direct the expression of SV2 protein in appropriate host cells. Due to the inherent degeneracy of the genetic code, other DNA sequences that encode substantially the same or a functionally equivalent amino acid sequence may be used to clone and express SV2. As will be understood by those of skill in the art, it may be advantageous to produce SV2-encoding nucleotide sequences possessing non-naturally occurring codons. Codons preferred by a particular prokaryotic or eukaryotic host (Murray et al. Nuc. Acids Res. 17:477-508. (1989)) can be selected, for example, to increase the rate of SV2 expression or to produce recombinant RNA transcripts having desirable properties, such as a longer half-life, than transcripts produced from naturally occurring sequence.

In another embodiment, SV2 proteins of the invention are recombinantly co-expressed in host cells with other proteins SV2 is normally associated with in synaptic vesicles. In a preferred embodiment, SV2 proteins are co-expressed with SNARE complex proteins including vesicle-associated VAMP/synaptobrevin, syntaxin and SNAP-25. In a preferred embodiment, SV2A is recombinantly co-expressed in a host cell with recombinantly expressed synaptotagmin.

In another embodiment, the roles of glycosylation, phosphorylation and other natural or introduced protein modifications in SV2 protein function, stability and interaction are analyzed. Nucleotide sequences encoding SV2 proteins of the present invention can be engineered using methods generally known in the art in order to alter sequences encoding SV2 proteins for a variety of reasons, including but not limited to; alterations which modify the cloning, processing, and/or expression of the gene product; alterations which modify the interaction of SV2 proteins with binding partners; alterations of the solubility and/or membrane insertion of SV2 proteins; and alterations which affect the LBS and its association with ligands. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

Upon exocytosis at the synapse, vesicles cluster at the pre-synaptic plasma membrane and fuse in response to increased $Ca^{2+}$ levels. Upon $Ca^{2+}$ accumulation within the synapse, the binding of synaptotagmin to SV2A is inhibited and dimerization of two synaptotagmin $Ca^{2+}$-binding domains (C2B) is stimulated, which may play a role in organizing the SNARE complex and promoting fusion. At low $Ca^{2+}$, the fusion of vesicles is inhibited because SV2A is still attached to the synaptotagmin complex. Binding of synaptotagmin to other proteins, including the ATPase VCP, the SNARE protein SNAP-25 and syntaxin, is $Ca^{2+}$-dependent (Augustine, 2001). In order to shed light on this exocytosis mechanism and define more precisely the role of SV2A in the fusion process, changes in protein levels within these complexes in response to modulation of the LBS are assayed. In particular embodiments, the ability of LBS ligands to modulate the interactions between SV2A and the synaptotagmin-SNARE complex and to assess which stage of the complex assembly and which partners are modulated by the binding to SV2A of LEV, analogs or derivatives thereof, or compounds or agents which compete with LEV for binding to the LBS. In one such embodiment, protein stoichiometry in the complex after ligand addition is analyzed using antibodies specific for the identified SV2A partners and a combination of immuno-precipitation and recombinant GST-fusion protein affinity chromatography.

In another such embodiment, mass spectrometry and/or surface plasmon resonance are used to detect the effects of LBS ligands on the interactions between SV2A and its partner (e.g. synaptotagmin) or short peptides derived from binding domains. In another particular embodiment, biochemical approaches are used to demonstrate if LBS ligands compete with bivalents (such as $Ca^{2+}$, $Pb^{2+}$, $Zn^{2+}$) and inhibit their interactions with SV2A and/or synaptotagmin. In another particular embodiment, the role of the SV2 proteins in synaptic vesicle fusion and recycling is analyzed by the creation of PC 12a cell lines, primary neuronal cultures, chromaffin cells and other cell lines or primary isolates expressing fusion constructs between the SV2 proteins and GFP. In one such embodiment, these cell lines are analyzed by fluorescence microscopy tracking of SV2 complexes and synaptic vesicle exocytosis and trafficking, and the effects of treatments with LBS ligands on these events. The cell types described above can also be used to measure vesicle fusion and exocytosis (using encapsulated dye into the vesicles or measuring the release of labeled neurotransmitters) and the ability of LBS ligands to modulate these activities.

In other embodiments of characterizing SV2 proteins and its binding partners, enrichment of the entire multi-protein complex is achieved by affinity-based methods using GST-fusion SV2 or anti-SV2 antibodies. In a particular embodiment, SV2A is overexpressed in PC12 cells with a GST tag and, together with its partners, immunoprecipitated by an antibody against the tag. In a related embodiment, SV2A is immobilized onto agarose beads using a GST or poly-histidine tag. In a preferred embodiment, synaptic vesicle extracts, cell extracts or brain extracts are incubated with the beads, SV2A is cleaved off and eluted proteins are resolved by 1D or 2D gels and analyzed. In a further embodiment, identification of these proteins is used to search databases for novel putative interacting partners. In another embodiment, the yeast two-hybrid (Y2H) system or mammalian cell-based protein-protein assays are used for the identification of protein-protein interactions within living organisms to confirm SV2 binding partners found by the affinity-based methods and to define the specific protein domain interactions using known cDNAs.

Antibodies specific for SV2 proteins may be produced by inoculation of an appropriate animal with the polypeptide or an antigenic fragment. Antibodies specific for the LBS may be produced by inoculation with full-length SV2 protein or a fragment comprising the LBS. An antibody is specific for the particular SV2 if it is produced against an epitope of the polypeptide and binds to at least part of the natural or recombinant protein. Monoclonal and/or polyclonal antibodies specific for SV2 or for the LBS may be produced by any of a number of methods which are well known in the art for antibody production, such as those taught by Harlow and Lane (Antibodies: A Laboratory Manual. Cold Spring Harbor Laboratory, Cold Spring Harbor, N.Y. (1988)). SV2 peptides for antibody induction do not require biological activity; however peptides must be immunogenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of SV2 amino acids may be fused with those of another protein such as keyhole limpet hemocyanin and antibody produced against the chimeric molecule. Antibody production includes not only the stimulation of an immune response by injection into animals, but also analogous steps in the production of synthetic antibodies or other specific-binding molecules such as the screening of recombinant immunoglobulin libraries (see e.g. Orlandi et al. Proc. Nat. Acad. Sci. USA 86:3833-3837. (1989); Huse et al. Science 256:1275-1281. (1989)) or the in vitro stimulation of lymphocyte populations. Current technology (Winter G. and Milstein C. (1991) Nature 349:293-299) provides for a number of highly specific binding reagents based on the principles of antibody formation. These techniques may be adapted to produce molecules specifically binding SV2 or the LBS.

In a particular embodiment, the present invention includes the human SV2C protein of SEQ ID NO: 6 and the nucleic acid molecule encoding it (SEQ ID NO: 5), as well as allelic variants and functional equivalents thereof. The invention further includes identification of the in vivo distribution of the SV2C protein, including, but not limited to, within the central nervous system, peripheral nervous system and endocrine cells and tissues. The invention further includes identification of ligands and/or binding partners of the SV2C protein. The invention further includes elucidation of the function of the SV2C protein.

V. SV2 Expression in Disease

The invention includes elucidating the expression of SV2 proteins in relation to specific neurological diseases. In a particular embodiment, antibodies specific for SV2A are used to probe brain tissue in a regional specific manner within the brain, spinal cord and neuroendocrine tissues or cells such as chromaffin cells of control animals and animals mimicking epilepsy, epileptogenesis, Parkinson's disease and cognition deficits, other CNS disorders (see above) and endocrinopathy and adrenal medulla-related diseases. In another embodiment, the invention includes the elucidation of the relationship of all SV2 protein isoforms to the pathologies described above, including alterations or switching of isoforms. In a preferred embodiment DNA microarrays are probed for the expression of SV2 protein coding sequences, and changes thereof, in relation to different neurological diseases. An example of using DNA microarrays for determining expression of a particular nucleic acid sequence can be found in U.S. Pat. No. 5,900,882. In another preferred embodiment, changes in regional or global SV2 protein expression in relation to a neurological disorder associated with synaptic vesicle function is validated by quantitative PCR (qPCR).

In another embodiment, knockout mice are analyzed for the presence of the LBS. In a preferred embodiment, purified synaptic vesicles from mice with the lethal SV2A knockout phenotype, SV2B or double KO SV2A/B are purified and analyzed for the presence of the LBS and for substrate and/or ion uptake in comparison with synaptic vesicles from wild-type mice.

In a particular embodiment, comparisons are made of protein expression levels in synaptic vesicles purified from healthy and diseased animals including, but not limited to, pathologies described above, for example, for protein mapping of synaptic vesicles for the detection of disease-related proteins. In a particular embodiment, comparison of 1D and/or 2D gels of synaptic vesicles derived from the healthy and the diseased states are used to identify proteins that are up- or down-regulated in a disease-specific manner. In another embodiment, targets are identified by comparison of the proteome of synaptic vesicles from wild-type with that of SV2 knock-out mice or double-stranded RNA-induced interference (RNAi; Krichevsky et al., Proc. Nat. Acad. Sci. USA 99(18):11926-11929. (2002)) cultured neurons. In another embodiment, the invention includes performing RNAi or antisense nucleotides in primary neuronal cultures, cultured neurons or PC12 cells to inhibit or eliminate SV2 expression.

VI. Determination of the LBS Location on the SV2 Protein

A number of methods are employed in the determination of the location of the LBS. The LBS may be comprised of a contiguous segment of amino acid residues, or it may be a 3 dimensional structure comprised of amino acid sequences present on one or more extracellular or intracellular loops or domains. In addition, the LBS may be dependent upon the glycosylation of the SV2 protein or may not require glycosylation of the SV2 protein.

In a particular embodiment, radioligands are used to specifically photoaffinity-label the LBS. In a particular embodiment, the site of covalent attachment of the radioligand is determined by purifying and sequencing the proteolytic fragment from photoaffinity labeled synaptic vesicles with SV2A-antibody affinity chromatography or immunoprecipitation and mass spectrometry.

In particular embodiments for the identification of protein domains involved in the interactions between LBS ligands and the SV2A protein fragments of SV2 proteins, or SV2 proteins with amino acid deletions, additions or substitutions are analyzed for effects on binding. In a preferred embodiment, selected residues will be modified by site directed mutagenesis of the cDNA. In another embodiment, domains are exchanged between SV2 isoforms and structural features of isoforms that are important for ligand recognition are identified. In an example of this embodiment, the N-terminal domain of SV2A is replaced with the shorter equivalent region of SV2B to determine the effect on LBS ligand binding. In another example of this embodiment, a series of swaps are made between regions of SV2A and regions of SVOP, to determine the effect on ligand binding. Such swaps might include large regions of each protein, containing for example, multiple transmembrane regions, as well as small regions of the protein, including for example individual transmembrane regions.

In another embodiment, the three-dimensional structure of the SV2 protein (or selected binding domains) is analyzed using NMR spectroscopy or x-ray crystallography or circular dichroism or infrared spectroscopy utilizing pure SV2A with at least binding activity maintained for the revelation of resolution of the topology of LBS sites and design of new drugs to fit that receptor. If the binding domain upon investigation requires an hydrophobic environment then the protein must be solubilized in a detergent such as dodecylmaltoside or derivatives (see Examples). Purified protein can be crystallized by methods known in the art, for example, by methods disclosed by A. McPherson in "Preparation and Analysis of Protein Crystals" (John Wiley and Sons, New York, (1982)). Alternatively, SV2 proteins of the present invention may also be crystallized by vapor diffusion and vapor diffusion apparati used in the art may be readily employed in the processes of the present invention. Such apparati are disclosed in, for example, U.S. Pat. Nos. 4,886,646; 5,096,676; 5,130,105; 5,221,410 and 5,400,741, the disclosure of which are herein incorporated by reference. X-ray crystallography determination of SV2 protein structure as well as its association with ligands and/or binding partners can be performed using methods and imaging systems as disclosed in U.S. Pat. No. 5,978,444, for example.

In some embodiments, SV2 proteins, including isoforms SV2A, SV2B are SV2C, are recombinantly expressed in host cell lines to screen a diverse set of compounds or agents in binding assays for each isoform. Compounds or agents that interact with the SV2A isoform are analyzed for interaction with other SV2 isoforms. In another embodiment, binding experiments are performed to test several reference drugs, AEDs, steroids and to compare the kinetics of binding between native LBS, human and rat recombinant SV2A.

VII. Uses for Agents on the Invention

The invention includes the use of the compounds or agents identified by methods of the invention for the modulation of SV2 protein. Compounds or agents of the invention can be used to modulate synaptic vesicle function; in particular to modulate disorders associated with synaptic vesicle function, or disorders which might be improved by affecting some aspect of synaptic vesicle function, or also to modulate synaptic vesicle function in order to correct disorders of pre-synaptic function, or disorders of neuronal signaling that can be fixed by compensatory changes in synaptic vesicle function. As used herein, a compound or agent is said to modulate synaptic vesicle function if it is capable of up- or down-regulating at least one function of at least one component of a synaptic vesicle, or the pre-synaptic systems which synaptic vesicles interact with.

In a preferred embodiment, the agent or compound is LEV or an analog or derivative thereof. In another preferred embodiment, the compound or agent binds to the levetiracetam binding site of an SV2 protein. In still another preferred embodiment, the compound or agent competes with levetiracetam or an analog or derivative thereof for binding to the levetiracetam binding site. In yet another preferred embodiment, agents of the invention for the treatment of neurological disorders include N-alkylated 2-oxo-pyrrolidine derivatives, N-alkylated 2-oxo-piperidinyl derivatives, and N-alkylated 2-oxo-azepanyl derivatives as described above.

In a preferred embodiment, the compound or agent is an anti-SV2 antibody or fragment thereof, including those that bind to the levetiracetam binding site of SV2 protein and may be a polyclonal antibody or a monoclonal antibody. In related preferred embodiments, the antibody fragment is an Fab fragment, Fab' fragment, $F(ab')_2$ fragment or an scFv fragment, whereas the monoclonal antibody is a chimeric antibody, humanized antibody, or a human antibody.

In a preferred embodiment, the invention includes the modulation at least one function or activity of a SV2 protein in a cell, for example, by exposing the cell to a compound or agent that binds to the levetiracetam binding site of the SV2 protein. In particular embodiments, modulation at least one function or activity of a SV2 protein in a cell includes exposure of the cell to the compound or agent in vitro, in vivo, in situ and ex vivo. As used herein, modulation of a function of SV2 includes, but is not limited to modulation of the transport of ions or other natural substrates across the membrane of the synaptic vesicle, modulation of the binding of an SV2 protein to a natural ligand thereof, modulation of the binding of an SV2 protein to a binding partner as described above, and remodulation of synaptic vesicle formation, fusion, regulation or function.

In a preferred embodiment, the modulation of SV2 protein in a cell includes modulating synaptic vesicle function in the cell. As used herein, synaptic vesicle functions which may be modulated by compounds or agents identified by the methods of the invention include, but are not limited to, formation of synaptic vesicles in the presynaptic neuron, fusion of synaptic vesicles with other synaptic vesicles or the synaptic membrane, recycling or turnover of synaptic vesicles, association of synaptic vesicles with the presynaptic grid, and neurotransmitter release, association with proteins from the extracellular matrix (laminin-1, etc.) and post-synaptic densities.

In particular embodiments, exposure of the cell to a compound or agent of the invention which modulates at least one function or activity of a SV2 protein in a cell is carried out under conditions where the concentration of monovalent and/or divalent cations in the environment of the cell is controlled. In preferred embodiments, the divalent cation is at least one of $Ca^{2+}$, $Zn^{2+}$, $Pb^{2+}$, $Mg^{2+}$, $Mn^{2+}$, $Fe^{2+}$ and $Cu^{2+}$. In preferred embodiments, the monovalent cation is $K^+$. In a particular embodiment, exposing the cell to a compound or agent which binds to the levetiracetam binding site is carried out under conditions with a low monovalent and/or divalent cation concentration, or less than about 1 μM. In another particular embodiment, exposing the cell to a compound or agent which binds to the levetiracetam binding site is carried out under conditions with a physiological monovalent and/or divalent cation concentration, or between about 1 μM and about 1000 μM. In yet another particular embodiment, exposing the cell to a compound or agent which binds to the levetiracetam binding site is carried out under conditions with a high monovalent and/or divalent cation concentration, or more than at least about 1000 μM.

VIII. Treatment of Neurological Disorders

Compounds or agents identified by the methods of the invention can be used in an effective amount to treat neurological disorders associated with synaptic vesicle function. In a particular embodiment, treatment with the compound or agent modulates a neurological disorder. In a preferred embodiment, the neurological disorder is a seizure disorder. In another preferred embodiment, the neurological disorder is selected from the group consisting of Parkinson's disease, Parkinson's dyskinesias, migraine, Alzheimer's disease, neuropathic pain, essential tremor, and cognitive disorders. In a highly preferred embodiment, the neurological disorder is epilepsy. In another highly preferred embodiment, treatment with the compound or agent enhances cognitive function.

In a preferred embodiment, the agent or compound is LEV or an analog or derivative thereof. In another preferred embodiment, the compound or agent binds to the levetiracetam binding site of an SV2 protein. In still another preferred embodiment, the compound or agent competes with levetiracetam or an analog or derivative thereof for binding to the levetiracetam binding site. In yet another preferred embodiment, agents of the invention for the treatment of neurological disorders include N-alkylated 2-oxo-pyrrolidine derivatives, N-alkylated 2-oxo-piperidinyl derivatives, and N-alkylated 2-oxo-azepanyl derivatives as described above.

In a preferred embodiment, the compound or agent is an anti-SV2 antibody or fragment thereof, including those that bind to the levetiracetam binding site of SV2 protein and may be a polyclonal antibody or a monoclonal antibody. In related preferred embodiments, the antibody fragment is an Fab fragment, Fab' fragment, $F(ab')_2$ fragment or an scFv fragment, whereas the monoclonal antibody is a chimeric antibody, humanized antibody, or a human antibody.

As used herein, a subject can be any mammal, so long as the mammal is in need of modulation of function or activity of a SV2 protein mediated by a compound or agent identifiable by a method of the invention. The term mammal is defined as an individual belonging to the class Mammalia. The invention is particularly useful in the treatment of human subjects.

As used herein, an "effective amount" is an amount of a substance, compound or agent which is effective to inhibit, reduce, ameliorate, modulate or control at least one symptom or effect of a disease, condition or another administered substance, compound or agent either in vivo, ex vivo, or in vitro. Further as used herein, an "effective amount" is an amount of a substance, compound or agent which is effective to enhance at least one cognitive function in vivo.

As used herein, an agent is said to modulate a neurological disorder when the agent reduces the degree or severity of at least one symptom the neurological disorder. For instance, seizures in epilepsy may be prevented; the amplitude, magnitude or severity of seizures may be reduced, or the frequency of the occurrence of seizures may be reduced by the administration of compounds or agents which up- or downregulate or modulate in some way the expression or at least one activity of a SV2 protein of the invention.

The compounds or agents identified by the methods of the present invention can be provided alone, or in combination with other compounds or agents that modulate a particular pathological process. For example, a compound or agent of the present invention can be administered in combination with other known drugs. As used herein, two agents are said to be administered in combination when the two agents are administered simultaneously or are administered independently in a fashion such that the agents will act at the same time. In a particular embodiment of the invention, the compounds or agents identified by the methods of the present invention can be provided in combination with compounds or agents that modulate GABAergic pathways in the brain. In another embodiment, the compounds of the invention are administrated together with amantadine for combined treatment of L-DOPA and tardive dyskinesia.

The compounds or agents of the present invention can be administered via parenteral, subcutaneous, intravenous, intramuscular, intraperitoneal, epidural, transdermal, topical, or mucosal routes, or combinations thereof. The dosage administered will be dependent upon the age, health, and weight of the recipient, kind of concurrent treatment, if any, frequency of treatment, and the nature of the effect desired. Drug solubility and the site of absorption are factors which should be considered when choosing the route of administration of a therapeutic agent.

The present invention further includes compositions containing one or more compounds or agents which modulate expression or at least one activity of a SV2 protein of the invention. While individual needs vary, determination of optimal ranges of effective amounts of each component is within the skill of the art. Typical dosages comprise about 0.1 to about 100 mg/kg body weight. The preferred dosages comprise about 5 to about 80 mg/kg body weight. More preferred dosages comprise about 10 to about 60 mg/kg body weight. The most preferred dosages comprise about 20 to about 40 mg/kg body weight.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

The compounds or agents may be formulated for parenteral administration by injection, e.g., by bolus injection or continuous infusion. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Liposomes can also be used to encapsulate the agent for delivery into the cell. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Mucosal routes of administration include, but are not limited to, oral, rectal and nasal administration. Preparations for mucosal administrations are suitable in various formulations. If the compound or agent is water-soluble, then it may be formulated in an appropriate buffer, for example, phosphate buffered saline or other physiologically compatible solutions, preferably sterile. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, or rectal administration or, in the case of tumors, directly injected into a solid tumor. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystallina cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Preparations for oral administration may be suitably formulated to give controlled release of the active compound.

For buccal administration, the compositions may take the form of tablets or lozenges formulated in conventional manner.

The compounds or agents may also be formulated in rectal compositions such as suppositories or retention enemas, e.g., containing conventional suppository bases such as cocoa butter or other glycerides.

In addition to the formulations described previously, the compounds or agents may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

In practicing the methods of this invention, the compounds or agents of this invention may be used alone or in combination, or in combination with other therapeutic or diagnostic agents. In certain preferred embodiments, the compounds of this invention may be co-administered along with other compounds or agents typically prescribed for these conditions according to generally accepted medical practice such as anticonvulsives. The compounds of this invention can be utilized in vivo, ordinarily in mammals, such as humans, sheep, horses, cattle, pigs, dogs, cats, rats and mice, or in vitro.

IX. Gene Therapy

SV2 proteins used in treatment can be generated endogenously in the subject, in treatment modalities often referred to as "gene therapy." In a specific embodiment, nucleic acids comprising sequences encoding SV2 proteins or functional derivatives thereof, are administered to treat, inhibit or prevent a neurological disease or disorder associated with aberrant synaptic function, by way of gene therapy. Gene therapy refers to therapy performed by the administration to a subject of an expressed or expressible nucleic acid. In this embodiment of the invention, the nucleic acids produce their encoded SV2 protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505. (1993); Wu and Wu, Biotherapy 3:87-95. (1991); Tolstoshev, Ann. Rev. Pharmacol. Toxicol. 32:573-596. (1993); Mulligan, Science 260:926-932. (1993); and Morgan and Anderson, Ann. Rev. Biochem. 62:191-217. (1993); TIBTECH11(5):155-215. (1993)). Methods commonly known in the art of recombinant DNA technology which can be used are described in Ausubel et al., eds., Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an SV2 protein, said nucleic acid sequences being part of expression vectors that express the SV2 protein or fragments or chimeric proteins thereof in a suitable host. In particular, such nucleic acid sequences have promoters operably linked to the SV2 protein coding region, said promoter being inducible or constitutive, and, optionally, tissue-specific. In another particular embodiment, nucleic acid molecules are used in which the SV2 protein coding sequences and any other desired sequences are flanked by regions that promote homologous recombination at a desired site in the genome, thus providing for intrachromosomal expression of the antibody nucleic acids (Koller et al., Proc. Natl. Acad. Sci. USA 86:8932-8935. (1989); Zijlstra et al., Nature 342:435-438. (1989)).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, gene therapy vectors can be delivered in vivo to a subject by, for example, intravenous injection, local administration (see U.S. Pat. No. 5,328,470) or by stereotactic injection (see e.g., Chen et al. Proc. Natl. Acad. Sci. USA 91:3054-3057. (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Direct administration of the nucleic acid sequences for expression of encoded SV2 protein in vivo can be accomplished by any of numerous methods known in the art, e.g., by constructing them as part of an appropriate nucleic acid expression vector and administering them so that they become intracellular, e.g., by infection using defective or attenuated retroviral vectors or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu et al., J. Biol. Chem. 262:4429-4432. (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16,1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller et al., Proc. Natl. Acad. Sci. USA 86:8932-8935. (1989); Zijlstra et al., Nature 342:435-438. (1989)).

In a specific embodiment, viral vectors that contain nucleic acid sequences encoding an SV2 protein of the invention are used. For example, a retroviral vector can be used (see Miller et al., Meth. Enzymol. 217:581-599. (1993)). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al. (Biotherapy 6:291-302. (1994)), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651. (1994); Kiem et al., Blood 83:1467-1473. (1994); Salmons et al., Human Gene Therapy 4:129-141. (1993); and Grossman et al., Curr. Opin. in Genetics and Devel. 3:110-114. (1993).

Adenoviruses are other viral vectors that can be used in gene therapy. In a preferred embodiment, adenovirus vectors are used. Adenoviruses have the advantage of being capable of infecting non-dividing cells. Kozarsky et al., Current Opinion in Genetics and Development 3:499-503. (1993) present a review of adenovirus-based gene therapy. Bout et al., Human Gene Therapy 5:3-10. (1994) demonstrated the use of adenovirus vectors to transfer genes to the respiratory epithelia of rhesus monkeys. Other instances of the use of adenoviruses in gene therapy can be found in Rosenfeld et al., Science 252:431-434. (1991); Rosenfeld et al., Cell 68:143-155. (1992); Mastrangeli et al., J. Clin. Invest. 91:225-234. (1993); PCT Publication WO 94/12649; and Wang, et al., Gene Therapy 2:775-783. (1995).

Adeno-associated virus (AAV) has also been proposed for use in gene therapy (Walsh et al., Proc. Soc. Exp. Biol. Med. 204:289-300. (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618. (1993); Cohen et al., Meth. Enzymol. 217:618-644. (1993); Cline, Pharmac. Ther. 29:69-92. (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, endocrine cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cells used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, Cell 71:973-985. (1992); Rheinwald, Meth. Cell Biol. 21A:229. (1980); and Pittelkow and Scott, Mayo Clinic Proc. 61:771. (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

X. Uses for Biotinylated Ligands

The present invention provides nonradioactive labelled SV2A/LBS ligands containing a biotin tag. Such biotinylated ligands are useful in screening assays with no radioactive waste and higher throughput.

As an example, biotinylated derivatives of SV2A/LBS ligands can be used in screening assays (e.g. binding) with native brain membranes or SV2 expressed in cell lines for the discovery of more potent structures. The amount of biotin tag bound to SV2A can be quantified using streptavidin-fluorescein or avidin derivatives.

Biotinylated ligands are also useful for assessing the conformational state of SV2 after solubilization, immunoaffinity purification, and chromatography.

Moreover, the present invention provides photoactivable versions of the ligands for labeling and detection in biological samples. The photoactivable biotinylated ligands may also be used to localize and purify SV2 from tissues, isolated cells, subcellular fractions and membranes. The photoactivable biotinylated ligands could also be used for SV2 cross-linking and identification of binding domains of LBS ligands.

XII. Solubilizing SV2 and Affinity Purification

The present invention provides a method for solubilizing SV2/LBS proteins comprising treating membranes with a detergent. The membrane proteins solubilized by the present method remain active as evaluated by binding assays and protein-protein interaction studies.

Briefly, the method comprised incubating membranes, as an example rat brain membranes, in solubilization buffer containing the detergent n-dodecyl-β-D-maltoside for about two hours at about 4° C. The incubated solution was subsequently centrifuged to collect the soluble SV2 protein, specifically the SV2A protein, from the supernatant. Presence of the soluble SV2A protein in the supernatant was confirmed by western blot analysis using anti-SV2A antibodies. The binding activity of the soluble SV2A protein in the supernatant was determined through binding experiments with ligands known to bind SV2A, such as levetiracetam and ucb 30889.

Other detergents such as the analogs of n-dodecyl-β-D-maltoside, for example, n-octyl, n-nonyl, n-decyl, n-undecyl-β-D-maltoside could also be used. In fact, preliminary data confirmed that the soluble protein obtained from solubilizing membranes with these detergents retains its binding activity.

The present invention also provides a method of affinity purification of the soluble SV2 protein and identification of putative SV2A partners. Briefly, affinity purification comprised incubating the supernatants from the solubilized membranes with anti-SV2A antibodies overnight at about 4° C. The mixture was then incubated by rotation with protein A-Sepharose beads in buffer for about an hour at about 4° C. The resin was washed several times with an appropriate buffer and the fractions containing the immunopurified SV2Aprotein were collected.

Figure 22A:
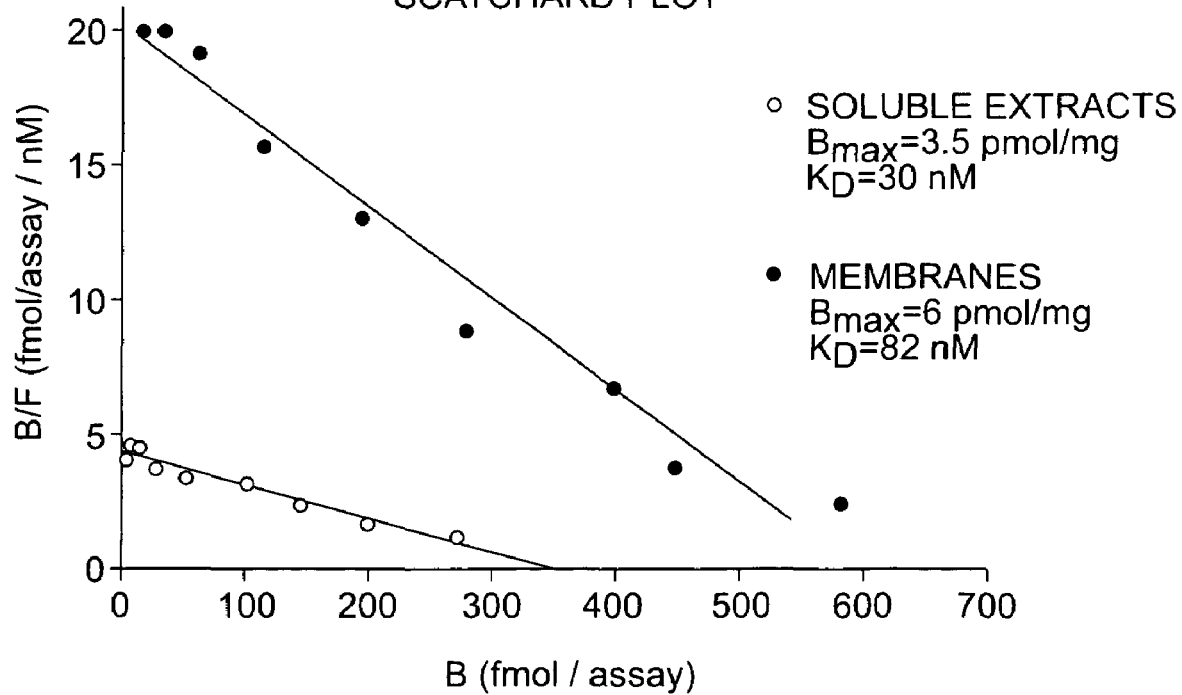
FIGS. 22(*a* and *b*) depicts identification of SV2A partners. Western blot analysis show synaptotagmin associated to soluble SV2A in the immunopurified fractions of the supernatants from solubilized rat brain membranes. The isoform SV2B was not detected.
Figure 22B:
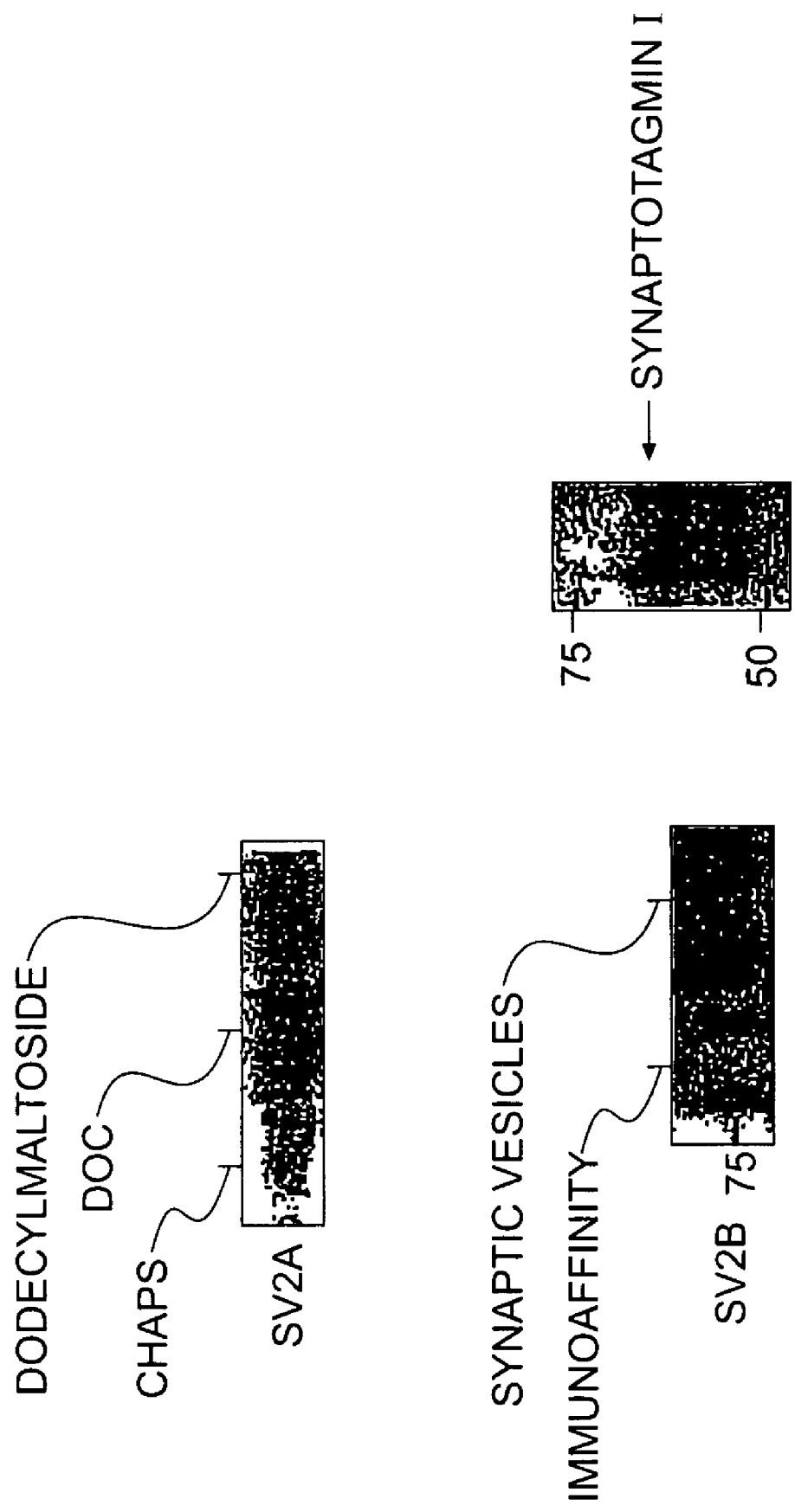

To detect the presence of binding partners of SV2A after affinity purification, a western blot analysis of the immunopurified fractions was performed to detect the presence of synaptotagmin (FIG. 22)

The present invention provides a method to purify a membrane-associated protein comprising solubilizing a membrane sample containing the protein with a detergent to form a solubilized complex and isolating the solubilized complex in a functional form. The detergent could be n-dodecyl-β-D-maltoside or derivatives thereof. The protein can then be isolated using an immunoaffinity technique.

The protein purified by the present method can be used to perform structural studies on the protein such as NMR, X-ray crystallography, Infrared spectroscopy, Circular dichroism and other methods well known in the art. The present invention also provides a method of performing SV2 protein interaction studies and for detecting peptides, molecules, and compounds that inhibit or promote the interactions between SV2 and a putative partner. The present invention can be used to identify SV2 binding partners.

The present invention could be used to solubilize SV2A, SV2B and SV2C membrane associated proteins and to affinity purify them for structural studies and for identifying binding partners.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Development of a Levetiracetam Analog for Binding Studies

LEV has been shown to bind to a specific binding site located preferentially in the brain (levetiracetam binding site or LBS : Noyer et al., Euro. J. Pharmacol. 286:137-146. (1995); Gillard et al. 2003)). However, [$^3$H]LEV displayed only micromolar affinity for this site, making it unsuitable for in depth characterization. This example describes the binding properties of [$^3$H]ucb 30889, (2S)-2-[4-(3-azidophenyl)-2-oxopyrrolidin-1-yl]butanamide, an analogue of levetiracetam. Binding experiments were conducted on crude rat brain membranes at 4° C. as described in Noyer et al. (Euro. J. Pharmacol. 286: 137-146 (1995)). Incubation time for equilibrium studies was 120 min. For kinetic and competition studies, [$^3$H]ucb 30889 (30 Ci/mmol) was used at a concentration of 1.3 nM in 0.5 ml of a Tris-HCl (pH 7.4) buffer containing 2 mM $Mg^{2+}$. Localization of the LBS in brain substructures was assessed by autoradiography on 25 μm thick slices incubated under similar conditions. Slides were then washed twice for 10 min at 4° C. in 50 mM Tris-HCl (pH 7.4) containing 0.5% BSA, dried and exposed for 3 weeks to [$^3$H]Hyperfilm at −20° C. Non-specific binding (NSB) was determined by the inclusion of 1 mM LEV during the incubation period.

FIG. 1 shows that [$^3$H]ucb 30889 binds reversibly to LBS in rat brain cortex. Binding kinetics were biphasic: half-times for association and dissociation were respectively, 3±2 min and 4±1 min for the fast component (25 to 50% of the sites), and 47±13 min an 61±15 min for the slow component. At 25° C., kinetics increased dramatically and only one component remained.

Figure 2:
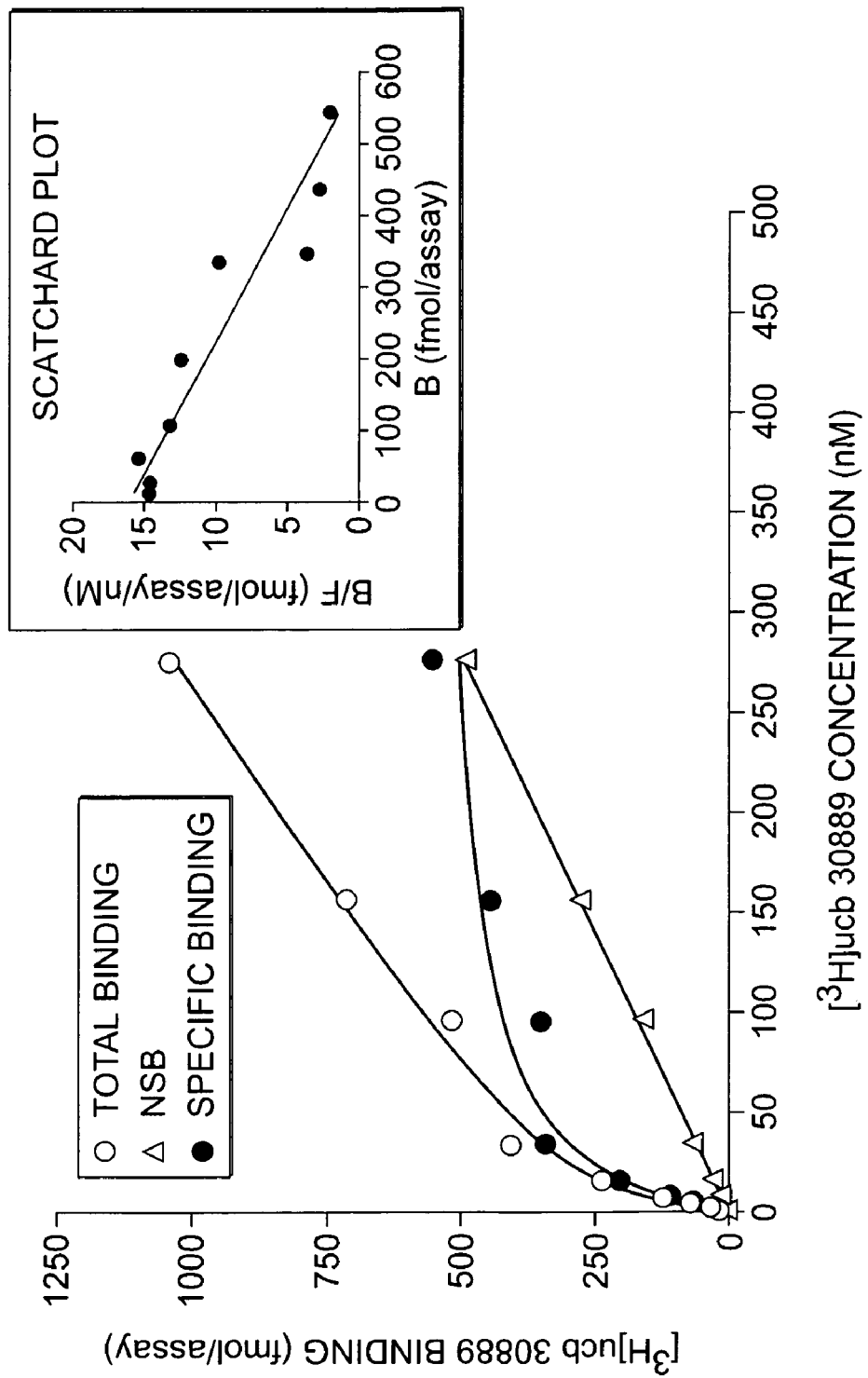
FIG. 2 depicts the saturation binding curves of ucb 30889.

FIG. 2 shows that the saturation binding curves of [$^3$H]ucb 30889 were compatible with the labeling of a homogeneous population of binding sites. $K_D$ and $B_{max}$ were respectively 42±10 nM and 5054±704 fmol/mg protein. The $B_{max}$ being similar to the value estimated using [$^3$H]levetiracetam as radioligand in similar membrane preparations (4718±413 fmol/mg protein).

Figure 3:
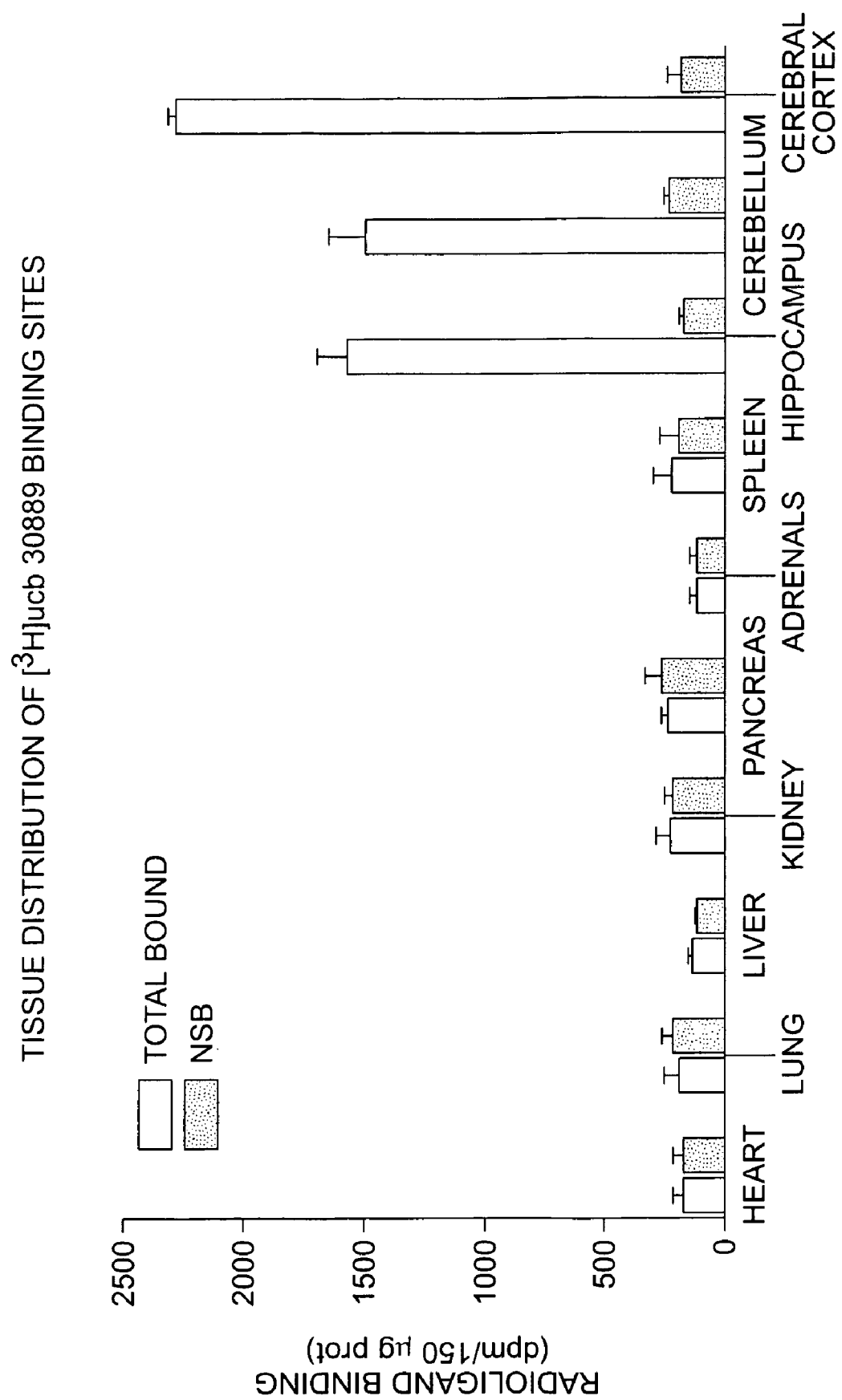
FIG. 3 shows that specific binding could not be detected in the peripheral tissues.

Specific binding could not be detected in the peripheral tissues examined (FIG. 3). The limit of detection under the experimental conditions (150 μg of protein/assay and 1.3 nM of radioligand) was a $B_{max}$ of 200 fmol/mg protein. This suggests that there are at least 25 times more binding sites in the cerebral cortex compared to the periphery.

Figure 4:
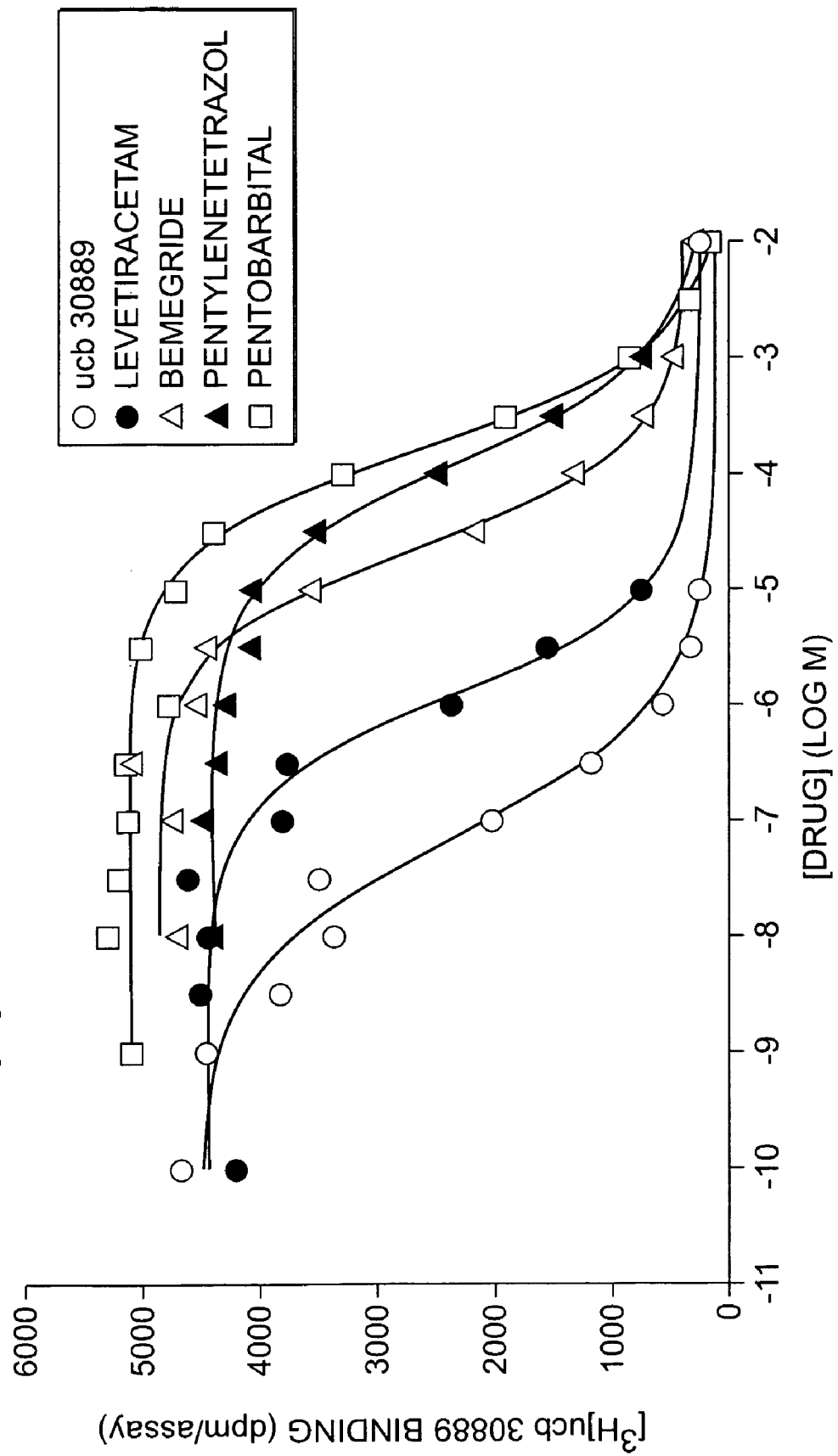
FIG. 4 depicts competition binding curves showing that ucb 30889 binds to LBS with about 10 fold higher affinity than LEV.
Figure 5:
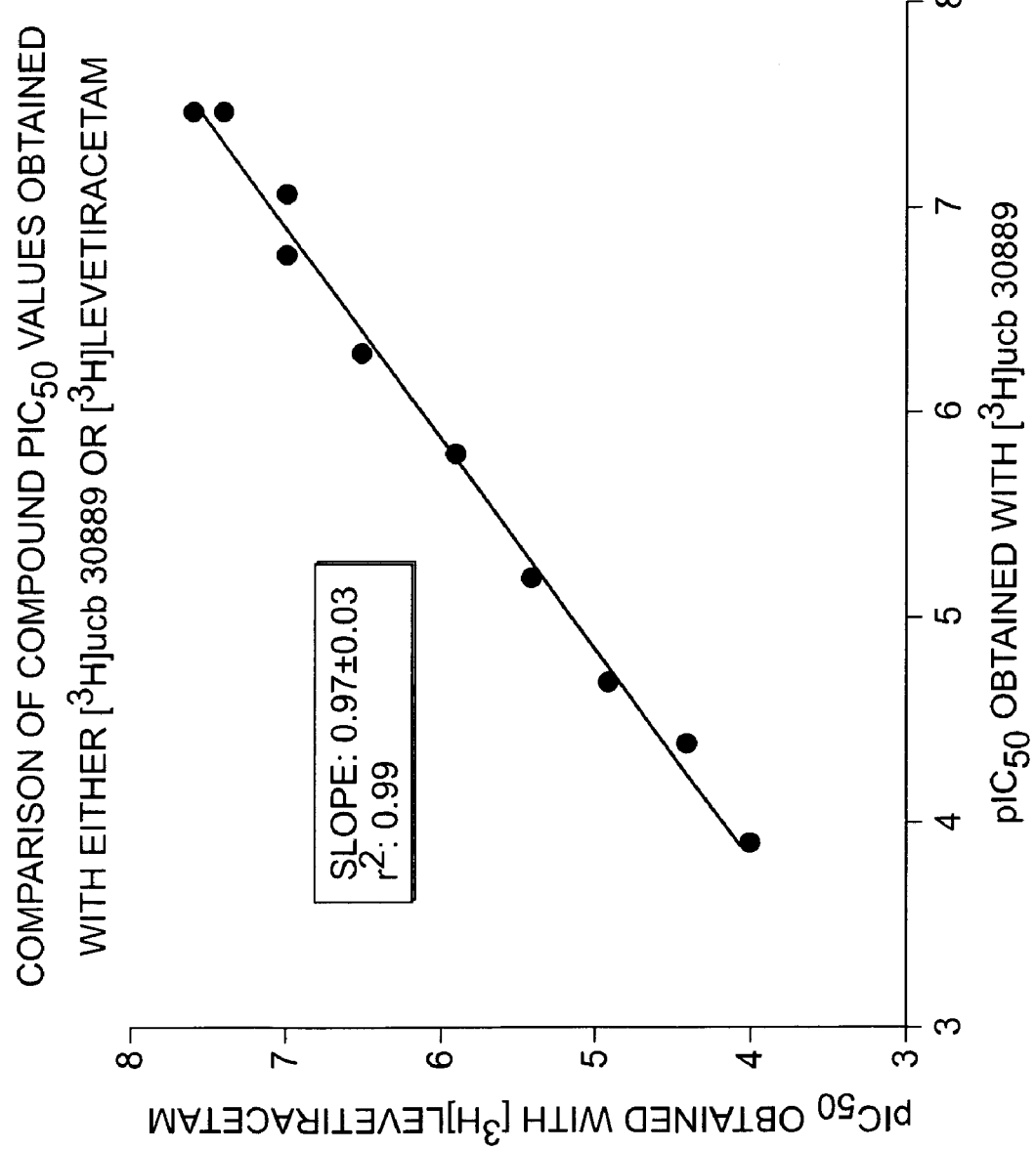
FIG. 5 depicts $pIC_{50}$ values for ucb 30889 versus levetiracetam.
Figure 7A:
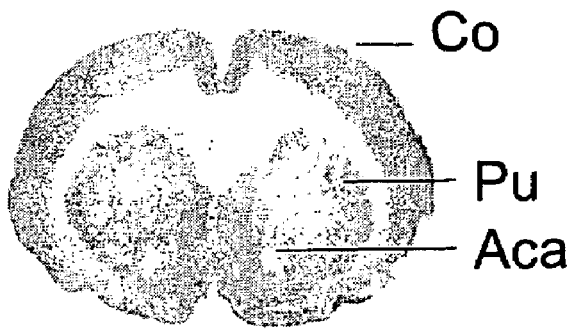
FIG. 7(a-f) depicts autoradiography of [$^3$H]ucb 30889 binding to coronal sections of rat brain.
Figure 7B:
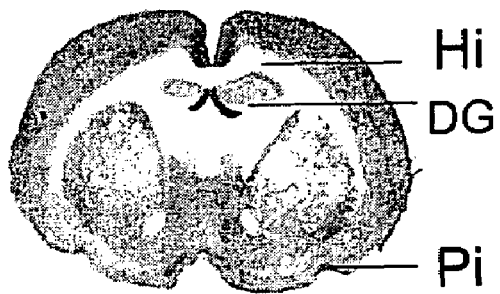
Figure 7C:
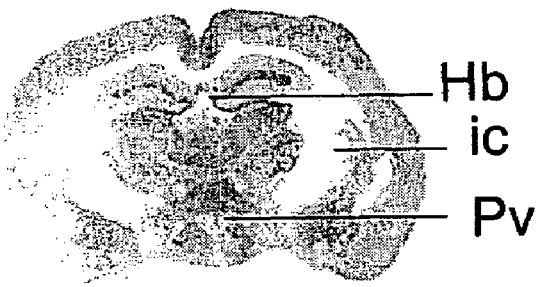
Figure 7D:
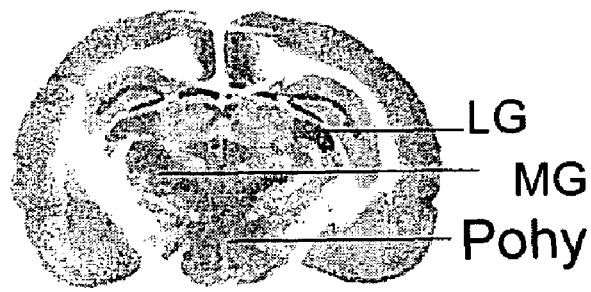
Figure 7E:
Figure 7F:
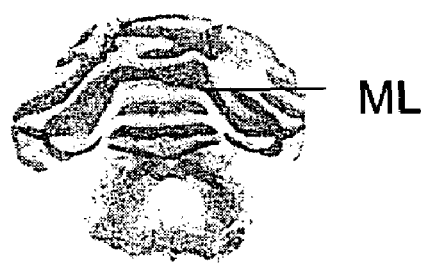
Figure 8A:
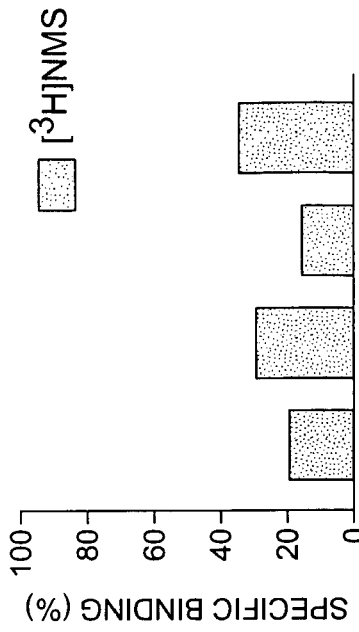
FIG. 8(a-d) depicts the subcellular distribution of [$^3$H]ucb 30889 binding within rat brain.
Figure 8B:
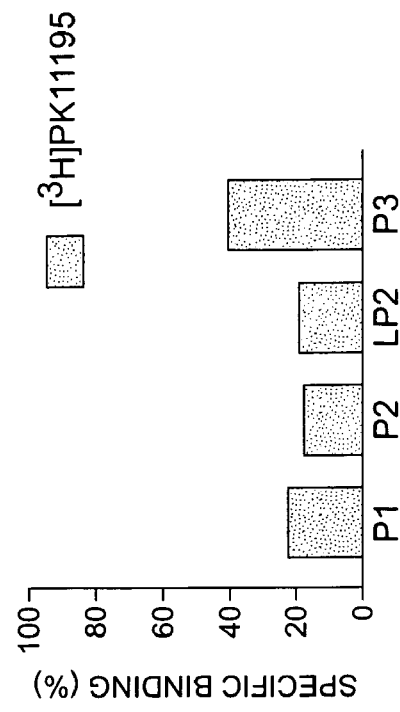
Figure 8C:
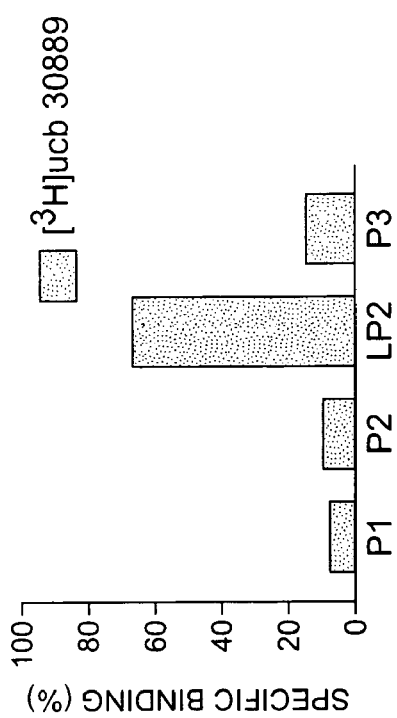
Figure 8D:
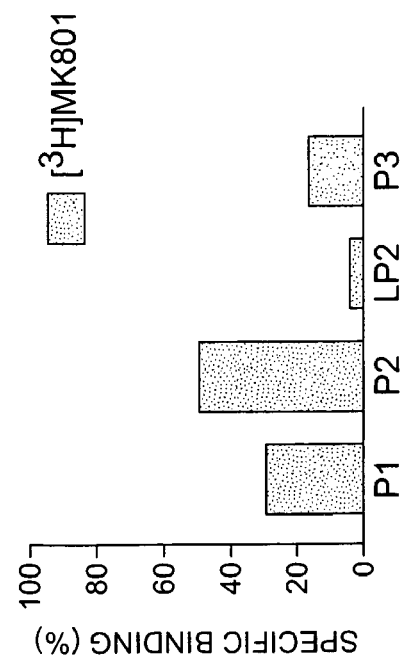

Competition binding curves showed that ucb 30889 binds to LBS with about 10 fold higher affinity than LEV (FIG. 4). The pKi of ucb 30889 (7.1±0.2) agrees well with the $K_D$ of [$^3$H]ucb 30889 as determined by the saturation binding curve (FIG. 2). $pIC_{50}$ values for a variety of levetiracetam analogues and other compounds known to interact with the LBS, such as pentylenetetrazol or bemegride (Noyer et al., 1995), were identical whether obtained with [$^3$H]ucb 30889 or [$^3$H]levetiracetam (FIG. 5).

Rat brain sections incubated with [$^3$H]ucb 30889 (FIG. 6) show that LBS labeled by [$^3$H]ucb 30889 are diffusely localized throughout the brain and that this binding can be inhibited by levetiracetam at concentrations equivalent to those observed in in vitro binding (FIG. 4).

This example demonstrates through competition binding studies and tissue distribution that ucb 30889 and LEV are both labeling the same sites, namely the LBS which is localized throughout the central nervous system. Compared to LEV, ucb 30889 binds to the LBS with 10 fold higher affinity and with a very low non specific binding. These criteria along with suitable binding kinetics at 4° C. made it possible to use this radioligand to perform autoradiography binding studies on brain slices (FIG. 6) and to show the anatomical distribution of LBS in rat brain.

Example 2

Cellular and Subcellular Distribution of the LBS

To identify and characterize the LBS in situ, [$^3$H]ucb 30889 was used to map the LBS within the brain and to study both its cellular and subcellular distribution. For rat brain autoradiography, 25 μm slices were incubated with 1.3 nM [$^3$H]ucb 30889 for 120 min at 4° C. in 50 mM Tris-HCl buffer (pH 7.4). Binding assays with rat brain membranes and various neuronal cell lines were performed under similar conditions. Non-specific binding was determined by the inclusion of 1 mM levetiracetam in the assay. For photolabeling, membranes were incubated with 40 nM [$^3$H]ucb 30889 for 120 min at 4° C. in the same buffer, followed by irradiation with UV-light for 30 min (Fuks et al., Eur. J. Pharmacol. 478:11-19 (2003)).

For rat brain autoradiography, 25 μm slices were incubated with 1.3 nM [$^3$H]ucb 30889 for 120 min at 4° C. in 50 mM Tris-HCl buffer (pH 7.4). FIG. 7 shows that ucb 30889 binding sites are heterogeneously distributed in the rat brain. While there is no apparent binding in the white matter there is a high level of binding in the dentate gyrus, the superior colliculus, several thalamic nuclei and in the molecular layer of the cerebellum. Binding is less pronounced in the cerebral cortex, the hypothalamus and the striatum. Abbreviations: cc, corpus callosum; Aca, anteria commissure; ic, internal capsule; Mtg, mamillotegmental tractus; Mt, mammillothalamic tractus; ML, molecular layer; Hi, hippocampus; DG, dentate gyrus; sc, superior colliculus; CG, central grey; Pu, caudate putamen; Pv, paraventricular nucleus; MG, geniculate nuclei; Po hy, posterior hypothalamic areas; Hb, habenula; Pi, piriform cortex.

[$^3$H]ucb 30889 binding in cerebellar granule neurons and PC 12 cells showed high levels of specific binding (Table 1). The Kd being similar to the value measured in rat cerebral cortex (42 nM; see Example 1). The same specific binding site could not be detected in primary astrocytes and in a range of CNS-related cell lines and non neuronal cell lines. Abbreviation: nd, not detected.

TABLE 1

Density and affinity of [$^3$H]ucb 30889 binding in various cell types

| Cell type | $B_{max}$ | Kd |
|---|---|---|
| Rat cerebellar granule neurons | 0.7 pmol/mg protein | 59 nM |
| Mouse cortical neurons | 1.4 pmol/mg protein | 34 nM |
| Mouse cortical astrocytes nd | nd | |
| PC12 | 1.4 pmol/mg | 40 nM |
| SK-N-SH | nd | nd |
| NG108-15 | nd | nd |
| N1E-115 | nd | nd |
| HCN-1a | nd | nd |
| CHO-K1 | nd | nd |
| COS-7 | nd | nd |

Rat brain membranes were separated by differential centrifugation (FIG. 8). Binding to LBS (8A), muscarinic (8B), NMDA (8C) and peripheral benzodiazepine (8D) receptors was determined using [$^3$H]ucb 30889, [$^3$H]NMS, [$^3$H]MK801 or [$^3$H]PK11195, respectively. This study shows that the levetiracetam binding site is present in crude synaptosomes (P2), microsomal membranes (P3) and is enriched in synaptic vesicles (LP2). In contrast, the other studied receptors are not more abundant in LP2 compared to P2 or P3. P1 is a low speed pellet containing nuclei and large debris.

Figure 9:
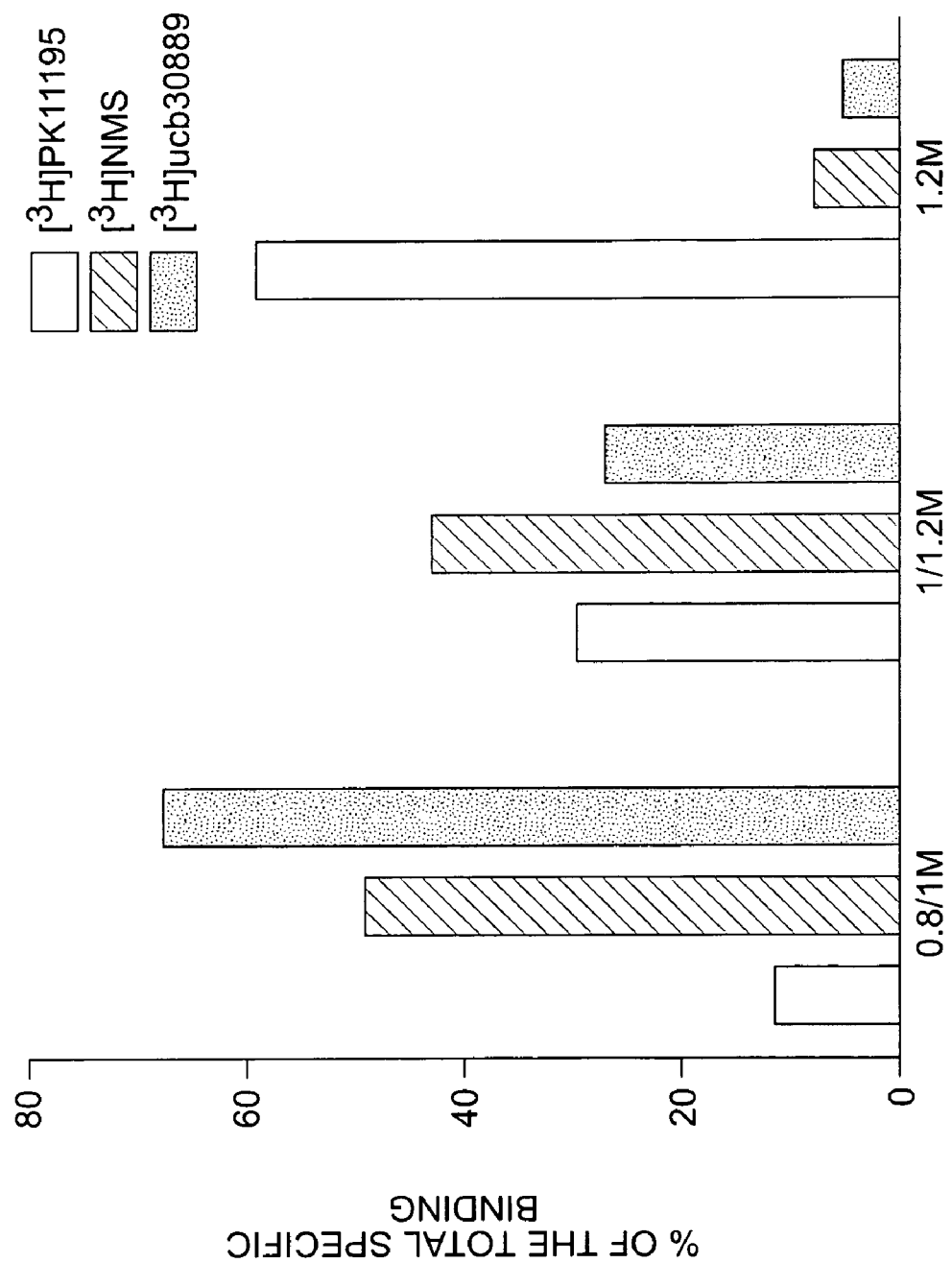
FIG. 9 depicts the subfractionation of the synaptosomal fraction by centrifugation in sucrose gradient.

A fractionation onto a sucrose gradient was used to isolate the subcellular compartments from crude synaptosomes. The LBS was found in purified synaptic membranes but was not present in the 1.2 M sucrose pellet containing the purified mitochondrial fraction (FIG. 9). As a control for the purity of the subcellular fractions, the distribution of the muscarinic and the peripheral benzodiazepine receptors was also analyzed. Data are expressed as percentage of the total specific binding.

Crude synaptosomes (P2 fraction) were preincubated with 40 nM [$^3$H]ucb 30889, then irradiated with UV light and washed. At 0 min 1 mM levetiracetam was added and aliquots were counted at the indicated times (FIG. 10A). Nonspecific binding (open symbol) was determined using 1 mM levetiracetam. FIG. 10B shows the same experiment, but performed in the absence of UV light irradiation. These results indicate that during UV irradiation the radioligand inserts covalently in the binding domain of the LBS.

Figure 11:
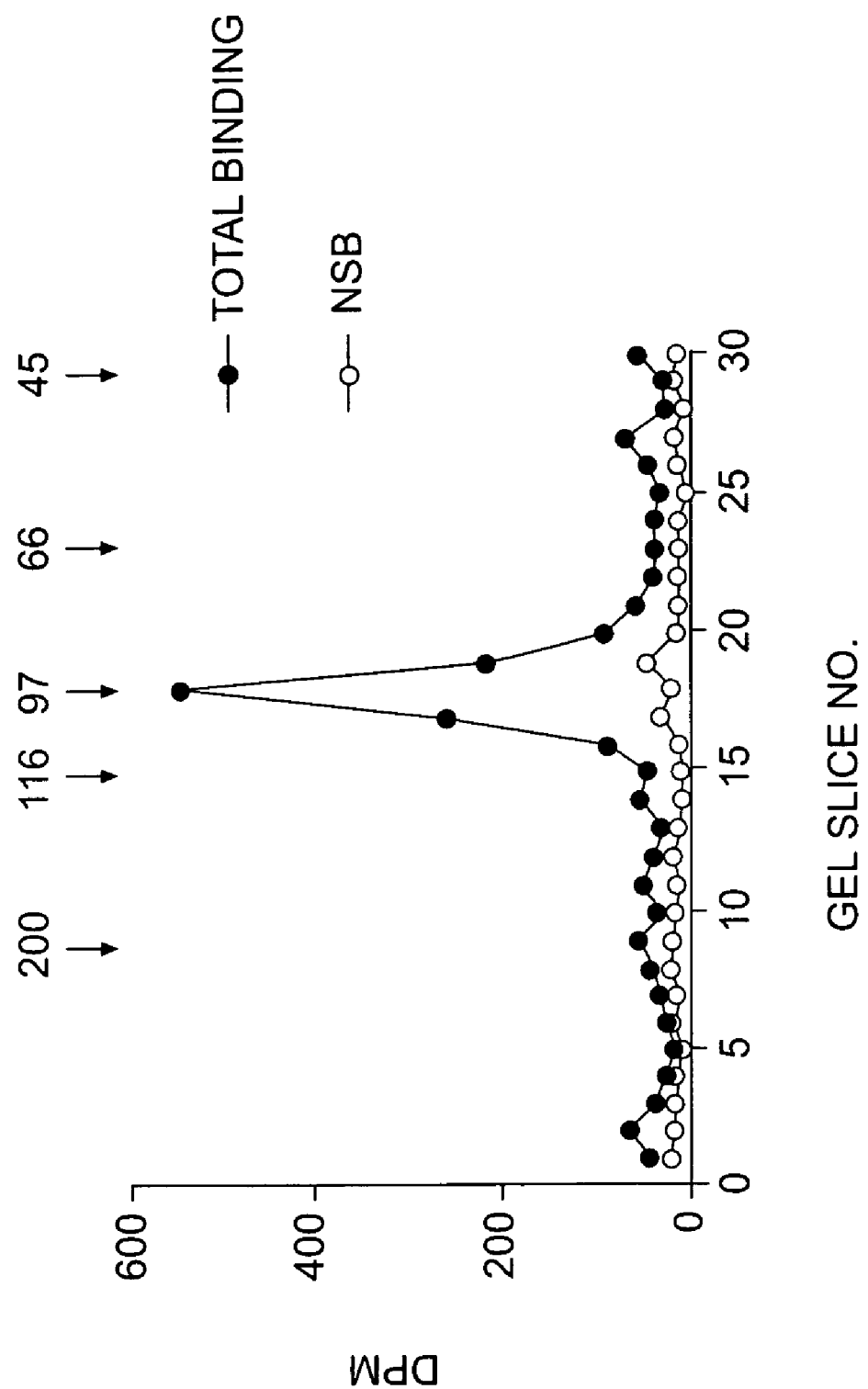
FIG. 11 depicts gel electrophoresis of membrane proteins labeled by [$^3$H]ucb 30889.

Photoaffinity labeling was performed in the absence or in the presence of 1 mM levetiracetam. The proteins were resolved by SDS-PAGE using an acrylamide concentration of 7.5% (w/w) and the radioactivity was assessed in each slice of the gel. The major site of incorporation occurs at a molecular weight of 93,000 (FIG. 11) (Fuks et al., 2003)

In this example it is shown that the [$^3$H]ucb 30889 binding site in rat brain has a unique profile of distribution and does not appear to correlate with any specific neurotransmitter system that is typically associated with epilepsy. This novel binding site is restricted to neuronal cell types and several brain areas. This novel radioligand can be used as a photoaffinity label and binds covalently to a membrane protein of high molecular weight which is mainly located in synaptic vesicles.

Example 3

The LBS is on SV2A

In this example, the biochemical characterization of LBS in rat brain led to studies to identify potential candidate LBS proteins for cloning and binding characterization. Based on the integral membrane nature of the protein, brain specific expression, apparent size, and synaptic vesicle localization, the SV2 protein family was analyzed as a candidate for localization of the LBS. Accordingly, SV2 proteins were cloned and assayed for binding of LBS ligands.

Materials: Levetiracetam and derivatives were synthesized at UCB Pharma (Braine-l'Alleud, Belgium). [$^3$H]ucb 30889, (2S)-2-[4-(3-azidophenyl)-2-oxopyrrolidin-1-yl]butanamide (32 Ci/mmol), was custom labelled by Amersham Biosciences (Roosendaal, The Netherlands). The monoclonal antibody against SV2 proteins developed by Buckley and Kelly (Buckley et al., J. Cell. Biol., 100, 1284-94 (1985)) was obtained from the Developmental Studies Hybridoma Bank developed under the auspices of the NICHD and maintained by The University of Iowa, Department of Biological Sciences, Iowa City, Iowa 52242. This antibody is cross-reactive against all three SV2 isoforms, SV2A, SV2B, and SV2C.

Wild-type and Knockout Mouse Binding Experiments

SV2A knockout mice have been previously reported (Crowder et al. Proc. Natl. Acad. Sci. U.S.A. 96, 15268-73 (1999)). The generation of SV2B knockouts will be reported elsewhere. SV2B knockouts were bred with animals heterozygous for the SV2A gene disruption to produce SV2A+/−SV2B−/− breeders which were used to generate SV2A/B knockouts. Wild type C57-B16 and SV2 KO mouse brain membranes were prepared for binding assays and the binding reaction was performed as described previously with slight modifications (Gillard et al., Eur. J. Pharmacol. In Press (2003)). Frozen whole brains were homogenized (10% w/v) in 20 mM Tris-HCl buffer (pH 7.4) containing 250 mM of sucrose (buffer A). The homogenates were spun at 30,000×g at 4° C. for 15 min and the pellets resuspended in the same buffer. After incubation at 37° C. for 15 min, the membranes were washed 2 times using the same centrifugation protocol. The final pellets were resuspended in buffer A and stored in liquid nitrogen. Thawed brain membrane proteins (0.1 mg/assay) were incubated 120 min at 4° C. in 0.5 ml of a 50 mM Tris-HCl buffer (pH 7.4) containing 2 mM MgCl$_2$, and [$^3$H] ucb 30889 (1.8 nM). At the end of the incubation period, the membrane-bound radioligand was recovered by rapid filtration through GF/C glass fiber filters pre-soaked in 0.1% polyethyleneimine. The membranes were washed with 8 ml of ice-cold Tris buffer (pH 7.4). The total filtration procedure did not exceed 10 s per sample. The filters were dried and the radioactivity determined by liquid scintillation. $pIC_{50}$s determination was performed by computerized non-linear curve fitting methods (Graphpad Prism® software, San Diego, Calif.).

For Western blot experiments, aliquots of brain homogenates from the wildtype and knockout animals were extracted at room temperature with SDS-PAGE sample buffer containing BME. Equivalent amounts of each sample (approx. 10 μg total protein) were loaded on a 4-12% Tris-Glycine NOVEX gradient gel (Invitrogen Life Sciences) and separated. After transfer to a nitrocellulose membrane and blocking, the blot was probed with a monoclonal cross-reactive to all SV2 proteins (Buckley et al., J. Cell. Biol., 100, 1284-94 (1985)), and an HRP-anti-mouse secondary antibody was used to label the primary. The blot was developed with luminescent horseradish peroxidase reagents and photographed.

Binding Experiments with [H]ucb 30889 Against Heterologously Expressed hSV2A

Figure 17B:
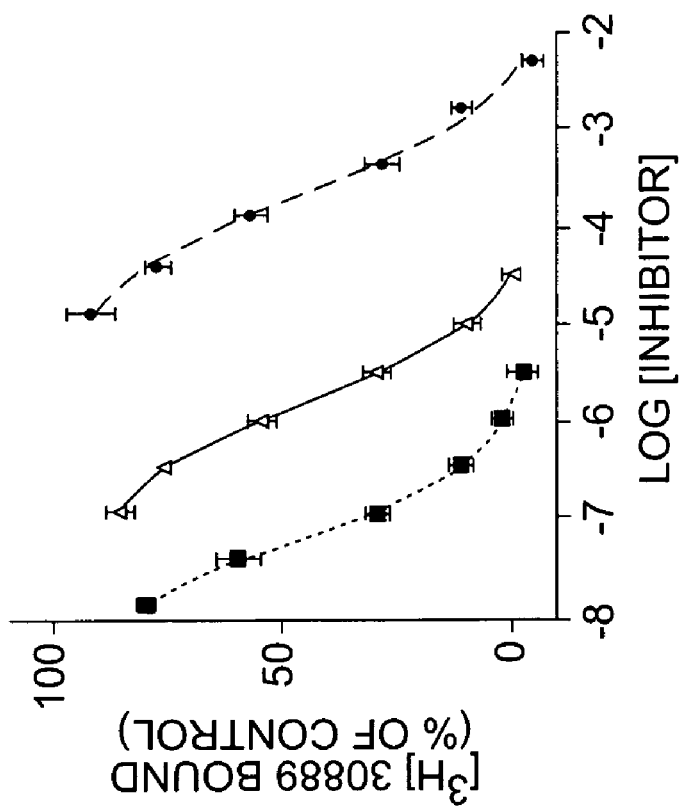
FIGS. 17(a and b) depicts binding of [$^3$H]ucb 30889 to COS-7 cells expressing hSV2A. A. Binding of [$^3$H]ucb 30889 to hSV2A transiently expressed in COS-7 cells. [$^3$H] ucb 30889 is tested for binding to either untransfected COS-7 cells, or COS-7 cells transiently expressing either β-gal or hSV2A. [$^3$H]ucb 30889 alone (□) [$^3$H]ucb 30889 plus 1 mM LEV (■). B. $IC_{50}$ curves of LEV, ucb L060, ucb 30889 against hSV2A transiently expressed in COS-7, in the presence of [$^3$H]ucb 30889. LEV (Δ) ucb 30889 (■) ucb L060 (●). Error bars are SEM, n=3.

For binding experiments on confluent, transfected cells (FIG. 17), cells in 24 well plates were slowly cooled to 4° C. and rinsed once with cold phosphate-buffered saline (PBS). PBS was aspirated and binding reagents were added in PBS. In binding experiments, [$^3$H]ucb 30889 was added to all wells at 1.8 nM, in the presence or absence of differing amounts of unlabelled inhibitors. The cells were incubated at 4° C. for 2 h and the assay was terminated by rinsing the cells 3x rapidly with ice-cold PBS. After a final aspiration, 200 μl of 0.1N NaOH was added to lyse the cells, and the samples were counted in scintillation fluid on a beta counter.

For binding experiments on previously frozen transfected COS-7 cells (FIG. 18), 2 to 3×10$^4$ cells were incubated 120 min at 4° C. in 0.2 ml of a RPMI-HEPES 25 mM solution containing [$^3$H]ucb 30889 (1.8 nM) and increasing concentrations of unlabelled competing drugs. The termination of the binding reaction by filtration and radioactivity counting was performed as described above.

Audiogenic Seizure Mouse Model

Anti-seizure activity of LEV and analogues were assessed in sound-susceptible mice by exposing the mice to acoustic stimuli of 90-db, 10 to 20-kHz for 30 sec, 60 min following intraperitoneal pretreatment. The reported $ED_{50}$ values were obtained from testing of 4 to 8 groups (n=10) administered different doses and reflect the potency of the compounds for inhibiting clonic convulsions.

Human SV2A was cloned from a human fetal brain cDNA library as a 3609 bp PCR product comprising the coding region and significant flanking regions from the transcript. Using a vector containing the SV2A coding region plus significant flanking DNA as a source, the coding region was PCR amplified without the flanking regions. This product was cloned into a GATEWAY (Invitrogen) donor vector for ease of subcloning. Only the use of a cloning vector with strong transcription stop sites directly upstream of the cloning site resulted in successful cloning of coding-region only SV2A cDNA. This suggests that this product may be toxic to *E coli*, even in small amounts. Sequencing of the final pDONR GATEWAY SV2A clone showed that it had 2 mutations: one silent, and one a Leu-to-Pro mutation. The non-silent mutation was corrected and sequencing confirmed that the correct, full length human SV2A coding sequence was cloned.

The human SV2A coding region was transferred from the pDONR GATEWAY cloning vector to a pDEST 12.2 Gateway expression vector. This vector has a CMV promoter driving the introduced gene, and an SV40 ori, which allows very high levels of replication in the COS-7 cell line, which contains the large T antigen. In addition, the human SV2A coding region was transferred into a pDEST 40 Gateway expression vector. This vector is very similar to the 12.2 vector above, with a CMV promoter driving expression of hSV2A, and an SV40 ori, and a Neomycin resistance gene.

Initial tests of SV2A expression using the pDEST 12.2 vector was performed in the COS-7 cell line, which had previously been demonstrated successful expression of SV2 proteins. The COS-7 cell line was tested for $^3$H-30889 binding, with no binding above background observed, and thus no significant, measurable presence of the Levetiracetam binding site (LBS). In addition, a PC12 cell line subclone, PC12a, which is low in LBS, was used to establish a pool of PC 12 cells expressing hSV2A under stable antibiotic selection.

Figure 12A:
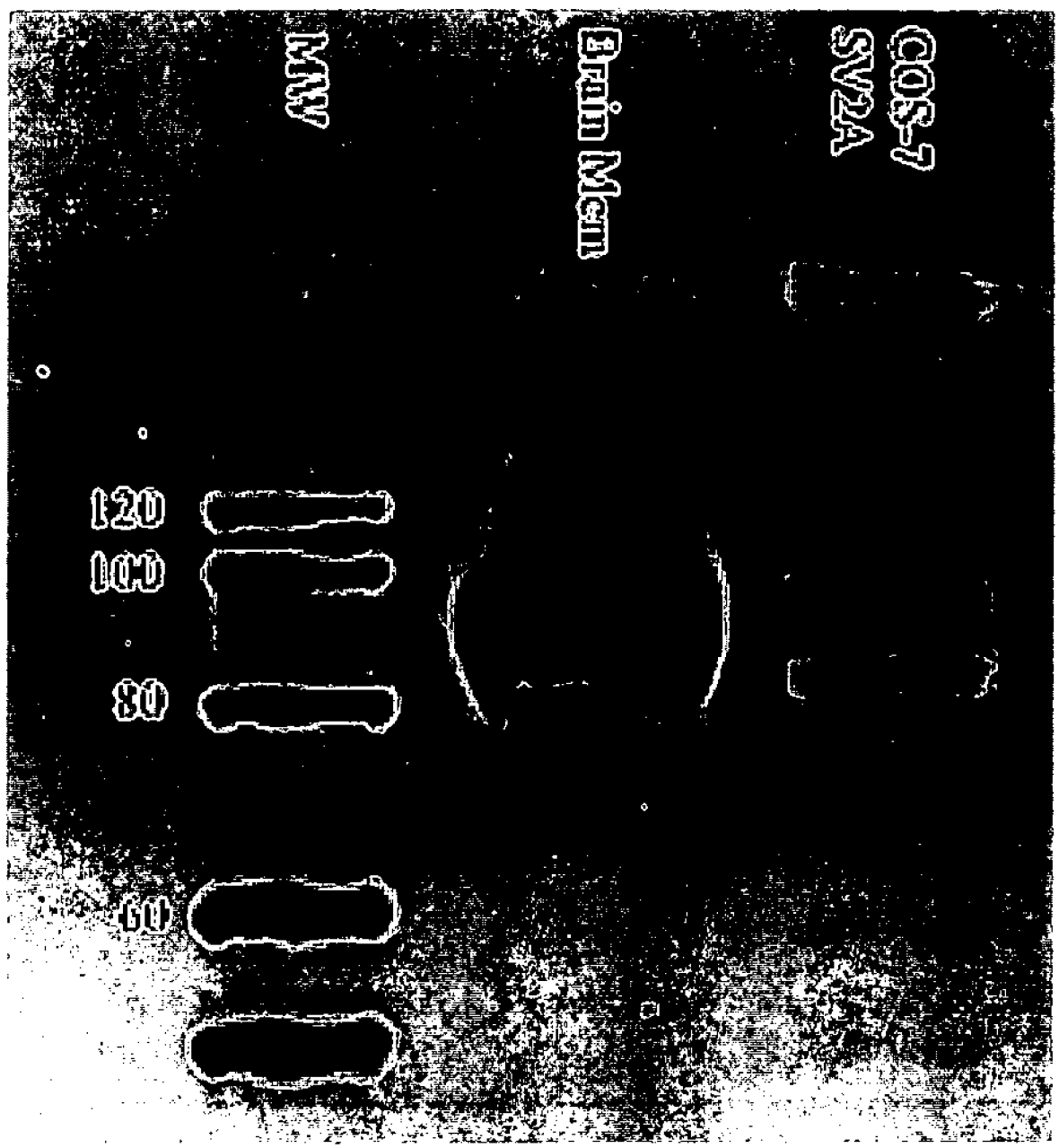
FIGS. 12(a and b) depicts immunostained lysates of the COS-7 cells transfected with SV2A, crude rat brain membranes, and several different PC12 lysates with different levels of LBS.
Figure 12B:
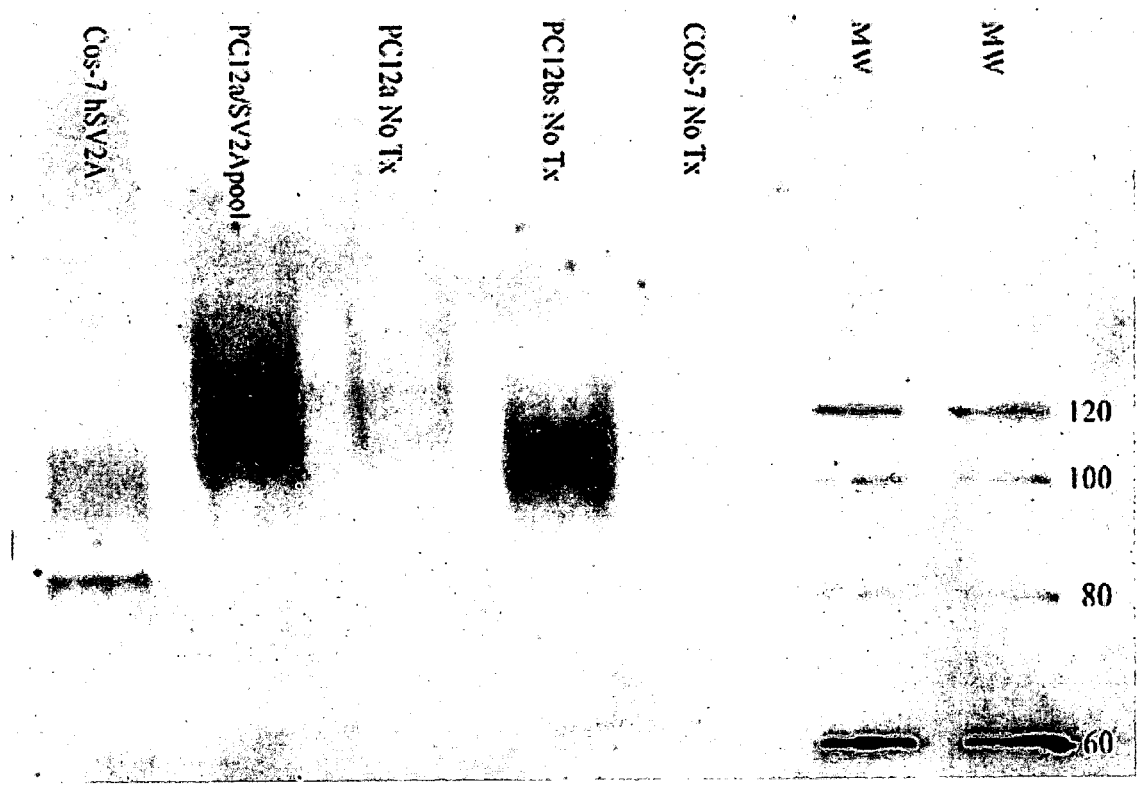

Lipofectamine 2000 (Invitrogen) transfection reagent was used to transfect DNA into 90% confluent COS-7 cells. Also, the same reagent was used to transfect the hSV2A containing vector into the PC12a cell line, and selecting for antibiotic resistance. Anti-SV2A polyclonal antibody (CalBiochem) was used to test for expression in either transfected COS-7 cells, or transfected PC12a cells, of the SV2A product. Lysates of the COS-7 cells were collected at 18 hrs after transfection on an SDS-PAGE gel, transferred to a membrane, and probed with a polyclonal antibody against SV2A, in comparison to crude rat brain membranes (FIG. 12A). Also shown are lysates from a non-transfected COS-7 cells, non-transfected PC12a cells (low in LBS), PC12bs cells (high in LBS), or PC12a cells transfected with hSV2A (FIG. 12B). No labeling of protein bands is observed in the untransfected COS-7 control, while the transfected COS-7 cells show multiple bands, with most density in the range of 80-120 kD, perhaps due to multiple glycosylation states of the expressed protein. In addition, SV2A immunoreactivity is present in the PC12bs and PC12a/hSV2A samples, but largely absent in the low LBS PC 12a cells (FIG. 12B).

Figure 13:
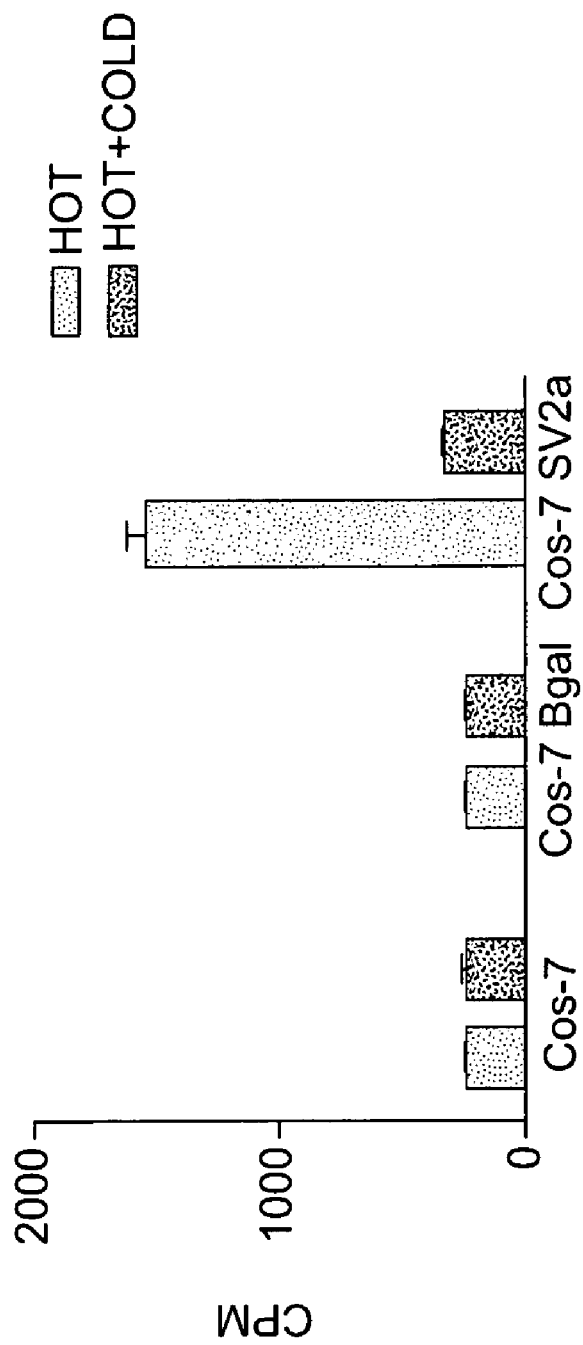
FIG. 13 depicts specific binding of [$^3$H]ucb 30889 to COS-7 transfected with SV2A-12.2, transfected with control β-gal expressing vector, or cells that have not been transfected.

In a binding experiment, specific binding was measured of [$^3$H]ucb 30889 to COS-7 cells that have either been transfected with SV2A-12.2, or as controls, a β-gal expressing vector, or cells that have not been transfected (FIG. 13). Triplicate wells of a 24-well plate were incubated with either 1 nM [$^3$H]ucb 30889 (labeled "Hot"), or [$^3$H]ucb 30889 plus an excess of cold Levetiracetam (50 μM) (labeled "Hot+Cold"). The cells were incubated at 4° C. for 2 hours, and then washed rapidly with ice-cold PBS. The cells were lysed on the plate, transferred to scintillation vials with scintillation fluid and counted for $^3$H decay emission. These results show that COS-7 cells transfected with SV2A have acquired the capability to specifically bind [$^3$H]ucb 30889. In identical intact cell binding experiments using PC12bs cells, known to express the LBS, a 1.5 to 2-fold difference in CPM between the 'hot' and 'hot+cold' samples is typically seen, as compared to the 5-fold difference seen here.

Figure 14:
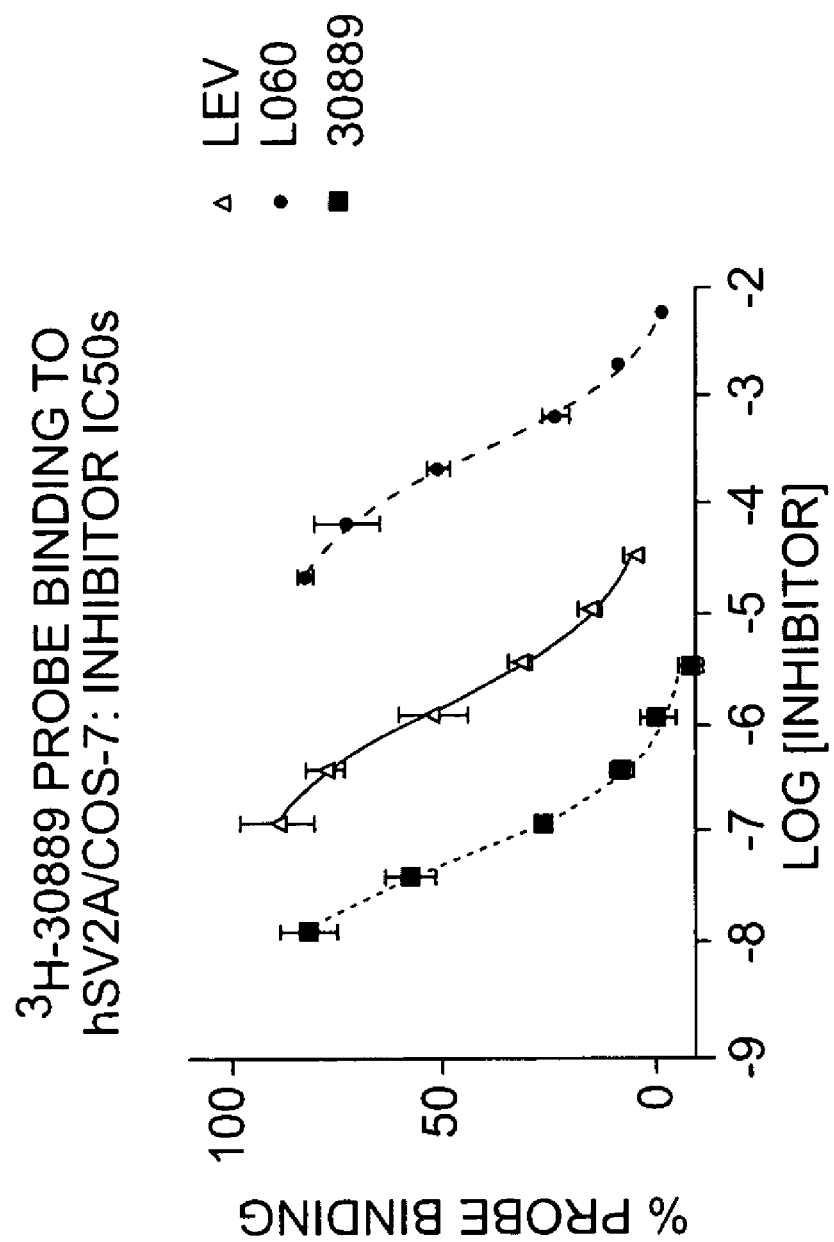
FIG. 14 depicts an $IC_{50}$ plot comparing three different ligands binding to SV2A in the presence of 3H-30889.

Further studies characterized the binding of [$^3$H]ucb 30889 to SV2A expressed in COS-7 cells in more detail. COS-7 cells were transfected in a 24-well plate and assayed for binding as above. A series of concentrations of either Levetiracetam or cold 30889 were added in order to generate $IC_{50}$s for these compounds against SV2A expressed in COS-7 cells (FIG. 14). These results indicate that SV2A is functionally equivalent with the binding site for Levetiracetam that has been observed in rat brain and PC12 subclones. The correlation between LBS binding affinity and the anti-seizure properties of Levetiracetam and it analogues, taken together with the preceding observation, provide support that the synaptic vesicle protein SV2A is not only the native binding site for the anti-epileptic compound Levetiracetam, but suggests a link between the function and modulation of the synaptic vesicles by Levetiracetam and it's anticonvulsant properties.

Figure 17A:
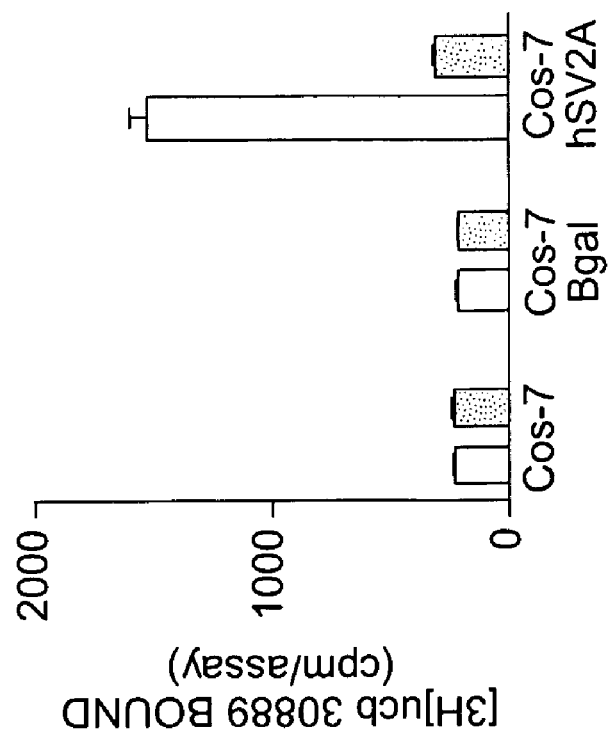

In a separate experiment, heterologous expression experiments were performed to confirm that SV2A alone is solely responsible for the brain binding of LEV. Human SV2A was transiently expressed in the COS-7 cell line, as verified by Western analysis (data not shown), and observed binding to [$^3$H]ucb 30889 that is displaced by excess LEV (FIG. 17A). No binding under identical conditions to either untransfected COS-7 cells, or COS-7 cells transfected with a vector encoding β-galactosidase. In experiments testing the ability of unlabeled compounds to displace [$^3$H]ucb 30889 from hSV2A expressed in COS-7 cells, the affinities of ucb 30889, LEV, and LEV's enantiomer, ucb L060, show the same rank order, and similar values (FIG. 17B), to those previously reported in studies with rat brain ((Noyer et al., Eur. J. Pharmacol. 286, 137-146 (1995); Gillard et al., 2003). Critically, ucb L060 binds with significantly less affinity to hSV2A than does LEV, which is a key characteristic of the binding site in brain (Noyer et al., Eur. J. Pharmacol. 286, 137-146 (1995); Gillard et al., 2003In addition, the binding of [$^3$H]ucb 30889 against both hSV2B and hSV2C expressed in the transient COS-7 system were tested. The results indicate no binding above background (data not shown), consistent with the results from knockout mouse binding studies.

Figures 18A, 18B:
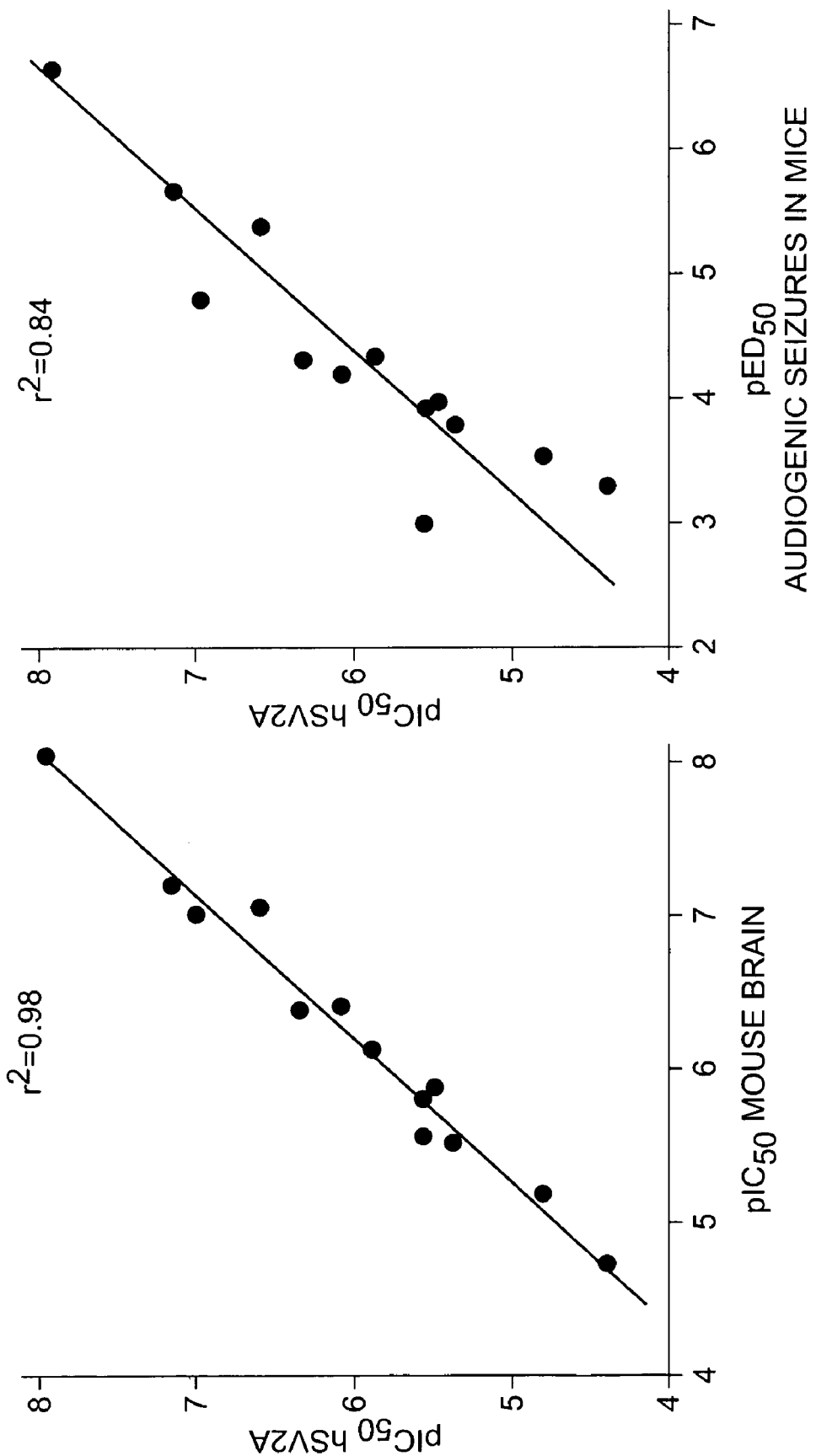
FIGS. 18(a and b) depicts binding of [$^3$H]ucb 30889 in the presence of competing drugs. A. Correlation of binding of a series of LEV compounds to mouse brain and to hSV2A, $pIC_{50}$s measured against [$^3$H]ucb 30889. The $pIC_{50}$ values are the mean of two independent experiments, where each determination lies within 0.2 log units of the mean. B. Correlation of binding of a series of LEV family compounds to hSV2A assayed in transiently transfected COS-7 cells, $pIC_{50}$s measured against [$^3$H]ucb 30889, and of anti-seizure potencies in the mouse audiogenic model.

Testing the binding of LEV and several analogs to hSV2A expressed in COS-7, revealed that pIC$_{50}$s are highly correlated ($r^2$=0.98) with the values obtained in mouse brain (FIG. 18A) and rat brain extracts (data not shown). There was also a clear correlation between the affinities of these compounds for hSV2A in COS-7 and the potency of their antiseizure protection in the mouse audiogenic model of epilepsy ($r^2$=0.84) (FIG. 18B). This data is consistent with a previous report of a correlation between binding of LEV analogs in rat brain and potency in the same model (Noyer et al., Eur. J. Pharmacol. 286, 137-146 (1995)). The binding of other AEDs, including valproate, carbamazepine, phenytoin, ethosuximide, felbamate, gabapentin, tiagabine, vigabatrin and zonisamide was also investigated. None of the AEDs at concentrations up to 100 μM, competed with [$^3$H]ucb 30889 for binding to SV2A (data not shown). This confirms previous binding studies of AEDs against the LEV binding site in rat brain (Noyer et al., Eur. J. Pharmacol. 286, 137-146 (1995); Gillard et al., Eur. J. Pharmacol. 2003)).

Example 4

Assays for Compounds which Modulate Neurological Disorders, Endocrinopathy and Hormonal Diseases In order to identify compounds or agents which modulate neurological disorders associated with synaptic function and endocrinological disorders, studies were undertaken to identify additional compounds which compete with LEV and ucb 30889 for binding to the LBS of a SV2 protein.

SV2A transfected COS-7 cells as disclosed in Example 3 are exposed to a potential binding partner or agent. Control cells are exposed to vehicle only, or are exposed to unlabeled ucb 30889 or LEV. Following this exposure, the cells are then incubated with [$^3$H]ucb 30889, as in Example 3, cells are incubated at 4° C. for 2 hours, and then washed rapidly with ice-cold PBS. The cells are lysed, transferred to scintillation vials with scintillation fluid and counted for $^3$H decay emission.

Compounds which are found to compete with ucb 30889 for binding to the LBS are subject to further analysis for the ability to modulate seizures in audiogenic-susceptible mice. Audiogenic-susceptible mice are administered an amount of the compound which is comparable to an effective amount of LEV. As a control, identical audiogenic-susceptible mice are administered an effective amount of LEV, or a compound which does not modulate seizures, such as piracetam.

Example 5

Biotinylated Ligands as Tools to Screen Chemical Libraries and Characterize the SV2 Proteins The present invention dicloses a method of using novel biotinylated ligands as tools to screen chemical libraries and characterize SV2 proteins. The present invention provides nonradioactive-labelled SV2A/LBS ligands containing a biotin tag for screening purposes with no radioactive waste and higher throughput. The present invention also provides a photoactivable version for labelling and SV2A/LBS detection in biological samples.

Figure 19:
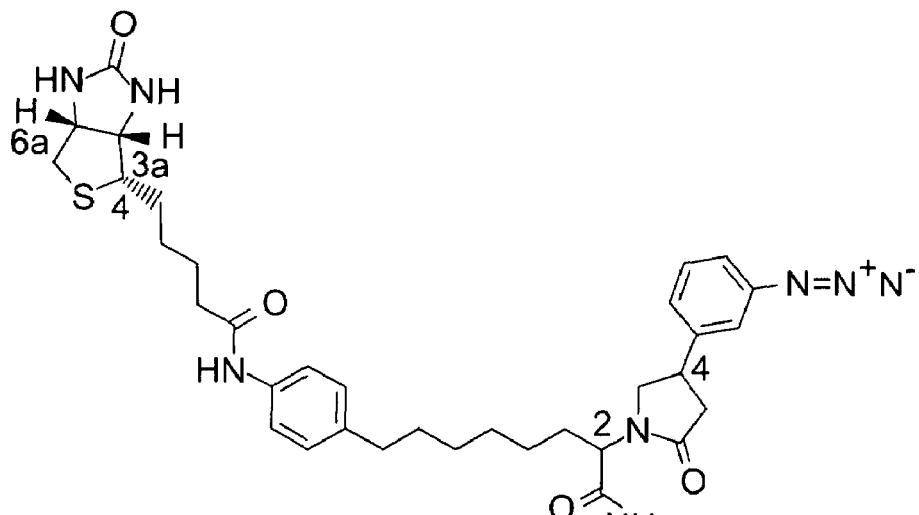
FIG. 19 depicts the structure of ucb-101282-1. This ligand is a biotinylated derivative of ucb 30889.
Figure 20:
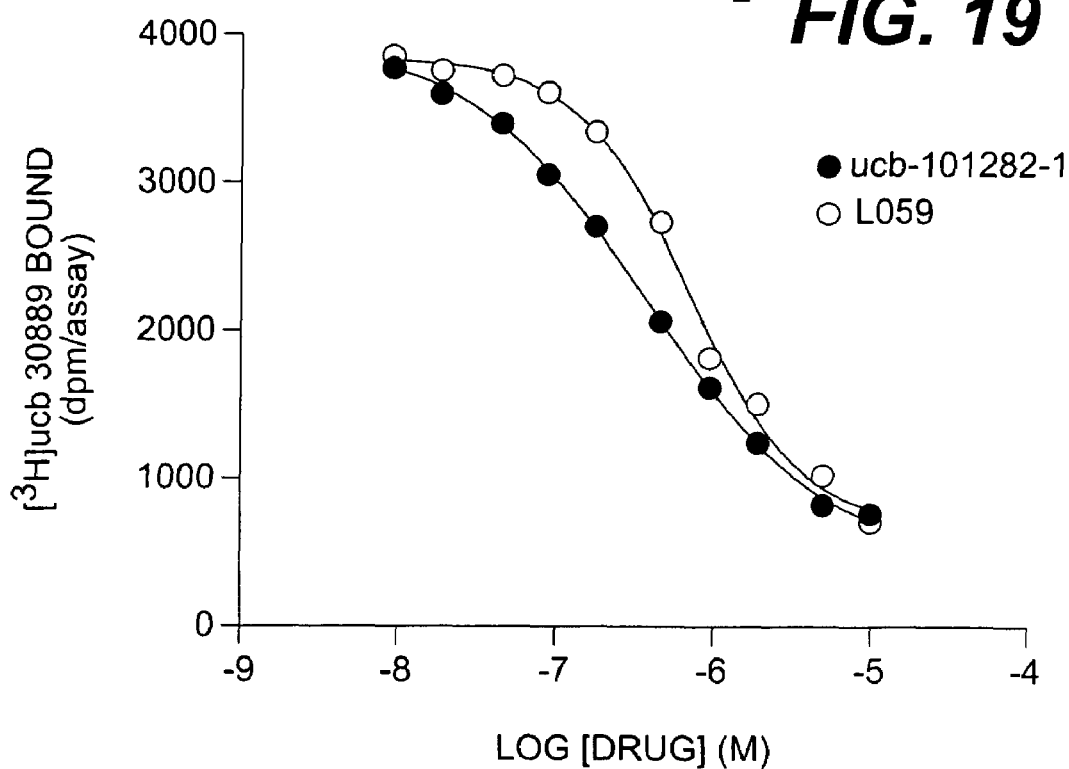
FIG. 20 depicts that the pKi of ucb-101282-1 is 6.3 (n=2) in rat brain membranes which is equivalent to the affinity reported for LEV.

In this example, the binding of ucb-101282-1 to SV2A/LBS was characterized in rat brain membranes. This molecule is a biotinylated derivative of ucb 30889 (FIG. 19). This ligand had a pKi of 6.3 (n=2) in rat brain membranes which was equivalent to the affinity reported for L059 (FIG. 20). This ligand was also designed to cross-link the biotin tag to the LBS/SV2A with an azidophenyl motif capable of forming a covalent complex with the protein upon UV light irradiation.

Example 6

Method for Solubilizing SV2A and Affinity Purification

The present invention discloses a method of solubilizing SV2A and affinity purification. The method comprises solubilizing SV2A/LBS proteins which includes treating the membrane with a detergent. The method maintains the activity of the membrane proteins after solubilization as evaluated in binding assays and protein-protein interaction studies.

Preparation of Soluble SV2A and Quantitation by Binding Assay

Figure 21A:
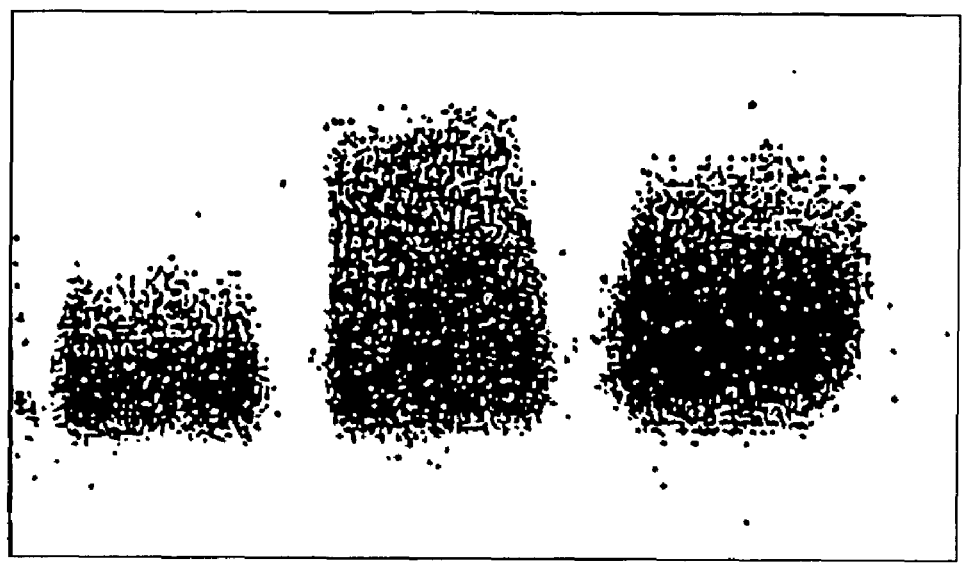
FIGS. 21(a, b, and c) depicts preparation of soluble SV2A and quantitation of by binding assay. A. Detection by western blot using anti-SV2A antibodies of soluble SV2A in the supernatant of solubilized rat brain membranes. B. Analysis of the ability of levetiracetam and ucb 30889 to specifically bind to soluble SV2A. C. Scatchard analysis indicates that the $K_D$ for the binding of [$^3$H] ucb 30889 to SV2A in native rat brain membrane is 30 nM, while that for the soluble protein is 82 nM.
Figure 21B:
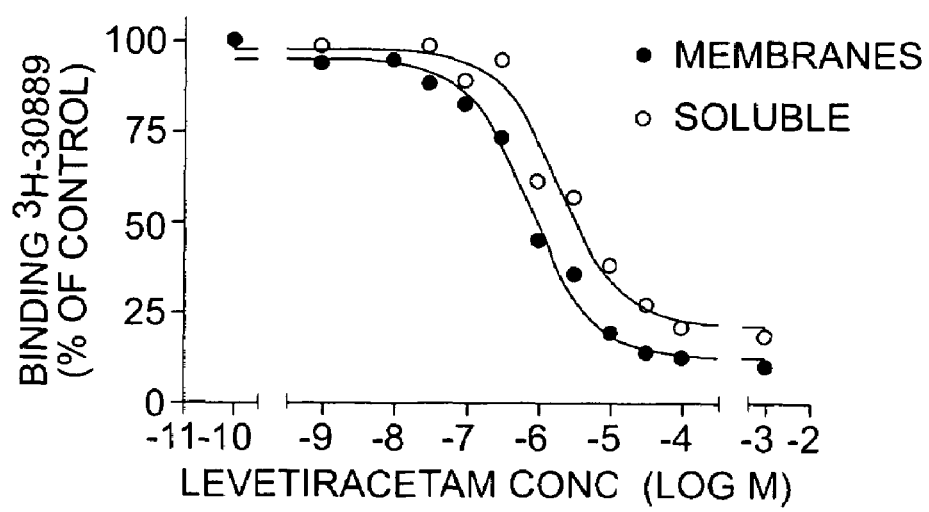
Figure 21C:
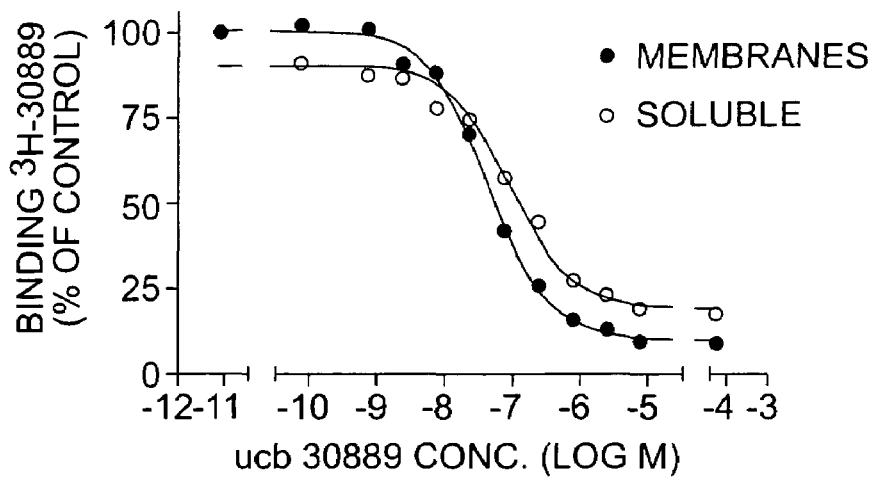

The rat brain membranes were diluted in a solubilization buffer (Tris-HCl 20 mM pH 7.4, 0.25 M sucrose, protease inhibitors Complete Roche) containing n-dodecyl-β-D-maltoside 15 mM and incubated for two hours at 4° C. Subsequently, the solution was centrifuged at 4° C. for one hour at 100,000 g. The soluble SV2A was found in the supernatant as detected by western blot using anti-SV2A antibodies (FIG. 21A). The supernatants were incubated with [$^3$H]ucb 30889 as described. Binding experiments indicated that the specific binding is due to a soluble form of SV2A. In order to detect the specificity of the SV2A binding, the ability of levetiracetam and ucb 30889 to specifically bind to the soluble SV2A was examined. The affinities of the molecules were equivalent to that exhibited by ligands to the native membrane (FIG. 21B). Scatchard analysis indicates that the K$_D$ for [$^3$H]ucb 30889 for to the SV2A in native membrane is 30 nM, while that for the soluble protein is 82 nM (FIG. 21C). Thus, the binding properties of the soluble SV2A are similar to the membrane-bound native form indicative that the soluble protein maintains its native structural conformation in n-dodecyl-β-D-maltoside.

Affinity Purification of the Soluble SV2A and Identification of Putative SV2A Partners Supernatants from solubilized membranes were incubated with anti-SV2A antibodies overnight at 4° C. The mixture was rotated with protein A-Sepharose beads for 1 hour at 4° C. in Tris-HCl 20 mM pH 7.4, 0.25 M sucrose, protease inhibitors Complete (Roche). The resin was washed several times and the collected fractions contained immunopurified SV2A (FIG. 22). As explained above, SV2A is maintained in its native conformation after solubilization in n-dodecyl-β-D-maltoside. Therefore, since synaptotagmin is a well known partner of SV2A, the immunopurified fractions were tested to determine whether synaptotagmin was still associated to SV2A after the purification procedure. Western analysis of the immunopurified fractions confirmed the presence of synaptotagmin associated to soluble SV2A, while the isoform SV2B was not detected. Thus, the solubilization and purification procedure can be used to perform SV2A-protein interactions studies.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A method of identifying a compound or an agent that binds a levetiracetam binding site (LBS) of a synaptic vesicle protein 2 (SV2) protein comprising;
   a) obtaining a cell-free or membrane-free SV2 protein comprising a LBS wherein the SV2 protein is SV2A or SV2C;
   b) incubating the SV2 protein with a compound or an agent and levetiracetam (LEV) or an analog or derivative thereof that binds a LBS on an SV2 protein; and
   c) determining if the compound or agent competes with LEV or an analog or derivative thereof for binding to the LEV binding site, thereby identifying a compound or an agent that binds the LBS of the SV2 protein.

2. The method of claim 1, wherein the compound or agent is an analog or derivative of levetiracetam.

3. The method of claim 2, wherein the analog or derivative of levetiracetam is selected from the group consisting of N-alkylated 2-oxo -pyrrolidine derivatives, N-alkylated 2-oxo-piperidinyl derivatives, and N-alkylated 2-oxo-azepanyl derivatives.

4. The method of claim 1, wherein the compound or agent is an anti-SV2 antibody or fragment thereof.

5. The method of claim 4, wherein the anti-SV2 antibody or fragment thereof binds to the levetiracetam binding site of SV2 protein.

6. The method of claim 4, wherein the anti-SV2 antibody or fragment thereof is selected from the group consisting of a polyclonal antibody and a monoclonal antibody.

7. The method of claim 6, wherein the antibody fragment is selected from the group consisting of an Fab fragment, Fab' fragment, F(ab')$_2$ fragment and an scFv fragment.

8. The method of claim 6, wherein the monoclonal antibody is selected from the group consisting of a chimeric antibody, a humanized antibody, and a human antibody.

9. A method of identifying a compound or an agent that binds a levetiracetam binding site (LBS) of an SV2 protein, comprising:
   a) obtaining a cell-free or membrane-free SV2 protein comprising a LBS wherein the SV2 protein is SV2A or SV2C;
   b) incubating the SV2 protein with a compound or an agent and levetiracetam or an analog or derivative thereof that binds a LBS on an SV2 protein; and
   c) determining if the binding of levetiracetam or an analog or derivative thereof to the protein is inhibited by the compound or agent, thereby identifying a compound or agent that binds the LBS of an SV2.

10. The method of claim 9, wherein the analog of levetiracetam is (2S)-2-[4-(3-azidophenyl)-2-oxopyrrolidin-1-yl]butanamide.

11. The method of claim 9, wherein the SV2 protein is purified.

12. The method of claim 9, wherein the SV2 protein is immobilized.

13. The method of claim 9, wherein the SV2 protein is expressed on a transformed host cell.

14. The method of claim 9, wherein the levetiracetam or an analog or derivative thereof is directly or indirectly labeled.

15. The method of claim 14, wherein the label is a radiolabel.

16. The method of claim 15, wherein the radiolabel is $^3$H.

17. The method of claim 14, wherein the label is a fluorescent label.

18. The method of claim 14, wherein the label is an enzyme.

19. The method of claim 9, wherein the SV2 protein is incubated with the levetiracetam or an analog or derivative prior to addition of the agent.

20. The method of claim 9, wherein the SV2 protein is incubated with levetiracetam or an analog or derivative after addition of the agent.

21. The method of claim 9, wherein the SV2 protein is incubated with levetiracetam or an analog or derivative concurrent with the agent.

22. The method of claim 9, wherein the SV2 protein is incubated with levetiracetam.

23. A method of identifying a compound or an agent that binds the levetiracetam binding site (LBS) of an SV2 protein, comprising:
   a) obtaining a cell-free or membrane-free SV2 protein comprising a LBS wherein the SV2 protein is SV2A or SV2C;
   b) incubating the SV2 protein with a compound or an agent and (2S)-2-[4-(3-azidophenyl)-2-oxopyrrolidin-1-yl]butanamide;
   c) separately incubating the SV2 protein with (2S)-2-[4-(3-azidophenyl)-2-oxopyrrolidin-1-yl]butanamide; and
   d) comparing the binding of (2S)-2-[4-(3-azidophenyl)-2-oxopyrrolidin-1-yl]butanamide to SV2 in steps (b) and (c) to determine if the binding of (2S)-2-[4-(3-azidophenyl)-2-oxopyrrolidin-1-yl]butanamide to the protein is inhibited by the compound or agent, thereby identifying a compound or an agent that binds the LBS of the SV2 protein.

24. The method of claim 1, wherein the SV2 protein is a human SV2 protein.

25. The method of claim 24, wherein the SV2 protein is an SV2A protein comprising the amino acid sequence of SEQ ID NO: 2, or an SV2C protein comprising the amino acid sequence of SEQ ID NO: 6.

26. The method of claim 1, wherein the SV2 protein comprises conservative amino acid substitutions.

27. The method of claim 1, wherein the SV2 protein is a recombinantly expressed protein.

28. The method of claim 27, wherein the SV2 protein is recombinantly expressed from COS cells.

29. The method of claim 9, wherein the SV2 protein is a human SV2 protein.

30. The method of claim 29, wherein the SV2 protein is an SV2A protein comprising the amino acid sequence of SEQ ID NO: 2, or an SV2C protein comprising the amino acid sequence of SEQ ID NO: 6.

31. The method of claim 9, wherein the SV2 protein comprises conservative amino acid substitutions.

32. The method of claim 9, wherein the SV2 protein is a recombinant protein.

33. The method of claim 32, wherein the SV2 protein is recombinantly expressed from COS cells.

34. The method of claim 23, wherein the SV2 protein is a human SV2 protein.

35. The method of claim 34, wherein the SV2 protein is an SV2A protein comprising the amino acid sequence of SEQ ID NO: 2, or an SV2C protein comprising the amino acid sequence of SEQ ID NO: 6.

36. The method of claim 23, wherein the SV2 protein comprises conservative amino acid substitutions.

37. The method of claim 23, wherein the SV2 protein is a recombinant protein.

38. The method of claim 37, wherein the SV2 protein is recombinantly expressed from COS cells.

* * * * *

SEQUENCE LISTING

```
<160> NUMBER OF SEQ ID NOS: 16

<210> SEQ ID NO 1
<211> LENGTH: 2229
<212> TYPE: DNA
<213> ORGANISM: Homo sapiens
<220> FEATURE:
<221> NAME/KEY: CDS
<222> LOCATION: (1)..(2229)
<223> OTHER INFORMATION:

<400> SEQUENCE: 1 atg gaa gag ggc ttc cga gac cgg gca gct ttc atc cgt ggg gcc aaa        48
Met Glu Glu Gly Phe Arg Asp Arg Ala Ala Phe Ile Arg Gly Ala Lys
1               5                   10                  15 gac att gct aag gaa gtc aaa aag cat gcg gcc aag aag gtg gtg aag        96
Asp Ile Ala Lys Glu Val Lys Lys His Ala Ala Lys Lys Val Val Lys
            20                  25                  30 ggc ctg gac aga gtc cag gac gaa tat tcc cga aga tcg tac tcc cgc       144
Gly Leu Asp Arg Val Gln Asp Glu Tyr Ser Arg Arg Ser Tyr Ser Arg
        35                  40                  45 ttt gag gag gag gat gat gat gat gac ttc cct gct ccc agt gat ggt       192
Phe Glu Glu Glu Asp Asp Asp Asp Asp Phe Pro Ala Pro Ser Asp Gly
    50                  55                  60 tat tac cga gga gaa ggg acc cag gat gag gag gaa ggt ggt gca tcc       240
Tyr Tyr Arg Gly Glu Gly Thr Gln Asp Glu Glu Glu Gly Gly Ala Ser
65                  70                  75                  80 agt gat gct act gag ggc cat gac gag gat gat gag atc tat gaa ggg       288
Ser Asp Ala Thr Glu Gly His Asp Glu Asp Asp Glu Ile Tyr Glu Gly
                85                  90                  95 gaa tat cag ggc att ccc cgg gca gag tct ggg ggc aaa ggc gag cgg       336
Glu Tyr Gln Gly Ile Pro Arg Ala Glu Ser Gly Gly Lys Gly Glu Arg
            100                 105                 110 atg gca gat ggg gcg ccc ctg gct gga gta agg ggg ggc ttg agt gat       384
Met Ala Asp Gly Ala Pro Leu Ala Gly Val Arg Gly Gly Leu Ser Asp
        115                 120                 125 ggg gag ggt ccc cct ggg ggc cgg ggg gag gca caa cga cgg aaa gaa       432
Gly Glu Gly Pro Pro Gly Gly Arg Gly Glu Ala Gln Arg Arg Lys Glu
    130                 135                 140 cga gaa gaa ctg gcc caa cag tat gaa gcc atc cta cgg gag tgt ggc       480
Arg Glu Glu Leu Ala Gln Gln Tyr Glu Ala Ile Leu Arg Glu Cys Gly
145                 150                 155                 160 cac ggc cgc ttc cag tgg aca ctg tat ttt gtg ctt ggt ctg gcg ctg       528
His Gly Arg Phe Gln Trp Thr Leu Tyr Phe Val Leu Gly Leu Ala Leu
                165                 170                 175 atg gct gac ggt gtg gag gtc ttt gtg gtg ggc ttc gtg ctg ccc agc       576
Met Ala Asp Gly Val Glu Val Phe Val Val Gly Phe Val Leu Pro Ser
```

-continued

```
               180                 185                 190
gct gag aaa gac atg tgc ctg tcc gac tcc aac aaa ggc atg cta ggc      624
Ala Glu Lys Asp Met Cys Leu Ser Asp Ser Asn Lys Gly Met Leu Gly
        195                 200                 205 ctc atc gtc tac ctg ggc atg atg gtg gga gcc ttc ctc tgg gga ggt      672
Leu Ile Val Tyr Leu Gly Met Met Val Gly Ala Phe Leu Trp Gly Gly
210                 215                 220 ctg gct gac cgg ctg ggt cgg agg cag tgt ctg ctc atc tcg ctc tca      720
Leu Ala Asp Arg Leu Gly Arg Arg Gln Cys Leu Leu Ile Ser Leu Ser
225                 230                 235                 240 gtc aac agc gtc ttc gcc ttc ttc tca tct ttt gtc cag ggt tac ggc      768
Val Asn Ser Val Phe Ala Phe Phe Ser Ser Phe Val Gln Gly Tyr Gly
                245                 250                 255 act ttc ctc ttc tgc cgc cta ctt tct ggg gtt ggg att gga ggg tcc      816
Thr Phe Leu Phe Cys Arg Leu Leu Ser Gly Val Gly Ile Gly Gly Ser
                260                 265                 270 atc ccc att gtc ttc tcc tat ttc tcc gag ttt ctg gcc cag gag aaa      864
Ile Pro Ile Val Phe Ser Tyr Phe Ser Glu Phe Leu Ala Gln Glu Lys
                275                 280                 285 cga ggg gag cat ttg agc tgg ctc tgc atg ttt tgg atg att ggt ggc      912
Arg Gly Glu His Leu Ser Trp Leu Cys Met Phe Trp Met Ile Gly Gly
        290                 295                 300 gtg tac gca gct gct atg gcc tgg gcc atc atc ccc cac tat ggg tgg      960
Val Tyr Ala Ala Ala Met Ala Trp Ala Ile Ile Pro His Tyr Gly Trp
305                 310                 315                 320 agt ttt cag atg ggt tct gcc tac cag ttc cac agc tgg agg gtc ttc     1008
Ser Phe Gln Met Gly Ser Ala Tyr Gln Phe His Ser Trp Arg Val Phe
                325                 330                 335 gtc ctc gtc tgc gcc ttt cct tct gtg ttt gcc att ggg gct ctg acc     1056
Val Leu Val Cys Ala Phe Pro Ser Val Phe Ala Ile Gly Ala Leu Thr
                340                 345                 350 acg cag cct gag agc ccc cgt ttc ttc cta gag aat gga aag cat gat     1104
Thr Gln Pro Glu Ser Pro Arg Phe Phe Leu Glu Asn Gly Lys His Asp
                355                 360                 365 gag gcc tgg atg gtg ctg aag cag gtc cat gat acc aac atg cga gcc     1152
Glu Ala Trp Met Val Leu Lys Gln Val His Asp Thr Asn Met Arg Ala
        370                 375                 380 aaa gga cat cct gag cga gtg ttc tca gta acc cac att aag acg att     1200
Lys Gly His Pro Glu Arg Val Phe Ser Val Thr His Ile Lys Thr Ile
385                 390                 395                 400 cat cag gag gat gaa ttg att gag atc cag tcg gac aca ggg acc tgg     1248
His Gln Glu Asp Glu Leu Ile Glu Ile Gln Ser Asp Thr Gly Thr Trp
                405                 410                 415 tac cag cgc tgg ggg gtc cgg gcc ttg agc cta ggg ggg cag gtt tgg     1296
Tyr Gln Arg Trp Gly Val Arg Ala Leu Ser Leu Gly Gly Gln Val Trp
                420                 425                 430 ggg aat ttt ctc tcc tgt ttt ggt ccc gaa tat cgg cgc atc act ctg     1344
Gly Asn Phe Leu Ser Cys Phe Gly Pro Glu Tyr Arg Arg Ile Thr Leu
                435                 440                 445 atg atg atg ggt gtg tgg ttc acc atg tca ttc agc tac tat ggc ctg     1392
Met Met Met Gly Val Trp Phe Thr Met Ser Phe Ser Tyr Tyr Gly Leu
450                 455                 460 acc gtc tgg ttt cct gac atg atc cgc cat ctc cag gca gtg gac tac     1440
Thr Val Trp Phe Pro Asp Met Ile Arg His Leu Gln Ala Val Asp Tyr
465                 470                 475                 480 gca tcc cgc acc aaa gtg ttc ccc ggg gag cgc gta gag cat gta act     1488
Ala Ser Arg Thr Lys Val Phe Pro Gly Glu Arg Val Glu His Val Thr
                485                 490                 495 ttt aac ttc acg ttg gag aat cag atc cac cga ggc ggg cag tac ttc     1536
```

```
Phe Asn Phe Thr Leu Glu Asn Gln Ile His Arg Gly Gly Gln Tyr Phe
            500                 505                 510 aat gac aag ttc att ggg ctg cgg ctc aag tca gtg tcc ttt gag gat    1584
Asn Asp Lys Phe Ile Gly Leu Arg Leu Lys Ser Val Ser Phe Glu Asp
            515                 520                 525 tcc ctg ttt gaa gag tgt tat ttt gag gat gtc aca tcc agc aac acg    1632
Ser Leu Phe Glu Glu Cys Tyr Phe Glu Asp Val Thr Ser Ser Asn Thr
        530                 535                 540 ttt ttc cgc aac tgc aca ttc atc aac act gtg ttc tat aac act gac    1680
Phe Phe Arg Asn Cys Thr Phe Ile Asn Thr Val Phe Tyr Asn Thr Asp
545                 550                 555                 560 ctg ttc gag tac aag ttt gtg aac agc cgt ctg ata aac agt aca ttc    1728
Leu Phe Glu Tyr Lys Phe Val Asn Ser Arg Leu Ile Asn Ser Thr Phe
                565                 570                 575 ctg cac aac aag gag ggc tgc ccg cta gac gtg aca ggg acg ggc gaa    1776
Leu His Asn Lys Glu Gly Cys Pro Leu Asp Val Thr Gly Thr Gly Glu
            580                 585                 590 ggt gcc tac atg gta tac ttt gtg agc ttc ctg ggg aca ctg gca gtg    1824
Gly Ala Tyr Met Val Tyr Phe Val Ser Phe Leu Gly Thr Leu Ala Val
        595                 600                 605 ctt cct ggg aat atc gtg tct gcc ctg ctc atg gac aag atc ggc agg    1872
Leu Pro Gly Asn Ile Val Ser Ala Leu Leu Met Asp Lys Ile Gly Arg
610                 615                 620 ctc aga atg ctt gct ggc tcc agc gtg atg tcc tgt gtc tcc tgc ttc    1920
Leu Arg Met Leu Ala Gly Ser Ser Val Met Ser Cys Val Ser Cys Phe
625                 630                 635                 640 ttc ctg tct ttt ggg aac agt gag tcg gcc atg atc gct ctg ctc tgc    1968
Phe Leu Ser Phe Gly Asn Ser Glu Ser Ala Met Ile Ala Leu Leu Cys
                645                 650                 655 ctt ttt ggc ggg gtc agc att gca tcc tgg aat gcg ctg gac gtg ttg    2016
Leu Phe Gly Gly Val Ser Ile Ala Ser Trp Asn Ala Leu Asp Val Leu
            660                 665                 670 act gtt gaa ctc tac ccc tca gac aag agg acc aca gct ttt ggc ttc    2064
Thr Val Glu Leu Tyr Pro Ser Asp Lys Arg Thr Thr Ala Phe Gly Phe
        675                 680                 685 ctg aat gcc ctg tgt aag ctg gca gct gtg ctg ggg atc agc atc ttc    2112
Leu Asn Ala Leu Cys Lys Leu Ala Ala Val Leu Gly Ile Ser Ile Phe
690                 695                 700 aca tcc ttc gtg gga atc acc aag gct gca ccc atc ctc ttt gcc tca    2160
Thr Ser Phe Val Gly Ile Thr Lys Ala Ala Pro Ile Leu Phe Ala Ser
705                 710                 715                 720 gct gcc ctt gcc ctt ggc agc tct ctg gcc ctg aag ctg cct gag acc    2208
Ala Ala Leu Ala Leu Gly Ser Ser Leu Ala Leu Lys Leu Pro Glu Thr
                725                 730                 735 cgg ggg cag gtg ctg cag tga                                        2229
Arg Gly Gln Val Leu Gln
            740

<210> SEQ ID NO 2
<211> LENGTH: 742
<212> TYPE: PRT
<213> ORGANISM: Homo sapiens

<400> SEQUENCE: 2

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45
```

```
Phe Glu Glu Asp Asp Asp Asp Phe Pro Ala Pro Ser Asp Gly
 50              55                  60

Tyr Tyr Arg Gly Glu Gly Thr Gln Asp Glu Glu Gly Gly Ala Ser
 65              70              75              80

Ser Asp Ala Thr Glu Gly His Asp Glu Asp Glu Ile Tyr Glu Gly
             85              90              95

Glu Tyr Gln Gly Ile Pro Arg Ala Glu Ser Gly Gly Lys Gly Glu Arg
             100             105             110

Met Ala Asp Gly Ala Pro Leu Ala Gly Val Arg Gly Gly Leu Ser Asp
         115             120             125

Gly Glu Gly Pro Pro Gly Gly Arg Gly Glu Ala Gln Arg Arg Lys Glu
 130             135             140

Arg Glu Glu Leu Ala Gln Gln Tyr Glu Ala Ile Leu Arg Glu Cys Gly
 145             150             155             160

His Gly Arg Phe Gln Trp Thr Leu Tyr Phe Val Leu Gly Leu Ala Leu
             165             170             175

Met Ala Asp Gly Val Glu Val Phe Val Val Gly Phe Val Leu Pro Ser
             180             185             190

Ala Glu Lys Asp Met Cys Leu Ser Asp Ser Asn Lys Gly Met Leu Gly
         195             200             205

Leu Ile Val Tyr Leu Gly Met Met Val Gly Ala Phe Leu Trp Gly Gly
 210             215             220

Leu Ala Asp Arg Leu Gly Arg Arg Gln Cys Leu Leu Ile Ser Leu Ser
 225             230             235             240

Val Asn Ser Val Phe Ala Phe Phe Ser Ser Phe Val Gln Gly Tyr Gly
             245             250             255

Thr Phe Leu Phe Cys Arg Leu Leu Ser Gly Val Gly Ile Gly Gly Ser
             260             265             270

Ile Pro Ile Val Phe Ser Tyr Phe Ser Glu Phe Leu Ala Gln Glu Lys
             275             280             285

Arg Gly Glu His Leu Ser Trp Leu Cys Met Phe Trp Met Ile Gly Gly
 290             295             300

Val Tyr Ala Ala Ala Met Ala Trp Ala Ile Ile Pro His Tyr Gly Trp
 305             310             315             320

Ser Phe Gln Met Gly Ser Ala Tyr Gln Phe His Ser Trp Arg Val Phe
             325             330             335

Val Leu Val Cys Ala Phe Pro Ser Val Phe Ala Ile Gly Ala Leu Thr
             340             345             350

Thr Gln Pro Glu Ser Pro Arg Phe Phe Leu Glu Asn Gly Lys His Asp
         355             360             365

Glu Ala Trp Met Val Leu Lys Gln Val His Asp Thr Asn Met Arg Ala
 370             375             380

Lys Gly His Pro Glu Arg Val Phe Ser Val Thr His Ile Lys Thr Ile
 385             390             395             400

His Gln Glu Asp Glu Leu Ile Glu Ile Gln Ser Asp Thr Gly Thr Trp
             405             410             415

Tyr Gln Arg Trp Gly Val Arg Ala Leu Ser Leu Gly Gly Gln Val Trp
             420             425             430

Gly Asn Phe Leu Ser Cys Phe Gly Pro Glu Tyr Arg Arg Ile Thr Leu
         435             440             445

Met Met Met Gly Val Trp Phe Thr Met Ser Phe Ser Tyr Tyr Gly Leu
 450             455             460
```

-continued

```
Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740
```

<210> SEQ ID NO 3
<211> LENGTH: 2052
<212> TYPE: DNA
<213> ORGANISM: Homo sapiens
<220> FEATURE:
<221> NAME/KEY: CDS
<222> LOCATION: (1)..(2052)
<223> OTHER INFORMATION:

<400> SEQUENCE: 3

```
atg gat gac tac aag tat cag gac aat tat ggg ggc tat gct ccc agt      48
Met Asp Asp Tyr Lys Tyr Gln Asp Asn Tyr Gly Gly Tyr Ala Pro Ser
1               5                   10                  15 gat ggc tat tac cgc ggc aat gag tcc aac cca gaa gaa gat gca cag      96
Asp Gly Tyr Tyr Arg Gly Asn Glu Ser Asn Pro Glu Glu Asp Ala Gln
            20                  25                  30 agt gat gtc acc gaa ggc cat gat gag gaa gac gag atc tat gag ggc     144
Ser Asp Val Thr Glu Gly His Asp Glu Glu Asp Glu Ile Tyr Glu Gly
        35                  40                  45 gag tac cag ggt atc cct cac cca gat gat gtc aag gcc aag cag gcc     192
```

```
Glu Tyr Gln Gly Ile Pro His Pro Asp Asp Val Lys Ala Lys Gln Ala
    50              55                  60 aag atg gcg ccc tcc aga atg gac agc ctt cgg ggc cag aca gac ctg      240
Lys Met Ala Pro Ser Arg Met Asp Ser Leu Arg Gly Gln Thr Asp Leu
65              70                  75                  80 atg gct gag agg ctg gaa gat gag gag cag ttg gcc cac cag tac gag      288
Met Ala Glu Arg Leu Glu Asp Glu Glu Gln Leu Ala His Gln Tyr Glu
                85                  90                  95 acc atc atg gat gag tgt ggc cat ggc cgc ttc cag tgg atc ctc ttt      336
Thr Ile Met Asp Glu Cys Gly His Gly Arg Phe Gln Trp Ile Leu Phe
            100                 105                 110 ttc gtc ttg ggt ttg gcc ctg atg gcc gat ggg gtg gaa gtg ttc gtg      384
Phe Val Leu Gly Leu Ala Leu Met Ala Asp Gly Val Glu Val Phe Val
        115                 120                 125 gtg agt ttt gcc ctg ccc agt gca gag aag gac atg tgt ctg tcc agt      432
Val Ser Phe Ala Leu Pro Ser Ala Glu Lys Asp Met Cys Leu Ser Ser
    130                 135                 140 tcc aaa aaa gga atg cta ggg atg ata gtc tac ttg gga atg atg gcg      480
Ser Lys Lys Gly Met Leu Gly Met Ile Val Tyr Leu Gly Met Met Ala
145             150                 155                 160 ggc gcc ttc atc ctg gga ggc ctg gct gat aag ctg gga agg aag cga      528
Gly Ala Phe Ile Leu Gly Gly Leu Ala Asp Lys Leu Gly Arg Lys Arg
                165                 170                 175 gtc ctc agc atg tct ctg gcc gtc aat gcc tcc ttc gcc tcc ctc tct      576
Val Leu Ser Met Ser Leu Ala Val Asn Ala Ser Phe Ala Ser Leu Ser
            180                 185                 190 tcc ttc gtg cag gga tat gga gcc ttc ctc ttc tgc cga ctc atc tca      624
Ser Phe Val Gln Gly Tyr Gly Ala Phe Leu Phe Cys Arg Leu Ile Ser
        195                 200                 205 ggc atc ggt att ggg ggt gct cta ccg att gtt ttt gcc tat ttt tct      672
Gly Ile Gly Ile Gly Gly Ala Leu Pro Ile Val Phe Ala Tyr Phe Ser
    210                 215                 220 gaa ttc ttg tct cgg gag aag cga gga gaa cac ctc agt tgg ctg ggc      720
Glu Phe Leu Ser Arg Glu Lys Arg Gly Glu His Leu Ser Trp Leu Gly
225             230                 235                 240 atc ttc tgg atg act ggg ggc ctg tac gca tct gcc atg gcc tgg agc      768
Ile Phe Trp Met Thr Gly Gly Leu Tyr Ala Ser Ala Met Ala Trp Ser
                245                 250                 255 atc atc cca cac tat ggc tgg ggc ttc agc atg ggg acc aat tac cac      816
Ile Ile Pro His Tyr Gly Trp Gly Phe Ser Met Gly Thr Asn Tyr His
            260                 265                 270 ttc cat agc tgg aga gtg ttt gtc atc gtc tgt gct ctg ccc tgc acc      864
Phe His Ser Trp Arg Val Phe Val Ile Val Cys Ala Leu Pro Cys Thr
        275                 280                 285 gtg tcc atg gtg gcc ctg aag ttc atg cca gag agc cca agg ttt ctg      912
Val Ser Met Val Ala Leu Lys Phe Met Pro Glu Ser Pro Arg Phe Leu
    290                 295                 300 cta gag atg ggc aaa cat gat gaa gcc tgg atg att ctc aag caa gtc      960
Leu Glu Met Gly Lys His Asp Glu Ala Trp Met Ile Leu Lys Gln Val
305             310                 315                 320 cat gac acc aac atg aga gct aag ggg acc cca gag aaa gtg ttc acg     1008
His Asp Thr Asn Met Arg Ala Lys Gly Thr Pro Glu Lys Val Phe Thr
                325                 330                 335 gtt tcc aac atc aaa act ccc aag caa atg gat gaa ttc att gag atc     1056
Val Ser Asn Ile Lys Thr Pro Lys Gln Met Asp Glu Phe Ile Glu Ile
            340                 345                 350 caa agt tca aca gga acc tgg tac cag cgc tgg ctg gtc aga ttc aag     1104
Gln Ser Ser Thr Gly Thr Trp Tyr Gln Arg Trp Leu Val Arg Phe Lys
        355                 360                 365
```

```
acc att ttc aag cag gtc tgg gat aat gcc ctg tac tgt gtg atg ggg      1152
Thr Ile Phe Lys Gln Val Trp Asp Asn Ala Leu Tyr Cys Val Met Gly
    370                 375                 380 ccc tac aga atg aat aca ctg att ctg gcc gtg gtt tgg ttt gcc atg      1200
Pro Tyr Arg Met Asn Thr Leu Ile Leu Ala Val Val Trp Phe Ala Met
385                 390                 395                 400 gca ttc agt tac tat gga ctg aca gtt tgg ttt cct gat atg atc cgc      1248
Ala Phe Ser Tyr Tyr Gly Leu Thr Val Trp Phe Pro Asp Met Ile Arg
                405                 410                 415 tat ttt caa gat gaa gaa tac aag tct aaa atg aag gtg ttt ttt ggt      1296
Tyr Phe Gln Asp Glu Glu Tyr Lys Ser Lys Met Lys Val Phe Phe Gly
            420                 425                 430 gag cat gtg tac ggc gcc aca atc aac ttc acg atg gaa aat cag atc      1344
Glu His Val Tyr Gly Ala Thr Ile Asn Phe Thr Met Glu Asn Gln Ile
        435                 440                 445 cac caa cat ggg aaa ctt gtg aat gat aag ttc aca aga atg tac ttt      1392
His Gln His Gly Lys Leu Val Asn Asp Lys Phe Thr Arg Met Tyr Phe
    450                 455                 460 aaa cat gta ctc ttt gag gac aca ttc ttt gac gag tgc tat ttt gaa      1440
Lys His Val Leu Phe Glu Asp Thr Phe Phe Asp Glu Cys Tyr Phe Glu
465                 470                 475                 480 gac gta aca tca aca gat acc tac ttc aaa aat tgt acc att gaa tca      1488
Asp Val Thr Ser Thr Asp Thr Tyr Phe Lys Asn Cys Thr Ile Glu Ser
                485                 490                 495 acc atc ttt tac aac aca gac ctc tac gag cac aag ttc atc aac tgt      1536
Thr Ile Phe Tyr Asn Thr Asp Leu Tyr Glu His Lys Phe Ile Asn Cys
            500                 505                 510 cgg ttt atc aac tcc acc ttc ctg gag cag aag gag ggc tgc cac atg      1584
Arg Phe Ile Asn Ser Thr Phe Leu Glu Gln Lys Glu Gly Cys His Met
        515                 520                 525 gac ttg gag caa gat aat gac ttc ctg att tac ctc gtc agc ttc ctg      1632
Asp Leu Glu Gln Asp Asn Asp Phe Leu Ile Tyr Leu Val Ser Phe Leu
    530                 535                 540 ggc agc ctg tct gtc tta ccc ggg aac atc att tct gcc ctg ctc atg      1680
Gly Ser Leu Ser Val Leu Pro Gly Asn Ile Ile Ser Ala Leu Leu Met
545                 550                 555                 560 gat aga att gga agg ctc aag atg att ggt ggc tcc atg cta atc tct      1728
Asp Arg Ile Gly Arg Leu Lys Met Ile Gly Gly Ser Met Leu Ile Ser
                565                 570                 575 gca gtc tgc tgc ttc ttc ctg ttt ggc aac agt gag tct gca atg          1776
Ala Val Cys Cys Phe Phe Leu Phe Gly Asn Ser Glu Ser Ala Met
            580                 585                 590 atc ggc tgg cag tgc ctg ttc tgt ggg aca agc att gca gcc tgg aat      1824
Ile Gly Trp Gln Cys Leu Phe Cys Gly Thr Ser Ile Ala Ala Trp Asn
        595                 600                 605 gct ctg gat gtg atc aca gtg gag ctg tat ccc acc aac cag aga gca      1872
Ala Leu Asp Val Ile Thr Val Glu Leu Tyr Pro Thr Asn Gln Arg Ala
    610                 615                 620 aca gcc ttc ggc att ctc aat gga tta tgc aaa ttt ggc gcc atc ctg      1920
Thr Ala Phe Gly Ile Leu Asn Gly Leu Cys Lys Phe Gly Ala Ile Leu
625                 630                 635                 640 gga aac acc atc ttt gct tct ttt gtt ggg ata acc aaa gtg gtc ccc      1968
Gly Asn Thr Ile Phe Ala Ser Phe Val Gly Ile Thr Lys Val Val Pro
                645                 650                 655 atc ctt ctg gct gct gct tct ctg gtt ggg ggt ggc ctg att gcc ctt      2016
Ile Leu Leu Ala Ala Ala Ser Leu Val Gly Gly Gly Leu Ile Ala Leu
            660                 665                 670 cga ctg cca gag act cga gaa cag gtc ctg atg tga                      2052
Arg Leu Pro Glu Thr Arg Glu Gln Val Leu Met
        675                 680
```

-continued

```
<210> SEQ ID NO 4
<211> LENGTH: 683
<212> TYPE: PRT
<213> ORGANISM: Homo sapiens

<400> SEQUENCE: 4

Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Glu Gln Leu Ala His Gln Tyr Glu
                85                  90                  95

Thr Ile Met Asp Glu Cys Gly His Gly Arg Phe Gln Trp Ile Leu Phe
            100                 105                 110

Phe Val Leu Gly Leu Ala Leu Met Ala Asp Gly Val Glu Val Phe Val
        115                 120                 125

Val Ser Phe Ala Leu Pro Ser Ala Glu Lys Asp Met Cys Leu Ser Ser
    130                 135                 140

Ser Lys Lys Gly Met Leu Gly Met Ile Val Tyr Leu Gly Met Met Ala
145                 150                 155                 160

Gly Ala Phe Ile Leu Gly Gly Leu Ala Asp Lys Leu Gly Arg Lys Arg
                165                 170                 175

Val Leu Ser Met Ser Leu Ala Val Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ala Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Cys Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser Asn Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Lys
        355                 360                 365

Thr Ile Phe Lys Gln Val Trp Asp Asn Ala Leu Tyr Cys Val Met Gly
```

```
                    370                 375                 380
Pro Tyr Arg Met Asn Thr Leu Ile Leu Ala Val Val Trp Phe Ala Met
385                 390                 395                 400

Ala Phe Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430

Glu His Val Tyr Gly Ala Thr Ile Asn Phe Thr Met Glu Asn Gln Ile
        435                 440                 445

His Gln His Gly Lys Leu Val Asn Asp Lys Phe Thr Arg Met Tyr Phe
    450                 455                 460

Lys His Val Leu Phe Glu Asp Thr Phe Phe Asp Glu Cys Tyr Phe Glu
465                 470                 475                 480

Asp Val Thr Ser Thr Asp Thr Tyr Phe Lys Asn Cys Thr Ile Glu Ser
                485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
        515                 520                 525

Asp Leu Glu Gln Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
            660                 665                 670

Arg Leu Pro Glu Thr Arg Glu Gln Val Leu Met
        675                 680

<210> SEQ ID NO 5
<211> LENGTH: 2184
<212> TYPE: DNA
<213> ORGANISM: Homo sapiens
<220> FEATURE:
<221> NAME/KEY: CDS
<222> LOCATION: (1)..(2184)
<223> OTHER INFORMATION:

<400> SEQUENCE: 5 atg gaa gac tct tac aag gat agg act tca ctg atg aag ggt gcc aag    48
Met Glu Asp Ser Tyr Lys Asp Arg Thr Ser Leu Met Lys Gly Ala Lys
1               5                   10                  15 gac att gcc aga gag gtg aag aaa caa aca gta aag aag gtg aat caa    96
Asp Ile Ala Arg Glu Val Lys Lys Gln Thr Val Lys Lys Val Asn Gln
            20                  25                  30
```

```
gct gtg gac cga gcc cag gat gaa tac acc cag agg tcc tac agt cgg      144
Ala Val Asp Arg Ala Gln Asp Glu Tyr Thr Gln Arg Ser Tyr Ser Arg
         35                  40                  45 ttc caa gat gaa gaa gat gat gat gac tac tac ccg gct gga gaa acc      192
Phe Gln Asp Glu Glu Asp Asp Asp Asp Tyr Tyr Pro Ala Gly Glu Thr
 50                  55                  60 tat aat ggt gag gcc aac gat gac gaa ggc tca agt gaa gcc act gag      240
Tyr Asn Gly Glu Ala Asn Asp Asp Glu Gly Ser Ser Glu Ala Thr Glu
 65                  70                  75                  80 ggg cat gat gaa gat gat gag atc tat gag ggg gag tat cag ggc atc      288
Gly His Asp Glu Asp Asp Glu Ile Tyr Glu Gly Glu Tyr Gln Gly Ile
                     85                  90                  95 ccc agt atg aac caa gcg aag gac agc atc gtg tca gtg ggg cag ccc      336
Pro Ser Met Asn Gln Ala Lys Asp Ser Ile Val Ser Val Gly Gln Pro
            100                 105                 110 aag ggc gat gag tac aag gac cga cgg gag ctg gaa tca gaa agg aga      384
Lys Gly Asp Glu Tyr Lys Asp Arg Arg Glu Leu Glu Ser Glu Arg Arg
        115                 120                 125 gct gac gag gaa gag tta gcc cag cag tat gag ctg ata atc caa gaa      432
Ala Asp Glu Glu Glu Leu Ala Gln Gln Tyr Glu Leu Ile Ile Gln Glu
130                 135                 140 tgc ggt cat ggt cgt ttt cag tgg gcc ctt ttc ttc gtc ctg ggc atg      480
Cys Gly His Gly Arg Phe Gln Trp Ala Leu Phe Phe Val Leu Gly Met
145                 150                 155                 160 gct ctt atg gca gac ggt gta gag gtg ttt gtc gtt ggc ttc gtg tta      528
Ala Leu Met Ala Asp Gly Val Glu Val Phe Val Val Gly Phe Val Leu
                    165                 170                 175 ccc agt gct gag aca gac ctc tgc atc cca aat tca gga tct gga tgg      576
Pro Ser Ala Glu Thr Asp Leu Cys Ile Pro Asn Ser Gly Ser Gly Trp
                180                 185                 190 cta ggc agc ata gtg tac ctc ggg atg atg gtg ggg gcg ttc ttc tgg      624
Leu Gly Ser Ile Val Tyr Leu Gly Met Met Val Gly Ala Phe Phe Trp
            195                 200                 205 gga gga ctg gca gac aaa gtg gga agg aaa cag tct ctt ctg att tgc      672
Gly Gly Leu Ala Asp Lys Val Gly Arg Lys Gln Ser Leu Leu Ile Cys
        210                 215                 220 atg tct gtc aac gga ttc ttt gcc ttc ctt tct tca ttt gtc caa ggt      720
Met Ser Val Asn Gly Phe Phe Ala Phe Leu Ser Ser Phe Val Gln Gly
225                 230                 235                 240 tat ggc ttc ttt ctc ttc tgt cgc tta ctt tct gga ttc ggg att gga      768
Tyr Gly Phe Phe Leu Phe Cys Arg Leu Leu Ser Gly Phe Gly Ile Gly
                    245                 250                 255 gga gcc ata ccc act gtg ttc tcg tac ttt gct gaa gtc ctg gcc cgg      816
Gly Ala Ile Pro Thr Val Phe Ser Tyr Phe Ala Glu Val Leu Ala Arg
                260                 265                 270 gaa aag cgg ggc gaa cac ttg agc tgg ctc tgc atg ttc tgg atg atc      864
Glu Lys Arg Gly Glu His Leu Ser Trp Leu Cys Met Phe Trp Met Ile
            275                 280                 285 ggt ggc atc tac gcc tct gcc atg gcc tgg gcc atc atc ccg cac tac      912
Gly Gly Ile Tyr Ala Ser Ala Met Ala Trp Ala Ile Ile Pro His Tyr
        290                 295                 300 ggg tgg agc ttc agc atg gga tcg gcc tac cag ttt cac agt tgg cgt      960
Gly Trp Ser Phe Ser Met Gly Ser Ala Tyr Gln Phe His Ser Trp Arg
305                 310                 315                 320 gtg ttt gtc atc gtc tgt gca ctc ccc tgt gtc tcc tcc gtg gtg gcc     1008
Val Phe Val Ile Val Cys Ala Leu Pro Cys Val Ser Ser Val Val Ala
                    325                 330                 335 ctc aca ttc atg cct gaa agc cca cga ttc ttg ttg gag gtt gga aaa     1056
Leu Thr Phe Met Pro Glu Ser Pro Arg Phe Leu Leu Glu Val Gly Lys
                340                 345                 350
```

```
cat gat gaa gct tgg atg att ctg aag tta att cat gac acc aac atg      1104
His Asp Glu Ala Trp Met Ile Leu Lys Leu Ile His Asp Thr Asn Met
        355                 360                 365 aga gcc cgg ggt cag cct gag aag gtc ttc acg gta aac aaa ata aaa      1152
Arg Ala Arg Gly Gln Pro Glu Lys Val Phe Thr Val Asn Lys Ile Lys
370                 375                 380 act cct aaa caa ata gat gag ctg att gaa att gag agt gac aca gga      1200
Thr Pro Lys Gln Ile Asp Glu Leu Ile Glu Ile Glu Ser Asp Thr Gly
385                 390                 395                 400 aca tgg tat agg agg tgt ttt gtt cgg atc cgc acc gag ctg tac gga      1248
Thr Trp Tyr Arg Arg Cys Phe Val Arg Ile Arg Thr Glu Leu Tyr Gly
            405                 410                 415 att tgg ttg act ttt atg aga tgt ttc aac tac cca gtc agg gat aat      1296
Ile Trp Leu Thr Phe Met Arg Cys Phe Asn Tyr Pro Val Arg Asp Asn
        420                 425                 430 aca ata aag ctt aca att gtt tgg ttc acc ctg tcc ttt ggg tac tat      1344
Thr Ile Lys Leu Thr Ile Val Trp Phe Thr Leu Ser Phe Gly Tyr Tyr
    435                 440                 445 gga tta tcc gtt tgg ttc cct gat gtc att aaa cct ctg cag tcc gat      1392
Gly Leu Ser Val Trp Phe Pro Asp Val Ile Lys Pro Leu Gln Ser Asp
450                 455                 460 gaa tat gca ttg cta acc aga aat gtg gag aga gat aaa tat gca aat      1440
Glu Tyr Ala Leu Leu Thr Arg Asn Val Glu Arg Asp Lys Tyr Ala Asn
465                 470                 475                 480 ttc act att aac ttt aca atg gaa aat cag att cat act gga atg gaa      1488
Phe Thr Ile Asn Phe Thr Met Glu Asn Gln Ile His Thr Gly Met Glu
            485                 490                 495 tac gac aat ggc aga ttc ata ggg gtc aag ttc aaa tct gta act ttc      1536
Tyr Asp Asn Gly Arg Phe Ile Gly Val Lys Phe Lys Ser Val Thr Phe
        500                 505                 510 aaa gac tct gtt ttt aag tcc tgc acc ttt gag gat gta act tca gtg      1584
Lys Asp Ser Val Phe Lys Ser Cys Thr Phe Glu Asp Val Thr Ser Val
    515                 520                 525 aac acc tac ttc aag aac tgc aca ttt att gac act gtt ttt gac aac      1632
Asn Thr Tyr Phe Lys Asn Cys Thr Phe Ile Asp Thr Val Phe Asp Asn
530                 535                 540 aca gat ttt gag cca tat aaa ttc att gac agt gaa ttt aaa aac tgc      1680
Thr Asp Phe Glu Pro Tyr Lys Phe Ile Asp Ser Glu Phe Lys Asn Cys
545                 550                 555                 560 tcg ttt ttt cac aac aag acg gga tgt cag att acc ttt gat gat gac      1728
Ser Phe Phe His Asn Lys Thr Gly Cys Gln Ile Thr Phe Asp Asp Asp
            565                 570                 575 tat agt gcc tac tgg att tat ttt gtc aac ttt ctg ggg aca ttg gca      1776
Tyr Ser Ala Tyr Trp Ile Tyr Phe Val Asn Phe Leu Gly Thr Leu Ala
        580                 585                 590 gta ttg cca ggg aac att gtg tct gct ctg ctg atg gac aga att ggg      1824
Val Leu Pro Gly Asn Ile Val Ser Ala Leu Leu Met Asp Arg Ile Gly
    595                 600                 605 cgc tta aca atg cta ggt ggc tct atg gtg ctt tcg ggg atc agc tgt      1872
Arg Leu Thr Met Leu Gly Gly Ser Met Val Leu Ser Gly Ile Ser Cys
610                 615                 620 ttc ttc ctt tgg ttc ggc acc agt gaa tcc atg atg ata ggc atg ctg      1920
Phe Phe Leu Trp Phe Gly Thr Ser Glu Ser Met Met Ile Gly Met Leu
625                 630                 635                 640 tgt ctg tac aat gga ttg acc atc tca gcc tgg aac tct ctt gac gtg      1968
Cys Leu Tyr Asn Gly Leu Thr Ile Ser Ala Trp Asn Ser Leu Asp Val
            645                 650                 655 gtc act gtg gaa ctg tac ccc aca gac cgg agg gca aca ggc ttt ggc      2016
Val Thr Val Glu Leu Tyr Pro Thr Asp Arg Arg Ala Thr Gly Phe Gly
```

-continued

```
                    660                 665                 670
ttc tta aat gcg cta tgc aag gca gca gcc gtc ctg gga aac tta ata    2064
Phe Leu Asn Ala Leu Cys Lys Ala Ala Ala Val Leu Gly Asn Leu Ile
        675                 680                 685 ttt ggc tct ctg gtc agc atc acc aaa tca atc ccc atc ctg ctg gct    2112
Phe Gly Ser Leu Val Ser Ile Thr Lys Ser Ile Pro Ile Leu Leu Ala
    690                 695                 700 tct act gtg ctc gtg tgt gga gga ctc gtt ggg ctg tgc ctg cct gac    2160
Ser Thr Val Leu Val Cys Gly Gly Leu Val Gly Leu Cys Leu Pro Asp
705                 710                 715                 720 aca cga acc cag gtt ctg atg taa                                    2184
Thr Arg Thr Gln Val Leu Met
                725
```

<210> SEQ ID NO 6
<211> LENGTH: 727
<212> TYPE: PRT
<213> ORGANISM: Homo sapiens

<400> SEQUENCE: 6

```
Met Glu Asp Ser Tyr Lys Asp Arg Thr Ser Leu Met Lys Gly Ala Lys
1               5                   10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Tyr Tyr Pro Ala Gly Glu Thr
    50                  55                  60

Tyr Asn Gly Glu Ala Asn Asp Asp Glu Gly Ser Ser Glu Ala Thr Glu
65              70                  75                  80

Gly His Asp Glu Asp Asp Glu Ile Tyr Glu Gly Glu Tyr Gln Gly Ile
                85                  90                  95

Pro Ser Met Asn Gln Ala Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Glu Leu Ala Gln Gln Tyr Glu Leu Ile Ile Gln Glu
    130                 135                 140

Cys Gly His Gly Arg Phe Gln Trp Ala Leu Phe Phe Val Leu Gly Met
145                 150                 155                 160

Ala Leu Met Ala Asp Gly Val Glu Val Phe Val Gly Phe Val Leu
                165                 170                 175

Pro Ser Ala Glu Thr Asp Leu Cys Ile Pro Asn Ser Gly Ser Gly Trp
            180                 185                 190

Leu Gly Ser Ile Val Tyr Leu Gly Met Met Val Gly Ala Phe Phe Trp
        195                 200                 205

Gly Gly Leu Ala Asp Lys Val Gly Arg Lys Gln Ser Leu Leu Ile Cys
    210                 215                 220

Met Ser Val Asn Gly Phe Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285
```

-continued

```
Gly Gly Ile Tyr Ala Ser Ala Met Ala Trp Ala Ile Ile Pro His Tyr
    290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                    325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
            355                 360                 365

Arg Ala Arg Gly Gln Pro Glu Lys Val Phe Thr Val Asn Lys Ile Lys
    370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
                420                 425                 430

Thr Ile Lys Leu Thr Ile Val Trp Phe Thr Leu Ser Phe Gly Tyr Tyr
            435                 440                 445

Gly Leu Ser Val Trp Phe Pro Asp Val Ile Lys Pro Leu Gln Ser Asp
    450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
                485                 490                 495

Tyr Asp Asn Gly Arg Phe Ile Gly Val Lys Phe Lys Ser Val Thr Phe
                500                 505                 510

Lys Asp Ser Val Phe Lys Ser Cys Thr Phe Glu Asp Val Thr Ser Val
            515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
                580                 585                 590

Val Leu Pro Gly Asn Ile Val Ser Ala Leu Leu Met Asp Arg Ile Gly
            595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
                660                 665                 670

Phe Leu Asn Ala Leu Cys Lys Ala Ala Ala Val Leu Gly Asn Leu Ile
            675                 680                 685

Phe Gly Ser Leu Val Ser Ile Thr Lys Ser Ile Pro Ile Leu Leu Ala
    690                 695                 700
```

```
Ser Thr Val Leu Val Cys Gly Gly Leu Val Gly Cys Leu Pro Asp
705                 710                 715                 720

Thr Arg Thr Gln Val Leu Met
                725

<210> SEQ ID NO 7
<211> LENGTH: 1647
<212> TYPE: DNA
<213> ORGANISM: Homo sapiens
<220> FEATURE:
<221> NAME/KEY: CDS
<222> LOCATION: (1)..(1647)
<223> OTHER INFORMATION:

<400> SEQUENCE: 7 atg gag gag gac tta ttc cag cta agg cag ctg ccg gtt gtg aaa ttc      48
Met Glu Glu Asp Leu Phe Gln Leu Arg Gln Leu Pro Val Val Lys Phe
1               5                   10                  15 cgt cgc aca ggc gag agt gca agg tca gag gac gac acg gct tca gga      96
Arg Arg Thr Gly Glu Ser Ala Arg Ser Glu Asp Asp Thr Ala Ser Gly
            20                  25                  30 gag cat gaa gtc cag att gaa ggg gtc cac gtg ggc cta gag gct gtg     144
Glu His Glu Val Gln Ile Glu Gly Val His Val Gly Leu Glu Ala Val
        35                  40                  45 gag ctg gat gat ggg gca gct gtg ccc aag gag ttt gcc aat ccc act     192
Glu Leu Asp Asp Gly Ala Ala Val Pro Lys Glu Phe Ala Asn Pro Thr
    50                  55                  60 gat gat act ttc atg gtg gaa gat gca gtg gaa gcc att ggc ttt gga     240
Asp Asp Thr Phe Met Val Glu Asp Ala Val Glu Ala Ile Gly Phe Gly
65                  70                  75                  80 aaa ttt cag tgg aag ctg tct gtt ctc act ggc ttg gct tgg atg gct     288
Lys Phe Gln Trp Lys Leu Ser Val Leu Thr Gly Leu Ala Trp Met Ala
                85                  90                  95 gat gcc atg gag atg atg atc ctc agc atc ctg gca cca cag ctg cat     336
Asp Ala Met Glu Met Met Ile Leu Ser Ile Leu Ala Pro Gln Leu His
            100                 105                 110 tgc gag tgg agg ctc cca agc tgg cag gtg gca ttg ctg acc tcg gtg     384
Cys Glu Trp Arg Leu Pro Ser Trp Gln Val Ala Leu Leu Thr Ser Val
        115                 120                 125 gtc ttt gta ggc atg atg tcc agc tcc acg ctc tgg gga aat atc tca     432
Val Phe Val Gly Met Met Ser Ser Ser Thr Leu Trp Gly Asn Ile Ser
    130                 135                 140 gac cag tac ggc agg aaa aca ggg ctg aag atc agc gtg ctg tgg act     480
Asp Gln Tyr Gly Arg Lys Thr Gly Leu Lys Ile Ser Val Leu Trp Thr
145                 150                 155                 160 ctg tac tat ggc atc ctt agt gca ttt gcg ccc gtg tat agc tgg atc     528
Leu Tyr Tyr Gly Ile Leu Ser Ala Phe Ala Pro Val Tyr Ser Trp Ile
                165                 170                 175 ctg gtg ctc cgg ggc ctg gtg ggc ttc ggg atc gga gga gtt ccc cag     576
Leu Val Leu Arg Gly Leu Val Gly Phe Gly Ile Gly Gly Val Pro Gln
            180                 185                 190 tcg gtg acg ctg tat gcc gag ttc ctt ccc atg aaa gcc aga gct aaa     624
Ser Val Thr Leu Tyr Ala Glu Phe Leu Pro Met Lys Ala Arg Ala Lys
        195                 200                 205 tgt att ttg ctg att gag gta ttc tgg gcc atc ggg aca gtg ttc gag     672
Cys Ile Leu Leu Ile Glu Val Phe Trp Ala Ile Gly Thr Val Phe Glu
    210                 215                 220 gtc gtc ctg gct gtg ttc gtg atg ccc agc ctg ggc tgg cgt tgg ctg     720
Val Val Leu Ala Val Phe Val Met Pro Ser Leu Gly Trp Arg Trp Leu
225                 230                 235                 240 ctc atc ctc tca gct gtc ccg ctc ctc ctc ttt gcc gtg ctg tgt ttc     768
```

```
        Leu Ile Leu Ser Ala Val Pro Leu Leu Leu Phe Ala Val Leu Cys Phe
                        245                 250                 255 tgg ctg cct gaa agt gca agg tat gat gtg ctg tca ggg aac cag gaa          816
Trp Leu Pro Glu Ser Ala Arg Tyr Asp Val Leu Ser Gly Asn Gln Glu
            260                 265                 270 aag gca atc gcc acc tta aag agg ata gca act gaa aac gga gct ccc          864
Lys Ala Ile Ala Thr Leu Lys Arg Ile Ala Thr Glu Asn Gly Ala Pro
        275                 280                 285 atg ccg ctg ggg aaa ctc atc atc tcc aga cag gaa gac cga ggc aaa          912
Met Pro Leu Gly Lys Leu Ile Ile Ser Arg Gln Glu Asp Arg Gly Lys
    290                 295                 300 atg agg gac ctt ttc aca ccc cat ttt aga tgg aca act ttg ctg ctg          960
Met Arg Asp Leu Phe Thr Pro His Phe Arg Trp Thr Thr Leu Leu Leu
305                 310                 315                 320 tgg ttt ata tgg ttt tcc aat gca ttc tct tac tac ggg tta gtt cta         1008
Trp Phe Ile Trp Phe Ser Asn Ala Phe Ser Tyr Tyr Gly Leu Val Leu
                325                 330                 335 ctc acc aca gaa ctc ttc cag gca gga gat gtc tgc ggc atc tcc agt         1056
Leu Thr Thr Glu Leu Phe Gln Ala Gly Asp Val Cys Gly Ile Ser Ser
            340                 345                 350 cgg aag aag gct gta gag gca aaa tgc agc ctg gcc tgc gag tac ctg         1104
Arg Lys Lys Ala Val Glu Ala Lys Cys Ser Leu Ala Cys Glu Tyr Leu
        355                 360                 365 agt gag gag gat tac atg gac ttg ctg tgg acc acc ctc tct gag ttt         1152
Ser Glu Glu Asp Tyr Met Asp Leu Leu Trp Thr Thr Leu Ser Glu Phe
    370                 375                 380 cca ggt gtc ctt gtg act ctg tgg att att gac cgc ctg ggg cgc aag         1200
Pro Gly Val Leu Val Thr Leu Trp Ile Ile Asp Arg Leu Gly Arg Lys
385                 390                 395                 400 aag acc atg gcc ctg tgc ttt gtc atc ttc tcc ttc tgc agc ctc ctg         1248
Lys Thr Met Ala Leu Cys Phe Val Ile Phe Ser Phe Cys Ser Leu Leu
                405                 410                 415 ctg ttt atc tgt gtt gga aga aat gtg ctc act ctg tta ctc ttc att         1296
Leu Phe Ile Cys Val Gly Arg Asn Val Leu Thr Leu Leu Leu Phe Ile
            420                 425                 430 gca aga gcg ttt att tct gga ggc ttt caa gcg gca tat gtt tac aca         1344
Ala Arg Ala Phe Ile Ser Gly Gly Phe Gln Ala Ala Tyr Val Tyr Thr
        435                 440                 445 cct gag gtc tac ccc acg gca acg cgg gcc ctc ggc ctg ggc acc tgc         1392
Pro Glu Val Tyr Pro Thr Ala Thr Arg Ala Leu Gly Leu Gly Thr Cys
    450                 455                 460 agc ggc atg gca aga gtg ggt gct ctc atc act ccg ttc atc gcc cag         1440
Ser Gly Met Ala Arg Val Gly Ala Leu Ile Thr Pro Phe Ile Ala Gln
465                 470                 475                 480 gtg atg ctg gaa tcc tct gtg tac ctg act ctg gca gtt tac agt ggc         1488
Val Met Leu Glu Ser Ser Val Tyr Leu Thr Leu Ala Val Tyr Ser Gly
                485                 490                 495 tgc tgc ctc ctg gct gcc ctg gcc tcc tgc ttt ttg ccc att gag acc         1536
Cys Cys Leu Leu Ala Ala Leu Ala Ser Cys Phe Leu Pro Ile Glu Thr
            500                 505                 510 aaa ggc cga gga ctg cag gag tcc agc cac cgg gag tgg ggc cag gag         1584
Lys Gly Arg Gly Leu Gln Glu Ser Ser His Arg Glu Trp Gly Gln Glu
        515                 520                 525 atg gtc ggc cga gga atg cac ggt gca ggt gtt acc agg tcg aac tct         1632
Met Val Gly Arg Gly Met His Gly Ala Gly Val Thr Arg Ser Asn Ser
    530                 535                 540 ggc tct cag gaa tag                                                      1647
Gly Ser Gln Glu
545
```

<210> SEQ ID NO 8
<211> LENGTH: 548
<212> TYPE: PRT
<213> ORGANISM: Homo sapiens

<400> SEQUENCE: 8

```
Met Glu Glu Asp Leu Phe Gln Leu Arg Gln Leu Pro Val Val Lys Phe
1               5                  10                  15

Arg Arg Thr Gly Glu Ser Ala Arg Ser Glu Asp Asp Thr Ala Ser Gly
            20                  25                  30

Glu His Glu Val Gln Ile Glu Gly Val His Val Gly Leu Glu Ala Val
        35                  40                  45

Glu Leu Asp Asp Gly Ala Ala Val Pro Lys Glu Phe Ala Asn Pro Thr
    50                  55                  60

Asp Asp Thr Phe Met Val Glu Asp Ala Val Glu Ala Ile Gly Phe Gly
65                  70                  75                  80

Lys Phe Gln Trp Lys Leu Ser Val Leu Thr Gly Leu Ala Trp Met Ala
                85                  90                  95

Asp Ala Met Glu Met Met Ile Leu Ser Ile Leu Ala Pro Gln Leu His
            100                 105                 110

Cys Glu Trp Arg Leu Pro Ser Trp Gln Val Ala Leu Leu Thr Ser Val
        115                 120                 125

Val Phe Val Gly Met Met Ser Ser Thr Leu Trp Gly Asn Ile Ser
    130                 135                 140

Asp Gln Tyr Gly Arg Lys Thr Gly Leu Lys Ile Ser Val Leu Trp Thr
145                 150                 155                 160

Leu Tyr Tyr Gly Ile Leu Ser Ala Phe Ala Pro Val Tyr Ser Trp Ile
                165                 170                 175

Leu Val Leu Arg Gly Leu Val Gly Phe Gly Ile Gly Gly Val Pro Gln
            180                 185                 190

Ser Val Thr Leu Tyr Ala Glu Phe Leu Pro Met Lys Ala Arg Ala Lys
        195                 200                 205

Cys Ile Leu Leu Ile Glu Val Phe Trp Ala Ile Gly Thr Val Phe Glu
    210                 215                 220

Val Val Leu Ala Val Phe Val Met Pro Ser Leu Gly Trp Arg Trp Leu
225                 230                 235                 240

Leu Ile Leu Ser Ala Val Pro Leu Leu Phe Ala Val Leu Cys Phe
                245                 250                 255

Trp Leu Pro Glu Ser Ala Arg Tyr Asp Val Leu Ser Gly Asn Gln Glu
            260                 265                 270

Lys Ala Ile Ala Thr Leu Lys Arg Ile Ala Thr Glu Asn Gly Ala Pro
        275                 280                 285

Met Pro Leu Gly Lys Leu Ile Ile Ser Arg Gln Glu Asp Arg Gly Lys
    290                 295                 300

Met Arg Asp Leu Phe Thr Pro His Phe Arg Trp Thr Thr Leu Leu Leu
305                 310                 315                 320

Trp Phe Ile Trp Phe Ser Asn Ala Phe Ser Tyr Tyr Gly Leu Val Leu
                325                 330                 335

Leu Thr Thr Glu Leu Phe Gln Ala Gly Asp Val Cys Gly Ile Ser Ser
            340                 345                 350

Arg Lys Lys Ala Val Glu Ala Lys Cys Ser Leu Ala Cys Glu Tyr Leu
        355                 360                 365

Ser Glu Glu Asp Tyr Met Asp Leu Leu Trp Thr Thr Leu Ser Glu Phe
    370                 375                 380
```

-continued

```
Pro Gly Val Leu Val Thr Leu Trp Ile Ile Asp Arg Leu Gly Arg Lys
385                 390                 395                 400

Lys Thr Met Ala Leu Cys Phe Val Ile Phe Ser Phe Cys Ser Leu Leu
            405                 410                 415

Leu Phe Ile Cys Val Gly Arg Asn Val Leu Thr Leu Leu Phe Ile
        420                 425                 430

Ala Arg Ala Phe Ile Ser Gly Phe Gln Ala Ala Tyr Val Tyr Thr
            435                 440                 445

Pro Glu Val Tyr Pro Thr Ala Thr Arg Ala Leu Gly Leu Gly Thr Cys
    450                 455                 460

Ser Gly Met Ala Arg Val Gly Ala Leu Ile Thr Pro Phe Ile Ala Gln
465                 470                 475                 480

Val Met Leu Glu Ser Ser Val Tyr Leu Thr Leu Ala Val Tyr Ser Gly
                485                 490                 495

Cys Cys Leu Leu Ala Ala Leu Ala Ser Cys Phe Leu Pro Ile Glu Thr
            500                 505                 510

Lys Gly Arg Gly Leu Gln Glu Ser Ser His Arg Glu Trp Gly Gln Glu
        515                 520                 525

Met Val Gly Arg Gly Met His Gly Ala Gly Val Thr Arg Ser Asn Ser
    530                 535                 540

Gly Ser Gln Glu
545

<210> SEQ ID NO 9
<211> LENGTH: 3844
<212> TYPE: DNA
<213> ORGANISM: Rattus norvegicus
<220> FEATURE:
<221> NAME/KEY: CDS
<222> LOCATION: (400)..(2628)
<223> OTHER INFORMATION:

<400> SEQUENCE: 9
cctcagccct gtggctggac cccctccctc acccggggac tccctgaccc ggggaaccaa      60
gctcaggtct ccagagcctc ccagaagaaa ataggcagc cctccctgaa atatcttggc     120
tcctcagttt atcctttcca acctggctcc cccttcccag ttcccctccc tactccctgt     180
ctccctcccc aactcaccct actgaactgg gtgcagagca agccctttt cgccttttc      240 cccatctgga cttctctggc cagttcctct tagtccgatc ccaaagacac tggaacacat     300
ttctaaaggg tcttcttgat ccctccaatt cattgagcaa agggctgaaa agaagcaga     360 gagtaaggta gagccagtga ctcgccccca agccccatc atg gaa gaa ggc ttt        414
                                            Met Glu Glu Gly Phe
                                              1               5 cga gac cga gca gcg ttc atc cgt ggg gcc aaa gac att gcc aag gaa      462
Arg Asp Arg Ala Ala Phe Ile Arg Gly Ala Lys Asp Ile Ala Lys Glu
                10                  15                  20 gtt aag aag cac gcg gcc aag aag gtg gtg aag ggt ctc gac aga gtc      510
Val Lys Lys His Ala Ala Lys Lys Val Val Lys Gly Leu Asp Arg Val
        25                  30                  35 cag gat gaa tat tcc cga agg tcc tac tcc cgc ttt gag gag gag gag      558
Gln Asp Glu Tyr Ser Arg Arg Ser Tyr Ser Arg Phe Glu Glu Glu Glu
    40                  45                  50 gat gat gat gac ttc cct gcc cct gct gac ggc tat tac cgc gga gaa      606
Asp Asp Asp Asp Phe Pro Ala Pro Ala Asp Gly Tyr Tyr Arg Gly Glu
55                  60                  65 ggg gcc cag gat gag gag gaa ggt ggc gct tcc agt gat gcc act gag      654
```

-continued

```
Gly Ala Gln Asp Glu Glu Gly Gly Ala Ser Ser Asp Ala Thr Glu
 70              75              80              85 ggc cac gat gag gat gat gag atc tac gag gga gaa tat cag ggc atc     702
Gly His Asp Glu Asp Asp Glu Ile Tyr Glu Gly Glu Tyr Gln Gly Ile
             90              95             100 ccc cgg gca gag tct ggg ggc aaa ggc gaa cgg atg gca gat ggg gca     750
Pro Arg Ala Glu Ser Gly Gly Lys Gly Glu Arg Met Ala Asp Gly Ala
        105             110             115 ccc ctg gct gga gtg aga ggg ggc tta agt gat ggg gag ggt ccc cct     798
Pro Leu Ala Gly Val Arg Gly Gly Leu Ser Asp Gly Glu Gly Pro Pro
        120             125             130 ggg ggt cgc ggg gag gcg cag cgg cgt aaa gat cgg gaa gaa ttg gct     846
Gly Gly Arg Gly Glu Ala Gln Arg Arg Lys Asp Arg Glu Glu Leu Ala
        135             140             145 cag cag tat gag acc atc ctc cgg gag tgc ggc cat ggt cgc ttc cag     894
Gln Gln Tyr Glu Thr Ile Leu Arg Glu Cys Gly His Gly Arg Phe Gln
150             155             160             165 tgg aca ctc tac ttc gtg ctg ggt ctg gcg ctg atg gcc gat ggt gta     942
Trp Thr Leu Tyr Phe Val Leu Gly Leu Ala Leu Met Ala Asp Gly Val
                170             175             180 gag gtc ttt gtg gtg ggc ttt gtg ctg ccc agt gct gag aaa gat atg     990
Glu Val Phe Val Val Gly Phe Val Leu Pro Ser Ala Glu Lys Asp Met
            185             190             195 tgc ctg tcg gac tcc aac aaa ggc atg cta ggc ctc att gtg tac ctg    1038
Cys Leu Ser Asp Ser Asn Lys Gly Met Leu Gly Leu Ile Val Tyr Leu
        200             205             210 ggc atg atg gtg ggg gcc ttc ctc tgg gga ggc ctg gct gat cgg ctg    1086
Gly Met Met Val Gly Ala Phe Leu Trp Gly Gly Leu Ala Asp Arg Leu
        215             220             225 ggt cgg aga cag tgt ctg ctc atc tcg ctc tca gtc aac agc gtc ttc    1134
Gly Arg Arg Gln Cys Leu Leu Ile Ser Leu Ser Val Asn Ser Val Phe
230             235             240             245 gct ttc ttc tca tcc ttc gtc cag ggt tat ggc acc ttc ctt ttc tgc    1182
Ala Phe Phe Ser Ser Phe Val Gln Gly Tyr Gly Thr Phe Leu Phe Cys
                250             255             260 cgc ctc ctt tct ggg gtt ggg att ggt ggt tcc atc ccc att gtc ttc    1230
Arg Leu Leu Ser Gly Val Gly Ile Gly Gly Ser Ile Pro Ile Val Phe
            265             270             275 tcc tat ttt tcg gag ttt ctg gcc cag gag aaa cgt ggg gag cat ttg    1278
Ser Tyr Phe Ser Glu Phe Leu Ala Gln Glu Lys Arg Gly Glu His Leu
        280             285             290 agc tgg ctc tgt atg ttc tgg atg att ggt ggc gtg tat gca gct gca    1326
Ser Trp Leu Cys Met Phe Trp Met Ile Gly Gly Val Tyr Ala Ala Ala
        295             300             305 atg gcc tgg gcc atc atc ccc cac tat ggg tgg agt ttc cag atg ggc    1374
Met Ala Trp Ala Ile Ile Pro His Tyr Gly Trp Ser Phe Gln Met Gly
310             315             320             325 tct gct tac cag ttc cac agc tgg agg gtc ttt gtc ctc gtc ttt gcc    1422
Ser Ala Tyr Gln Phe His Ser Trp Arg Val Phe Val Leu Val Phe Ala
                330             335             340 ttt ccc tct gtg ttt gcc atc ggg gct ctg act acg cag ccg gag agt    1470
Phe Pro Ser Val Phe Ala Ile Gly Ala Leu Thr Thr Gln Pro Glu Ser
            345             350             355 ccc cgc ttc ttc tta gag aat ggg aag cac gat gag gcc tgg atg gtg    1518
Pro Arg Phe Phe Leu Glu Asn Gly Lys His Asp Glu Ala Trp Met Val
        360             365             370 ctg aag cag gtt cat gac acc aac atg cga gcc aag ggc cat cct gag    1566
Leu Lys Gln Val His Asp Thr Asn Met Arg Ala Lys Gly His Pro Glu
375             380             385
```

```
cga gtc ttc tca gta acc cac att aaa acg att cat cag gag gat gaa    1614
Arg Val Phe Ser Val Thr His Ile Lys Thr Ile His Gln Glu Asp Glu
390                 395                 400                 405 ttg att gag atc cag tca gac aca gga acc tgg tac cag cgc tgg gga    1662
Leu Ile Glu Ile Gln Ser Asp Thr Gly Thr Trp Tyr Gln Arg Trp Gly
            410                 415                 420 gtg cgg gct ttg agc ctg ggg ggt cag gtt tgg ggg aac ttc ctc tcc    1710
Val Arg Ala Leu Ser Leu Gly Gly Gln Val Trp Gly Asn Phe Leu Ser
425                 430                 435 tgc ttc agt cca gag tac cgg cgc atc act ctg atg atg atg ggg gta    1758
Cys Phe Ser Pro Glu Tyr Arg Arg Ile Thr Leu Met Met Met Gly Val
        440                 445                 450 tgg ttc acc atg tcc ttc agc tac tac ggt ttg act gtc tgg ttt ccc    1806
Trp Phe Thr Met Ser Phe Ser Tyr Tyr Gly Leu Thr Val Trp Phe Pro
    455                 460                 465 gac atg atc cgc cat ctc cag gct gtg gac tat gca gcc cga acc aaa    1854
Asp Met Ile Arg His Leu Gln Ala Val Asp Tyr Ala Ala Arg Thr Lys
470                 475                 480                 485 gtg ttc cca ggg gag cgc gtg gag cac gtg aca ttt aac ttc aca ctg    1902
Val Phe Pro Gly Glu Arg Val Glu His Val Thr Phe Asn Phe Thr Leu
            490                 495                 500 gag aat cag atc cac cga ggg gga cag tac ttc aat gac aag ttc atc    1950
Glu Asn Gln Ile His Arg Gly Gly Gln Tyr Phe Asn Asp Lys Phe Ile
505                 510                 515 ggg ctg cgt ctg aag tca gtg tcc ttt gag gat tcc ctg ttt gag gaa    1998
Gly Leu Arg Leu Lys Ser Val Ser Phe Glu Asp Ser Leu Phe Glu Glu
        520                 525                 530 tgt tac ttt gaa gat gtc aca tcc agc aac aca ttc ttc cgc aac tgc    2046
Cys Tyr Phe Glu Asp Val Thr Ser Ser Asn Thr Phe Phe Arg Asn Cys
    535                 540                 545 aca ttc atc aac acc gtg ttc tac aac acg gac ctg ttt gag tac aag    2094
Thr Phe Ile Asn Thr Val Phe Tyr Asn Thr Asp Leu Phe Glu Tyr Lys
550                 555                 560                 565 ttc gtg aac agc cgc ctg gtg aac agc aca ttc ctg cac aat aag gaa    2142
Phe Val Asn Ser Arg Leu Val Asn Ser Thr Phe Leu His Asn Lys Glu
            570                 575                 580 ggt tgc cca cta gat gtg aca ggg acg ggc gaa ggt gcc tac atg gtg    2190
Gly Cys Pro Leu Asp Val Thr Gly Thr Gly Glu Gly Ala Tyr Met Val
585                 590                 595 tac ttt gtc agc ttc ttg ggg aca ctg gct gtg ctc cct gga aat att    2238
Tyr Phe Val Ser Phe Leu Gly Thr Leu Ala Val Leu Pro Gly Asn Ile
        600                 605                 610 gtg tct gct ctg ctc atg gac aag att ggc agg ctc aga atg ctt gct    2286
Val Ser Ala Leu Leu Met Asp Lys Ile Gly Arg Leu Arg Met Leu Ala
615                 620                 625 ggt tcc agt gtg ttg tcc tgt gtt tcc tgc ttc ttc ctg tct ttt ggg    2334
Gly Ser Ser Val Leu Ser Cys Val Ser Cys Phe Phe Leu Ser Phe Gly
630                 635                 640                 645 aac agt gag tca gcc atg atc gct ctg ctc tgc ctt ttt ggg gga gtc    2382
Asn Ser Glu Ser Ala Met Ile Ala Leu Leu Cys Leu Phe Gly Gly Val
            650                 655                 660 agt att gca tcc tgg aac gcg ctg gac gtg ctg act gtt gaa ctc tac    2430
Ser Ile Ala Ser Trp Asn Ala Leu Asp Val Leu Thr Val Glu Leu Tyr
665                 670                 675 cct tcc gac aag agg acg acg gcc ttc ggc ttc ctg aat gcc ctg tgt    2478
Pro Ser Asp Lys Arg Thr Thr Ala Phe Gly Phe Leu Asn Ala Leu Cys
        680                 685                 690 aag ctg gca gct gta ctg ggc atc agc atc ttc acg tcc ttt gtg gga    2526
Lys Leu Ala Ala Val Leu Gly Ile Ser Ile Phe Thr Ser Phe Val Gly
695                 700                 705
```

-continued

| | | |
|---|---|---|
| atc acc aag gcc gct ccc atc ctc ttc gcc tca gct gcg ctt gcc ctt<br>Ile Thr Lys Ala Ala Pro Ile Leu Phe Ala Ser Ala Ala Leu Ala Leu<br>710                        715                    720                  725 | 2574 |
| ggt agc tct ctg gct ctg aag ctg cct gag acc cgg gga cag gtg ctg<br>Gly Ser Ser Leu Ala Leu Lys Leu Pro Glu Thr Arg Gly Gln Val Leu<br>               730                    735                    740 | 2622 |
| cag tga gggatggggg agtgtctcag gggctttagg gatggcaggc acactgtgac<br>Gln | 2678 |
| caataatttc ttttatccct accctgccct gctgtcctgg tcctactccg tgtttggtgt | 2738 |
| cttagctgtg tgcctgtgtg catgtgtgtg accctgacgg gcaggggcta cggggagggt | 2798 |
| cccctttgtcc catgtttggg aggagggact ccccacctgc tgccaccctc aactttgcac | 2858 |
| aaggagaagg ctgagctgca tccttctctc cctcagtgtt agcaggggtg gggacgactg | 2918 |
| tttctctgct ccaggtgttc cagaatttct gcctttccca tcattccctc cgcctaggcc | 2978 |
| ctggtgaacc acaggtatgg agttatagtg ggggctgagg cttggaccaa agaacttct | 3038 |
| tgagtgggag cctcccaagg atgctgggga gtagcaataa accttagcct ccgttttcac | 3098 |
| ctcaattcag gctacaagtg tgaagcctgg attttatgga attagttttc tgattcttat | 3158 |
| ttatatgtaa gttctgaggc agcttagctg gactgtgtgt ggatgtatac atacactcat | 3218 |
| atgtgtgtgt gtgtgcgccg cgtgcgtgtg cgtgtgtgta tgtgtgccat ggggtagggg | 3278 |
| taccactata ctgttcaatt ataagccaag agtagtagtt tcagtgagca cacacacaac | 3338 |
| actgttttc tatcgtaact cccagaatct tgtacctgtg ttggggctgc aggcagaagt | 3398 |
| ccttggtcag gctggggtga gccctgcaat cttgggggac ctgagggcac ctgacaagga | 3458 |
| ctttctcctt cctctagaga ggttctaccc actagccaca gccctcccat ctgacctgtc | 3518 |
| cacacaggca gtgtatcaga ggaaagaaag ggaaaataac caggcacaca tggtcaaacc | 3578 |
| agcaggtctg aaagcacaag aagctggggc aggggcagga agcaggggtc catcccctaa | 3638 |
| cccttctcaa aaaggctggg tcgtgaggga cccctaatgc agggacctga agcctcagtt | 3698 |
| tccccatctt gccctccac agaacagcct ctgtaggtag agctgccccc cgtcctaccc | 3758 |
| tactcttgtg gctgctttct tggtactct tcccactccc accgtagctg tgacgtgttg | 3818 |
| tagttttag ctgtttgtaa aatgtt | 3844 |

<210> SEQ ID NO 10
<211> LENGTH: 742
<212> TYPE: PRT
<213> ORGANISM: Rattus norvegicus

<400> SEQUENCE: 10

Met Glu Glu Gly Phe Arg Asp Arg Ala Ala Phe Ile Arg Gly Ala Lys
1                   5                    10                  15

Asp Ile Ala Lys Glu Val Lys Lys His Ala Ala Lys Lys Val Val Lys
                 20                    25                  30

Gly Leu Asp Arg Val Gln Asp Glu Tyr Ser Arg Arg Ser Tyr Ser Arg
        35                    40                  45

Phe Glu Glu Glu Glu Asp Asp Asp Phe Pro Ala Pro Ala Asp Gly
    50                    55                  60

Tyr Tyr Arg Gly Glu Gly Ala Gln Asp Glu Glu Gly Gly Ala Ser
65                   70                    75                  80

Ser Asp Ala Thr Glu Gly His Asp Glu Asp Asp Glu Ile Tyr Glu Gly
                 85                    90                  95

Glu Tyr Gln Gly Ile Pro Arg Ala Glu Ser Gly Gly Lys Gly Glu Arg

```
                    100                 105                 110
Met Ala Asp Gly Ala Pro Leu Ala Gly Val Arg Gly Gly Leu Ser Asp
                115                 120                 125

Gly Glu Gly Pro Pro Gly Gly Arg Gly Glu Ala Gln Arg Arg Lys Asp
            130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Gly Leu Ala Leu
                165                 170                 175

Met Ala Asp Gly Val Glu Val Phe Val Val Gly Phe Val Leu Pro Ser
                180                 185                 190

Ala Glu Lys Asp Met Cys Leu Ser Asp Ser Asn Lys Gly Met Leu Gly
            195                 200                 205

Leu Ile Val Tyr Leu Gly Met Met Val Gly Ala Phe Leu Trp Gly Gly
            210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
            275                 280                 285

Arg Gly Glu His Leu Ser Trp Leu Cys Met Phe Trp Met Ile Gly Gly
290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Phe Ala Phe Pro Ser Val Phe Ala Ile Gly Ala Leu Thr
                340                 345                 350

Thr Gln Pro Glu Ser Pro Arg Phe Phe Leu Glu Asn Gly Lys His Asp
            355                 360                 365

Glu Ala Trp Met Val Leu Lys Gln Val His Asp Thr Asn Met Arg Ala
370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Ser Pro Glu Tyr Arg Arg Ile Thr Leu
            435                 440                 445

Met Met Met Gly Val Trp Phe Thr Met Ser Phe Ser Tyr Tyr Gly Leu
            450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
                500                 505                 510

Asn Asp Lys Phe Ile Gly Leu Arg Leu Lys Ser Val Ser Phe Glu Asp
            515                 520                 525
```

```
Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Leu Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 11
<211> LENGTH: 2052
<212> TYPE: DNA
<213> ORGANISM: Rattus norvegicus
<220> FEATURE:
<221> NAME/KEY: CDS
<222> LOCATION: (1)..(2052)
<223> OTHER INFORMATION:

<400> SEQUENCE: 11 atg gat gac tac agg tat cgg gac aac tat gag ggc tat gcc cct aat      48
Met Asp Asp Tyr Arg Tyr Arg Asp Asn Tyr Glu Gly Tyr Ala Pro Asn
1               5                   10                  15 gat ggc tac tac cgg ggc aat gag cag aac ccg gaa gaa gat gca cag      96
Asp Gly Tyr Tyr Arg Gly Asn Glu Gln Asn Pro Glu Glu Asp Ala Gln
            20                  25                  30 agc gat gtt aca gaa ggc cac gat gaa gag gat gag atc tat gag ggc     144
Ser Asp Val Thr Glu Gly His Asp Glu Glu Asp Glu Ile Tyr Glu Gly
        35                  40                  45 gag tac caa ggc atc cct cat cca gat gat gtc aag tct aag cag act     192
Glu Tyr Gln Gly Ile Pro His Pro Asp Asp Val Lys Ser Lys Gln Thr
    50                  55                  60 aag atg gca ccg tcc aga gca gat ggc ctt cgg ggc cag gca gac ctg     240
Lys Met Ala Pro Ser Arg Ala Asp Gly Leu Arg Gly Gln Ala Asp Leu
65                  70                  75                  80 atg gct gag aga atg gaa gat gag gag cag ctc gct cac cag tac gag     288
Met Ala Glu Arg Met Glu Asp Glu Glu Gln Leu Ala His Gln Tyr Glu
                85                  90                  95
```

-continued

```
acc atc att gat gag tgt ggc cat ggg cgc ttc cag tgg acc ctc ttt      336
Thr Ile Ile Asp Glu Cys Gly His Gly Arg Phe Gln Trp Thr Leu Phe
            100                 105                 110 ttc gtc ttg gtc ttg gcc ttg atg gct gac gga gtg gaa gtg ttt gtg      384
Phe Val Leu Val Leu Ala Leu Met Ala Asp Gly Val Glu Val Phe Val
        115                 120                 125 gtg agc ttt gct ctg cca agt gca gag aaa gat atg tgt ctg tca agt      432
Val Ser Phe Ala Leu Pro Ser Ala Glu Lys Asp Met Cys Leu Ser Ser
    130                 135                 140 tcc aag aaa gga atg ctc ggg ctg att gtc tac cta gga atg atg gca      480
Ser Lys Lys Gly Met Leu Gly Leu Ile Val Tyr Leu Gly Met Met Ala
145                 150                 155                 160 gga gcc ttc atc ctg ggg ggc ctg gct gat aaa ctg gga agg aag aag      528
Gly Ala Phe Ile Leu Gly Gly Leu Ala Asp Lys Leu Gly Arg Lys Lys
                165                 170                 175 gtc ctc agc atg tcc ttg gct atc aat gct tcc ttt gcc tcc ctc tcc      576
Val Leu Ser Met Ser Leu Ala Ile Asn Ala Ser Phe Ala Ser Leu Ser
            180                 185                 190 tcc ttc gtg cag gga tat gga gct ttc ctc ttc tgc aga ctc atc tca      624
Ser Phe Val Gln Gly Tyr Gly Ala Phe Leu Phe Cys Arg Leu Ile Ser
        195                 200                 205 ggc ata ggt att ggg ggc tcc ctg cca att gtt ttt gcc tac ttt tct      672
Gly Ile Gly Ile Gly Gly Ser Leu Pro Ile Val Phe Ala Tyr Phe Ser
    210                 215                 220 gag ttc tta tca cgg gag aaa cgc ggt gag cat ctc agc tgg ctg ggt      720
Glu Phe Leu Ser Arg Glu Lys Arg Gly Glu His Leu Ser Trp Leu Gly
225                 230                 235                 240 atc ttc tgg atg act ggg ggc atc tac gca tct gcc atg gcc tgg agc      768
Ile Phe Trp Met Thr Gly Gly Ile Tyr Ala Ser Ala Met Ala Trp Ser
                245                 250                 255 atc att cca cac tat ggc tgg ggc ttc agc atg gga acc aat tat cac      816
Ile Ile Pro His Tyr Gly Trp Gly Phe Ser Met Gly Thr Asn Tyr His
            260                 265                 270 ttc cac agc tgg aga gtg ttt gtc atc gtc tgt gct ctg cct gcc act      864
Phe His Ser Trp Arg Val Phe Val Ile Val Cys Ala Leu Pro Ala Thr
        275                 280                 285 gtg tcc atg gtg gcc ctg aag ttc atg cca gaa agc ccc agg ttc ctg      912
Val Ser Met Val Ala Leu Lys Phe Met Pro Glu Ser Pro Arg Phe Leu
    290                 295                 300 ctg gag atg ggc aag cat gat gaa gcc tgg atg att ctc aag caa gtc      960
Leu Glu Met Gly Lys His Asp Glu Ala Trp Met Ile Leu Lys Gln Val
305                 310                 315                 320 cat gac acc aac atg aga gct aag ggg acc cct gag aag gtg ttc acg     1008
His Asp Thr Asn Met Arg Ala Lys Gly Thr Pro Glu Lys Val Phe Thr
                325                 330                 335 gtt tcc cac atc aaa act ccc aag caa atg gat gaa ttc att gag atc     1056
Val Ser His Ile Lys Thr Pro Lys Gln Met Asp Glu Phe Ile Glu Ile
            340                 345                 350 cag agt tca aca ggg act tgg tac cag cgc tgg ttg gtc agg ttc atg     1104
Gln Ser Ser Thr Gly Thr Trp Tyr Gln Arg Trp Leu Val Arg Phe Met
        355                 360                 365 acc att ttc aaa cag gtg tgg gat aac gcc ttg tac tgt gtg atg gga     1152
Thr Ile Phe Lys Gln Val Trp Asp Asn Ala Leu Tyr Cys Val Met Gly
    370                 375                 380 ccc tac aga atg aac acc ctg att ctg gct gtg gtc tgg ttc acc atg     1200
Pro Tyr Arg Met Asn Thr Leu Ile Leu Ala Val Val Trp Phe Thr Met
385                 390                 395                 400 gcc tta agt tac tat ggc ctg aca gtg tgg ttc ccc gac atg atc cgg     1248
Ala Leu Ser Tyr Tyr Gly Leu Thr Val Trp Phe Pro Asp Met Ile Arg
                405                 410                 415
```

```
tat ttc cag gat gaa gaa tat aag tct aaa atg aag gtg ttt ttt ggt    1296
Tyr Phe Gln Asp Glu Glu Tyr Lys Ser Lys Met Lys Val Phe Phe Gly
            420                 425                 430 gag cac gtg cat ggc gcc aca atc aac ttc acc atg gaa aac cag atc    1344
Glu His Val His Gly Ala Thr Ile Asn Phe Thr Met Glu Asn Gln Ile
        435                 440                 445 cac caa cat ggg aag ctt gtg aac gat aag ttc ata aag atg tac ttt    1392
His Gln His Gly Lys Leu Val Asn Asp Lys Phe Ile Lys Met Tyr Phe
    450                 455                 460 aag cat gtc ctc ttt gag gac aca ttc ttt gac aaa tgc tat ttt gaa    1440
Lys His Val Leu Phe Glu Asp Thr Phe Phe Asp Lys Cys Tyr Phe Glu
465                 470                 475                 480 gat gtg aca tcc aca gat act tat ttc aag aac tgc acc att gaa tcg    1488
Asp Val Thr Ser Thr Asp Thr Tyr Phe Lys Asn Cys Thr Ile Glu Ser
                485                 490                 495 act acc ttc tac aac aca gac ctc tac aaa cac aag ttc att gac tgt    1536
Thr Thr Phe Tyr Asn Thr Asp Leu Tyr Lys His Lys Phe Ile Asp Cys
            500                 505                 510 cgg ttt atc aat tcc acc ttt ctg gag cag aag gag ggc tgc cac atg    1584
Arg Phe Ile Asn Ser Thr Phe Leu Glu Gln Lys Glu Gly Cys His Met
        515                 520                 525 gac ttt gaa gag gac aat gat ttt ctg att tac ctc gtc agc ttc ctc    1632
Asp Phe Glu Glu Asp Asn Asp Phe Leu Ile Tyr Leu Val Ser Phe Leu
    530                 535                 540 ggc agc ctg tct gtc ttg cct ggg aac ata att tct gcc ctg ctc atg    1680
Gly Ser Leu Ser Val Leu Pro Gly Asn Ile Ile Ser Ala Leu Leu Met
545                 550                 555                 560 gac aga atc gga aga ctt aag atg att ggt ggc tcc atg ctc atc tct    1728
Asp Arg Ile Gly Arg Leu Lys Met Ile Gly Gly Ser Met Leu Ile Ser
                565                 570                 575 gca gtc tgc tgc ttc ttc ctg ttt ttt ggc aac agc gag tct gcg atg    1776
Ala Val Cys Cys Phe Phe Leu Phe Phe Gly Asn Ser Glu Ser Ala Met
            580                 585                 590 atc ggc tgg caa tgc ctg ttc tgt ggg acc agc att gca gcc tgg aat    1824
Ile Gly Trp Gln Cys Leu Phe Cys Gly Thr Ser Ile Ala Ala Trp Asn
        595                 600                 605 gct ctg gat gtg atc aca gta gag ctg tat ccc acc aac cag agg gcc    1872
Ala Leu Asp Val Ile Thr Val Glu Leu Tyr Pro Thr Asn Gln Arg Ala
    610                 615                 620 act gcc ttc ggc atc ctc aat gga ctg tgc aaa ctt ggt gcc atc ctg    1920
Thr Ala Phe Gly Ile Leu Asn Gly Leu Cys Lys Leu Gly Ala Ile Leu
625                 630                 635                 640 gga aac act atc ttt gct tct ttt gtt ggg atc acc aaa gtg gtc ccc    1968
Gly Asn Thr Ile Phe Ala Ser Phe Val Gly Ile Thr Lys Val Val Pro
                645                 650                 655 atc ctt ctg gct gct gct tct ctg gtt gga ggt ggc ttg gtt gcc ctt    2016
Ile Leu Leu Ala Ala Ala Ser Leu Val Gly Gly Gly Leu Val Ala Leu
            660                 665                 670 cga ctg cca gag act cga gag cag gtc ctg atg tga                    2052
Arg Leu Pro Glu Thr Arg Glu Gln Val Leu Met
        675                 680
```

<210> SEQ ID NO 12
<211> LENGTH: 683
<212> TYPE: PRT
<213> ORGANISM: Rattus norvegicus

<400> SEQUENCE: 12

```
Met Asp Asp Tyr Arg Tyr Arg Asp Asn Tyr Glu Gly Tyr Ala Pro Asn
1               5                   10                  15
```

```
Asp Gly Tyr Tyr Arg Gly Asn Glu Gln Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ser Lys Gln Thr
    50                  55                  60

Lys Met Ala Pro Ser Arg Ala Asp Gly Leu Arg Gly Gln Ala Asp Leu
65                  70                  75                  80

Met Ala Glu Arg Met Glu Asp Glu Glu Gln Leu Ala His Gln Tyr Glu
                85                  90                  95

Thr Ile Ile Asp Glu Cys Gly His Gly Arg Phe Gln Trp Thr Leu Phe
            100                 105                 110

Phe Val Leu Val Leu Ala Leu Met Ala Asp Gly Val Glu Val Phe Val
        115                 120                 125

Val Ser Phe Ala Leu Pro Ser Ala Glu Lys Asp Met Cys Leu Ser Ser
    130                 135                 140

Ser Lys Lys Gly Met Leu Gly Leu Ile Val Tyr Leu Gly Met Met Ala
145                 150                 155                 160

Gly Ala Phe Ile Leu Gly Gly Leu Ala Asp Lys Leu Gly Arg Lys Lys
                165                 170                 175

Val Leu Ser Met Ser Leu Ala Ile Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ser Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Ile Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Ala Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser His Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Met
        355                 360                 365

Thr Ile Phe Lys Gln Val Trp Asp Asn Ala Leu Tyr Cys Val Met Gly
    370                 375                 380

Pro Tyr Arg Met Asn Thr Leu Ile Leu Ala Val Val Trp Phe Thr Met
385                 390                 395                 400

Ala Leu Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430
```

```
Glu His Val His Gly Ala Thr Ile Asn Phe Thr Met Glu Asn Gln Ile
        435                 440                 445

His Gln His Gly Lys Leu Val Asn Asp Lys Phe Ile Lys Met Tyr Phe
    450                 455                 460

Lys His Val Leu Phe Glu Asp Thr Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asp Cys
            500                 505                 510

Arg Phe Ile Asn Ser Thr Phe Leu Glu Gln Lys Glu Gly Cys His Met
        515                 520                 525

Asp Phe Glu Glu Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Leu Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Val Ala Leu
            660                 665                 670

Arg Leu Pro Glu Thr Arg Glu Gln Val Leu Met
        675                 680

<210> SEQ ID NO 13
<211> LENGTH: 2622
<212> TYPE: DNA
<213> ORGANISM: Rattus norvegicus
<220> FEATURE:
<221> NAME/KEY: CDS
<222> LOCATION: (224)..(2407)
<223> OTHER INFORMATION:

<400> SEQUENCE: 13
gcgcgctgca ggaagagtgg cagaccgaag cggcctcggg ctgcaaacgg agggggcgctc     60 gcgcggcgac ggctgcaggg ctgacaccgc tcagggcagg ggggtcccag gcggctggaa    120
cgctctattc tgaactgtga gtggatgatg ctgttgcagc caagctgctg aacacactcc    180
gtggactctt ccctgctgtg ccttgcccat cggccgagat aaa atg gaa gac tcc     235
                                              Met Glu Asp Ser
                                                1 tac aag gat agg act tca ctg atg aag ggc gcc aag gac att gcc aaa     283
Tyr Lys Asp Arg Thr Ser Leu Met Lys Gly Ala Lys Asp Ile Ala Lys
 5                  10                  15                  20 gag gtg aag aag caa aca gtg aag aag gtg aac cag gca gtg gac cgg     331
Glu Val Lys Lys Gln Thr Val Lys Lys Val Asn Gln Ala Val Asp Arg
                 25                  30                  35 gcc cag gat gaa tac acc cag cgg tcc tac agt cga ttc cag gat gaa     379
Ala Gln Asp Glu Tyr Thr Gln Arg Ser Tyr Ser Arg Phe Gln Asp Glu
```

```
                  Ala Gln Asp Glu Tyr Thr Gln Arg Ser Tyr Ser Arg Phe Gln Asp Glu
                               40                  45                  50 gat gat gat gat gac tac tac cca cct gga gaa acc tac agt ggg gag           427
Asp Asp Asp Asp Asp Tyr Tyr Pro Pro Gly Glu Thr Tyr Ser Gly Glu
             55                  60                  65 gcc aat gat gat gaa ggc tca agt gaa gcc act gag ggt cac gat gaa           475
Ala Asn Asp Asp Glu Gly Ser Ser Glu Ala Thr Glu Gly His Asp Glu
 70                  75                  80 gaa gac gag atc tat gaa ggg gaa tac cag ggc atc ccc agc acg aac           523
Glu Asp Glu Ile Tyr Glu Gly Glu Tyr Gln Gly Ile Pro Ser Thr Asn
 85                  90                  95                 100 caa ggg aag gac agc ata gtg tct gta gga caa ccc aaa gga gat gag           571
Gln Gly Lys Asp Ser Ile Val Ser Val Gly Gln Pro Lys Gly Asp Glu
                 105                 110                 115 tac aag gac cgc aga gag ctg gag tca gag agg agg gct gat gag gag           619
Tyr Lys Asp Arg Arg Glu Leu Glu Ser Glu Arg Arg Ala Asp Glu Glu
                 120                 125                 130 gag ctc gcc cag cag tat gag ctg ata atc caa gag tgt ggc cat ggc           667
Glu Leu Ala Gln Gln Tyr Glu Leu Ile Ile Gln Glu Cys Gly His Gly
                 135                 140                 145 cgt ttc cag tgg gcc ctt ttc ttc gtc ctg ggc atg gct ctc atg gca           715
Arg Phe Gln Trp Ala Leu Phe Phe Val Leu Gly Met Ala Leu Met Ala
         150                 155                 160 gac ggc gtg gag gtg ttt gtg gtg ggc ttt gtg tta ccc agt gca gag           763
Asp Gly Val Glu Val Phe Val Val Gly Phe Val Leu Pro Ser Ala Glu
165                 170                 175                 180 aca gac cta tgc ata ccg aat tca gga tct gga tgg cta ggc agc ata           811
Thr Asp Leu Cys Ile Pro Asn Ser Gly Ser Gly Trp Leu Gly Ser Ile
                 185                 190                 195 gtg tac ctc ggg atg atg gtg ggg gcg ttc ttc tgg gga gga ctg gca           859
Val Tyr Leu Gly Met Met Val Gly Ala Phe Phe Trp Gly Gly Leu Ala
                 200                 205                 210 gac aaa gtg gga agg aag cag tct ctt ctg att tgc atg tcc gtc aac           907
Asp Lys Val Gly Arg Lys Gln Ser Leu Leu Ile Cys Met Ser Val Asn
                 215                 220                 225 gga ttc ttt gcc ttc ctt tct tca ttt gtc caa ggt tac ggc ttc ttt           955
Gly Phe Phe Ala Phe Leu Ser Ser Phe Val Gln Gly Tyr Gly Phe Phe
         230                 235                 240 ctc ctc tgt cgt ttg ctt tca gga ttc ggg att gga ggc gcc att ccc          1003
Leu Leu Cys Arg Leu Leu Ser Gly Phe Gly Ile Gly Gly Ala Ile Pro
245                 250                 255                 260 act gtg ttc tcc tac ttt gct gaa gtc ctg gcc cgg gag aag cgc ggt          1051
Thr Val Phe Ser Tyr Phe Ala Glu Val Leu Ala Arg Glu Lys Arg Gly
                 265                 270                 275 gag cac ctc agt tgg ctc tgc atg ttc tgg atg att ggc ggt atc tat          1099
Glu His Leu Ser Trp Leu Cys Met Phe Trp Met Ile Gly Gly Ile Tyr
                 280                 285                 290 gct tca gcc atg gcc tgg gcc atc atc ccc cac tat ggg tgg agc ttc          1147
Ala Ser Ala Met Ala Trp Ala Ile Ile Pro His Tyr Gly Trp Ser Phe
         295                 300                 305 agc atg ggc tca gcc tac cag ttc cac agc tgg cgc gtc ttc gtc atc          1195
Ser Met Gly Ser Ala Tyr Gln Phe His Ser Trp Arg Val Phe Val Ile
310                 315                 320 gtc tgt gcc ctc ccg tgc gtc tcc tcg gtg gtg gcc ctc acc ttc atg          1243
Val Cys Ala Leu Pro Cys Val Ser Ser Val Val Ala Leu Thr Phe Met
325                 330                 335                 340 ccc gaa agc cct cgg ttc ttg ctg gag gta gga aaa cat gat gaa gcc          1291
Pro Glu Ser Pro Arg Phe Leu Leu Glu Val Gly Lys His Asp Glu Ala
                 345                 350                 355
```

-continued

```
tgg atg att ctg aag cta att cat gat acc aac atg aga gcc cgg ggc      1339
Trp Met Ile Leu Lys Leu Ile His Asp Thr Asn Met Arg Ala Arg Gly
        360                 365                 370 cag cca gag aag gtc ttc acg gta aat aaa atc aag act ccc aag caa      1387
Gln Pro Glu Lys Val Phe Thr Val Asn Lys Ile Lys Thr Pro Lys Gln
    375                 380                 385 ata gat gag ctg att gag att gag agc gac aca gga acc tgg tac cgg      1435
Ile Asp Glu Leu Ile Glu Ile Glu Ser Asp Thr Gly Thr Trp Tyr Arg
390                 395                 400 agg tgt ttt gtt cgg atc cgc aca gaa ctg tac gga att tgg ttg act      1483
Arg Cys Phe Val Arg Ile Arg Thr Glu Leu Tyr Gly Ile Trp Leu Thr
405                 410                 415                 420 ttt atg aga tgc ttc aac tac ccg gtc agg gaa aac acc ata aag ctt      1531
Phe Met Arg Cys Phe Asn Tyr Pro Val Arg Glu Asn Thr Ile Lys Leu
                425                 430                 435 acg att gtt tgg ttc acc ctg tcc ttt ggg tac tat gga ctg tcc gtt      1579
Thr Ile Val Trp Phe Thr Leu Ser Phe Gly Tyr Tyr Gly Leu Ser Val
            440                 445                 450 tgg ttc cca gat gtc att aaa cac ctc cag tct gac gag tac gcc ctg      1627
Trp Phe Pro Asp Val Ile Lys His Leu Gln Ser Asp Glu Tyr Ala Leu
        455                 460                 465 ctg act cgg aat gtg cag aag gat aaa tat gca aac ttt agc att aac      1675
Leu Thr Arg Asn Val Gln Lys Asp Lys Tyr Ala Asn Phe Ser Ile Asn
    470                 475                 480 ttc acc atg gaa aac cag gtc cac acc gga atg gaa tat gac aat ggc      1723
Phe Thr Met Glu Asn Gln Val His Thr Gly Met Glu Tyr Asp Asn Gly
485                 490                 495                 500 agg ttc ctc gga gtc aaa ttc aaa tcg gta acc ttc aag gat tca gtg      1771
Arg Phe Leu Gly Val Lys Phe Lys Ser Val Thr Phe Lys Asp Ser Val
                505                 510                 515 ttt aag tcc tgc acc ttt gac gat gtg acc tca gtc aac acc tac ttc      1819
Phe Lys Ser Cys Thr Phe Asp Asp Val Thr Ser Val Asn Thr Tyr Phe
            520                 525                 530 aag aac tgc acg ttt att gat acc ctt ttt gag aac aca gat ttt gag      1867
Lys Asn Cys Thr Phe Ile Asp Thr Leu Phe Glu Asn Thr Asp Phe Glu
        535                 540                 545 ccc tat aaa ttc ata gac agc gag ttt caa aac tgc tcg ttt ctt cac      1915
Pro Tyr Lys Phe Ile Asp Ser Glu Phe Gln Asn Cys Ser Phe Leu His
    550                 555                 560 aat aag acg gga tgt cag att act ttt gac gac gac tac agt gcc tac      1963
Asn Lys Thr Gly Cys Gln Ile Thr Phe Asp Asp Asp Tyr Ser Ala Tyr
565                 570                 575                 580 tgg att tac ttt gtc aac ttt ctc ggg aca ttg gca gtg tta cca gga      2011
Trp Ile Tyr Phe Val Asn Phe Leu Gly Thr Leu Ala Val Leu Pro Gly
                585                 590                 595 aat atc gtg tct gct ctc ctg atg gac agg atc ggg cgc tta acg atg      2059
Asn Ile Val Ser Ala Leu Leu Met Asp Arg Ile Gly Arg Leu Thr Met
            600                 605                 610 cta ggt ggc tcc atg gtg ctc tcg ggg atc agc tgc ttc ttc ctg tgg      2107
Leu Gly Gly Ser Met Val Leu Ser Gly Ile Ser Cys Phe Phe Leu Trp
        615                 620                 625 ttt ggc acc agc gaa tcc atg atg ata ggc atg ctg tgc ttg tac aac      2155
Phe Gly Thr Ser Glu Ser Met Met Ile Gly Met Leu Cys Leu Tyr Asn
    630                 635                 640 gga ctg acc atc tca gcg tgg aac tct ctt gat gta gtc acg gtg gaa      2203
Gly Leu Thr Ile Ser Ala Trp Asn Ser Leu Asp Val Val Thr Val Glu
645                 650                 655                 660 cta tac ccc aca gac cgg aga gca acg ggc ttt ggc ttc ttg aac gca      2251
Leu Tyr Pro Thr Asp Arg Arg Ala Thr Gly Phe Gly Phe Leu Asn Ala
                665                 670                 675
```

```
ctc tgt aaa gca gcg gcc gtc ctg gga aac tta ata ttc ggc tcc ttg      2299
Leu Cys Lys Ala Ala Ala Val Leu Gly Asn Leu Ile Phe Gly Ser Leu
            680                 685                 690 gtc agc atc acc aaa gca atc cct atc ctg ctg gct tcc acc gtg ctc      2347
Val Ser Ile Thr Lys Ala Ile Pro Ile Leu Leu Ala Ser Thr Val Leu
        695                 700                 705 gtg tgt gga gga ctc gtg ggg ctg cgc ctg ccc gac aca aga acc cag      2395
Val Cys Gly Gly Leu Val Gly Leu Arg Leu Pro Asp Thr Arg Thr Gln
    710                 715                 720 gtt ctg atg tga caaaagccat tctcttctct caccatgggt cagccctatt         2447
Val Leu Met
725 gcctgactca aggcttcaga gttttatgt atagaaaggt ggccaagtat cagaactcaa     2507 acttttgctg tgacgtaaat gtagctgtgt attgtccccg ccagtgtgat ttgcagggtc    2567 ctccccctcc cccgcgcctt gttatctttt cctaattgtg atgttcctgc ttccg         2622

<210> SEQ ID NO 14
<211> LENGTH: 727
<212> TYPE: PRT
<213> ORGANISM: Rattus norvegicus

<400> SEQUENCE: 14

Met Glu Asp Ser Tyr Lys Asp Arg Thr Ser Leu Met Lys Gly Ala Lys
1               5                   10                  15

Asp Ile Ala Lys Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Asp Asp Asp Asp Tyr Tyr Pro Pro Gly Glu Thr
    50                  55                  60

Tyr Ser Gly Glu Ala Asn Asp Asp Glu Gly Ser Ser Glu Ala Thr Glu
65                  70                  75                  80

Gly His Asp Glu Glu Asp Glu Ile Tyr Glu Gly Glu Tyr Gln Gly Ile
                85                  90                  95

Pro Ser Thr Asn Gln Gly Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Glu Leu Ala Gln Gln Tyr Glu Leu Ile Ile Gln Glu
    130                 135                 140

Cys Gly His Gly Arg Phe Gln Trp Ala Leu Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Ser Gly Trp
            180                 185                 190

Leu Gly Ser Ile Val Tyr Leu Gly Met Met Val Gly Ala Phe Phe Trp
        195                 200                 205

Gly Gly Leu Ala Asp Lys Val Gly Arg Lys Gln Ser Leu Leu Ile Cys
    210                 215                 220

Met Ser Val Asn Gly Phe Ala Phe Leu Ser Ser Phe Val Gln Gly
225                 230                 235                 240

Tyr Gly Phe Phe Leu Leu Cys Arg Leu Leu Ser Gly Phe Gly Ile Gly
                245                 250                 255
```

-continued

```
Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285

Gly Gly Ile Tyr Ala Ser Ala Met Ala Trp Ala Ile Ile Pro His Tyr
        290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
            355                 360                 365

Arg Ala Arg Gly Gln Pro Glu Lys Val Phe Thr Val Asn Lys Ile Lys
        370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Glu Asn
            420                 425                 430

Thr Ile Lys Leu Thr Ile Val Trp Phe Thr Leu Ser Phe Gly Tyr Tyr
        435                 440                 445

Gly Leu Ser Val Trp Phe Pro Asp Val Ile Lys His Leu Gln Ser Asp
        450                 455                 460

Glu Tyr Ala Leu Leu Thr Arg Asn Val Gln Lys Asp Lys Tyr Ala Asn
465                 470                 475                 480

Phe Ser Ile Asn Phe Thr Met Glu Asn Gln Val His Thr Gly Met Glu
                485                 490                 495

Tyr Asp Asn Gly Arg Phe Leu Gly Val Lys Phe Lys Ser Val Thr Phe
                500                 505                 510

Lys Asp Ser Val Phe Lys Ser Cys Thr Phe Asp Val Thr Ser Val
            515                 520                 525

Asn Thr Tyr Phe Lys Asn Cys Thr Phe Ile Asp Thr Leu Phe Glu Asn
        530                 535                 540

Thr Asp Phe Glu Pro Tyr Lys Phe Ile Asp Ser Glu Phe Gln Asn Cys
545                 550                 555                 560

Ser Phe Leu His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
        610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
                660                 665                 670

Phe Leu Asn Ala Leu Cys Lys Ala Ala Ala Val Leu Gly Asn Leu Ile
```

```
                675                 680                 685
Phe Gly Ser Leu Val Ser Ile Thr Lys Ala Ile Pro Ile Leu Leu Ala
        690                 695                 700

Ser Thr Val Leu Val Cys Gly Leu Val Gly Leu Arg Leu Pro Asp
705                 710                 715                 720

Thr Arg Thr Gln Val Leu Met
                725

<210> SEQ ID NO 15
<211> LENGTH: 1647
<212> TYPE: DNA
<213> ORGANISM: Rattus norvegicus
<220> FEATURE:
<221> NAME/KEY: CDS
<222> LOCATION: (1)..(1647)
<223> OTHER INFORMATION:

<400> SEQUENCE: 15 atg gag gag gac ctg ttc cag ctc agg cag ttg ccg gtg gtg aaa ttc        48
Met Glu Glu Asp Leu Phe Gln Leu Arg Gln Leu Pro Val Val Lys Phe
1               5                   10                  15 cgc cgc aca gga gag agc gca cgg tca gag gac gac gcg gct tcc ggg        96
Arg Arg Thr Gly Glu Ser Ala Arg Ser Glu Asp Asp Ala Ala Ser Gly
            20                  25                  30 gaa cat gat gtt cag att gag ggg gtc cga gtg ggc cta gaa gct gtc       144
Glu His Asp Val Gln Ile Glu Gly Val Arg Val Gly Leu Glu Ala Val
        35                  40                  45 gag ctg gat gat gga gca gct gtc ccc aag gag ttt gcc aat ccc act       192
Glu Leu Asp Asp Gly Ala Ala Val Pro Lys Glu Phe Ala Asn Pro Thr
    50                  55                  60 gat gac act ttc atg gtc gaa gat gcg gtg gaa gcc att ggg ttc gga       240
Asp Asp Thr Phe Met Val Glu Asp Ala Val Glu Ala Ile Gly Phe Gly
65                  70                  75                  80 aga ttc cag tgg aag ctc tct gtt ctc acc ggc ttg gct tgg atg gcg       288
Arg Phe Gln Trp Lys Leu Ser Val Leu Thr Gly Leu Ala Trp Met Ala
                85                  90                  95 gac gcc atg gag atg atg att ctg agc atc ctg gcg cct cag ctg cac       336
Asp Ala Met Glu Met Met Ile Leu Ser Ile Leu Ala Pro Gln Leu His
            100                 105                 110 tgc gag tgg cga ctc ccc agc tgg cag gtg gcg ctg ctg act tcg gtg       384
Cys Glu Trp Arg Leu Pro Ser Trp Gln Val Ala Leu Leu Thr Ser Val
        115                 120                 125 gtc ttc att ggt atg atg tcc agt tct acg ctc tgg gga aac atc tcg       432
Val Phe Ile Gly Met Met Ser Ser Ser Thr Leu Trp Gly Asn Ile Ser
    130                 135                 140 gat cag tat ggc agg aaa aca ggg ctg aag atc agt gtg ttc tgg acc       480
Asp Gln Tyr Gly Arg Lys Thr Gly Leu Lys Ile Ser Val Phe Trp Thr
145                 150                 155                 160 ctg tac tac ggc atc ctc agc gct ttc gcg cca gtg tat agc tgg atc       528
Leu Tyr Tyr Gly Ile Leu Ser Ala Phe Ala Pro Val Tyr Ser Trp Ile
                165                 170                 175 ctg gtg ctc cga ggc ctc gtg ggc ttt ggg att gga ggg gtg cct cag       576
Leu Val Leu Arg Gly Leu Val Gly Phe Gly Ile Gly Gly Val Pro Gln
            180                 185                 190 tcg gtg acc ctg tac gcc gag ttc ctc ccc atg aag gcc aga gcc aag       624
Ser Val Thr Leu Tyr Ala Glu Phe Leu Pro Met Lys Ala Arg Ala Lys
        195                 200                 205 tgc att ttg ctg att gag gtt ttc tgg gcc atc ggg acc gtg ttc gag       672
Cys Ile Leu Leu Ile Glu Val Phe Trp Ala Ile Gly Thr Val Phe Glu
    210                 215                 220
```

-continued

| | |
|---|---|
| gtg ctt ctg gct gtg ttt gtg atg ccc agc ctg ggc tgg cgc tgg ctg<br>Val Leu Leu Ala Val Phe Val Met Pro Ser Leu Gly Trp Arg Trp Leu<br>225                         230                    235                  240 | 720 |
| ctg ctg ctg tcg gcc gct cca cta ctt gtc ttt gct gtt ctg tgt ttc<br>Leu Leu Leu Ser Ala Ala Pro Leu Leu Val Phe Ala Val Leu Cys Phe<br>                        245                    250                  255 | 768 |
| tgg ctg cca gag agt gct agg tac gat gtg ctg tct ggg aac cag gaa<br>Trp Leu Pro Glu Ser Ala Arg Tyr Asp Val Leu Ser Gly Asn Gln Glu<br>          260                    265                  270 | 816 |
| aag gcg att gct acc tta aag cgg atc gca aca gaa aat gga gcc ccc<br>Lys Ala Ile Ala Thr Leu Lys Arg Ile Ala Thr Glu Asn Gly Ala Pro<br>                  275                    280                  285 | 864 |
| atg cct ctg ggg aag ctc atc atc tcc aga cag gaa gac cga ggc aaa<br>Met Pro Leu Gly Lys Leu Ile Ile Ser Arg Gln Glu Asp Arg Gly Lys<br>290                         295                    300 | 912 |
| atg agg gac ctt ttc aca ccc cac ttt cgt tgg aca act ctg ctg ctg<br>Met Arg Asp Leu Phe Thr Pro His Phe Arg Trp Thr Thr Leu Leu Leu<br>305                         310                    315                  320 | 960 |
| tgg ttt ata tgg ttc tcc aat gcc ttc tct tat tac ggc ttg gtt ctg<br>Trp Phe Ile Trp Phe Ser Asn Ala Phe Ser Tyr Tyr Gly Leu Val Leu<br>                        325                    330                  335 | 1008 |
| ctc acc aca gaa ctc ttc cag gcc gga gat gtt tgc agc atc tcc agc<br>Leu Thr Thr Glu Leu Phe Gln Ala Gly Asp Val Cys Ser Ile Ser Ser<br>                  340                    345                  350 | 1056 |
| cgg aag aag gcg gtg gaa gcc aaa tgc agc ctg gct tgt gag tac ctc<br>Arg Lys Lys Ala Val Glu Ala Lys Cys Ser Leu Ala Cys Glu Tyr Leu<br>          355                    360                  365 | 1104 |
| agc aaa gag gat tac atg gac ctg ctg tgg acc acc ctg tct gag ttc<br>Ser Lys Glu Asp Tyr Met Asp Leu Leu Trp Thr Thr Leu Ser Glu Phe<br>370                         375                    380 | 1152 |
| cca ggt gtc ctt gtg act ctg tgg gtc atc gac cgc ctg ggc cgc aag<br>Pro Gly Val Leu Val Thr Leu Trp Val Ile Asp Arg Leu Gly Arg Lys<br>385                         390                    395                  400 | 1200 |
| aag acc atg gct ctg tgt ttc gtc atc ttt tcc ctc tgc agc ctc ctg<br>Lys Thr Met Ala Leu Cys Phe Val Ile Phe Ser Leu Cys Ser Leu Leu<br>                  405                    410                  415 | 1248 |
| ctg ttc atc tgc att gga aga aat gtg cta acc ctc tta ctg ttc att<br>Leu Phe Ile Cys Ile Gly Arg Asn Val Leu Thr Leu Leu Leu Phe Ile<br>                  420                    425                  430 | 1296 |
| gca aga gcg ttt att tct gga ggc ttc caa gca gcc tac gtt tac acg<br>Ala Arg Ala Phe Ile Ser Gly Gly Phe Gln Ala Ala Tyr Val Tyr Thr<br>          435                    440                  445 | 1344 |
| cct gag gtg tat cca acg gcg acg agg gcg ctg ggc ctg ggc acc tgc<br>Pro Glu Val Tyr Pro Thr Ala Thr Arg Ala Leu Gly Leu Gly Thr Cys<br>450                         455                    460 | 1392 |
| agc ggc atg gca aga gtg ggc gcg ctc atc act cca ttc ata gct cag<br>Ser Gly Met Ala Arg Val Gly Ala Leu Ile Thr Pro Phe Ile Ala Gln<br>465                         470                    475                  480 | 1440 |
| gtg atg ctg gaa tct tcc gtg tac ctg acc ctg gcc gtc tac agt ggc<br>Val Met Leu Glu Ser Ser Val Tyr Leu Thr Leu Ala Val Tyr Ser Gly<br>                        485                    490                  495 | 1488 |
| tgc tgc ctc ctt gct gcc ttg gcc tcc tgc ttt ctg ccc atc gag acc<br>Cys Cys Leu Leu Ala Ala Leu Ala Ser Cys Phe Leu Pro Ile Glu Thr<br>                  500                    505                  510 | 1536 |
| aaa ggc cga gca ctg cag gag tcc agc cac cgg gag tgg ggc cag gag<br>Lys Gly Arg Ala Leu Gln Glu Ser Ser His Arg Glu Trp Gly Gln Glu<br>          515                    520                  525 | 1584 |
| atg gtt ggc cga ggg aca aac agc aca ggc gtc ccc agg tcg aac tct<br>Met Val Gly Arg Gly Thr Asn Ser Thr Gly Val Pro Arg Ser Asn Ser<br>530                         535                    540 | 1632 |

```
ggc tct cag gag tag                                              1647
Gly Ser Gln Glu
545
```

<210> SEQ ID NO 16
<211> LENGTH: 548
<212> TYPE: PRT
<213> ORGANISM: Rattus norvegicus

<400> SEQUENCE: 16

```
Met Glu Glu Asp Leu Phe Gln Leu Arg Gln Leu Pro Val Val Lys Phe
1               5                   10                  15

Arg Arg Thr Gly Glu Ser Ala Arg Ser Glu Asp Ala Ala Ser Gly
            20                  25                  30

Glu His Asp Val Gln Ile Glu Gly Val Arg Val Gly Leu Glu Ala Val
        35                  40                  45

Glu Leu Asp Asp Gly Ala Ala Val Pro Lys Glu Phe Ala Asn Pro Thr
    50                  55                  60

Asp Asp Thr Phe Met Val Glu Asp Ala Val Glu Ala Ile Gly Phe Gly
65                  70                  75                  80

Arg Phe Gln Trp Lys Leu Ser Val Leu Thr Gly Leu Ala Trp Met Ala
                85                  90                  95

Asp Ala Met Glu Met Met Ile Leu Ser Ile Leu Ala Pro Gln Leu His
            100                 105                 110

Cys Glu Trp Arg Leu Pro Ser Trp Gln Val Ala Leu Leu Thr Ser Val
        115                 120                 125

Val Phe Ile Gly Met Met Ser Ser Ser Thr Leu Trp Gly Asn Ile Ser
    130                 135                 140

Asp Gln Tyr Gly Arg Lys Thr Gly Leu Lys Ile Ser Val Phe Trp Thr
145                 150                 155                 160

Leu Tyr Tyr Gly Ile Leu Ser Ala Phe Ala Pro Val Tyr Ser Trp Ile
                165                 170                 175

Leu Val Leu Arg Gly Leu Val Gly Phe Gly Ile Gly Gly Val Pro Gln
            180                 185                 190

Ser Val Thr Leu Tyr Ala Glu Phe Leu Pro Met Lys Ala Arg Ala Lys
        195                 200                 205

Cys Ile Leu Leu Ile Glu Val Phe Trp Ala Ile Gly Thr Val Phe Glu
    210                 215                 220

Val Leu Leu Ala Val Phe Val Met Pro Ser Leu Gly Trp Arg Trp Leu
225                 230                 235                 240

Leu Leu Leu Ser Ala Ala Pro Leu Leu Val Phe Ala Val Leu Cys Phe
                245                 250                 255

Trp Leu Pro Glu Ser Ala Arg Tyr Asp Val Leu Ser Gly Asn Gln Glu
            260                 265                 270

Lys Ala Ile Ala Thr Leu Lys Arg Ile Ala Thr Glu Asn Gly Ala Pro
        275                 280                 285

Met Pro Leu Gly Lys Leu Ile Ile Ser Arg Gln Glu Asp Arg Gly Lys
    290                 295                 300

Met Arg Asp Leu Phe Thr Pro His Phe Arg Trp Thr Thr Leu Leu Leu
305                 310                 315                 320

Trp Phe Ile Trp Phe Ser Asn Ala Phe Ser Tyr Tyr Gly Leu Val Leu
                325                 330                 335

Leu Thr Thr Glu Leu Phe Gln Ala Gly Asp Val Cys Ser Ile Ser Ser
            340                 345                 350
```

-continued

```
Arg Lys Lys Ala Val Glu Ala Lys Cys Ser Leu Ala Cys Glu Tyr Leu
        355                 360                 365

Ser Lys Glu Asp Tyr Met Asp Leu Leu Trp Thr Thr Leu Ser Glu Phe
    370             375                 380

Pro Gly Val Leu Val Thr Leu Trp Val Ile Asp Arg Leu Gly Arg Lys
385                 390                 395                 400

Lys Thr Met Ala Leu Cys Phe Val Ile Phe Ser Leu Cys Ser Leu Leu
                405                 410             415

Leu Phe Ile Cys Ile Gly Arg Asn Val Leu Thr Leu Leu Leu Phe Ile
            420                 425                 430

Ala Arg Ala Phe Ile Ser Gly Gly Phe Gln Ala Ala Tyr Val Tyr Thr
        435                 440                 445

Pro Glu Val Tyr Pro Thr Ala Thr Arg Ala Leu Gly Leu Gly Thr Cys
    450                 455                 460

Ser Gly Met Ala Arg Val Gly Ala Leu Ile Thr Pro Phe Ile Ala Gln
465             470                 475                 480

Val Met Leu Glu Ser Ser Val Tyr Leu Thr Leu Ala Val Tyr Ser Gly
                485                 490                 495

Cys Cys Leu Leu Ala Ala Leu Ala Ser Cys Phe Leu Pro Ile Glu Thr
            500                 505                 510

Lys Gly Arg Ala Leu Gln Glu Ser Ser His Arg Glu Trp Gly Gln Glu
        515                 520                 525

Met Val Gly Arg Gly Thr Asn Ser Thr Gly Val Pro Arg Ser Asn Ser
    530                 535                 540

Gly Ser Gln Glu
545
```